(12) United States Patent
Toong et al.

(10) Patent No.: US 11,305,110 B2
(45) Date of Patent: Apr. 19, 2022

(54) DETECTION AND TREATMENT OF OBSTRUCTIVE SLEEP APNEA

(71) Applicant: Neurostim Technologies LLC, Waltham, MA (US)

(72) Inventors: Hoo-min D. Toong, Cambridge, MA (US); William C. Altmann, Austin, TX (US)

(73) Assignee: NEUROSTIM TECHNOLOGIES LLC, Waltham, MA (US)

( * ) Notice: Subject to any disclaimer, the term of this patent is extended or adjusted under 35 U.S.C. 154(b) by 160 days.

(21) Appl. No.: 16/823,476

(22) Filed: Mar. 19, 2020

(65) Prior Publication Data

US 2020/0297995 A1    Sep. 24, 2020

Related U.S. Application Data

(60) Provisional application No. 62/860,010, filed on Jun. 11, 2019, provisional application No. 62/822,252, filed on Mar. 22, 2019, provisional application No. 62/844,381, filed on May 7, 2019.

(51) Int. Cl.
*A61N 1/05* (2006.01)
*A61B 5/00* (2006.01)
*A61N 1/04* (2006.01)

(52) U.S. Cl.
CPC .......... *A61N 1/0548* (2013.01); *A61B 5/4818* (2013.01); *A61B 5/6833* (2013.01); *A61N 1/0452* (2013.01)

(58) Field of Classification Search
CPC .. A61N 1/0548; A61N 1/0452; A61B 5/6833; A61B 5/4818

USPC .......................................................... 607/42
See application file for complete search history.

(56) References Cited

U.S. PATENT DOCUMENTS

| 7,643,874 B2 | 1/2010 | Nitzan et al. |
| 7,689,285 B2 | 3/2010 | Garabet |
| 7,922,676 B2 | 4/2011 | Daskal et al. |
| 9,380,949 B2 | 7/2016 | Schuessler |

(Continued)

FOREIGN PATENT DOCUMENTS

| WO | 2009064641 A1 | 5/2009 |
| WO | 2015183620 A3 | 4/2016 |

OTHER PUBLICATIONS

Dreibati, B, et al.; Characterization of an electric stimulation protocol for muscular exercise; Annals of Physical and Rehabilitation Medicine; 2011; 54(1); 25-35.

(Continued)

*Primary Examiner* — Amanda K Hulbert
*Assistant Examiner* — Philip C Edwards
(74) *Attorney, Agent, or Firm* — Potomac Law Group, PLLC

(57) ABSTRACT

A treatment for obstructive sleep apnea ("OSA") of a user includes affixing a patch externally on a dermis of the user, the patch including a flexible substrate, an adhesive on a first side adapted to adhere to the dermis of the user, a processor directly coupled to the substrate, and electrodes directly coupled to the substrate. The treatment includes detecting an occurrence of OSA and activating the patch in response to the detecting, the activating including generating an electrical stimuli via the electrodes to activate the genioglossus muscle of the user.

22 Claims, 37 Drawing Sheets

(56) References Cited

U.S. PATENT DOCUMENTS

| | | | |
|---|---|---|---|
| 9,855,427 | B2 | 1/2018 | Bennett et al. |
| 9,962,121 | B2 | 5/2018 | Yoo |
| 10,136,857 | B2 | 11/2018 | Nuovo et al. |
| 10,342,977 | B2 | 7/2019 | Raghunathan |
| 2002/0019652 | A1 | 2/2002 | Silva et al. |
| 2004/0225226 | A1 | 11/2004 | Lehrman et al. |
| 2012/0192874 | A1* | 8/2012 | Bolea ............ A61N 1/37235 128/848 |
| 2014/0194951 | A1 | 7/2014 | Gong et al. |
| 2014/0324120 | A1 | 10/2014 | Bogie et al. |
| 2015/0018895 | A1* | 1/2015 | El Achhab ......... A61N 1/3601 607/42 |
| 2015/0157220 | A1 | 6/2015 | Fish et al. |
| 2015/0335888 | A1 | 11/2015 | Demers et al. |
| 2016/0015962 | A1 | 1/2016 | Maragheh et al. |
| 2016/0081620 | A1 | 3/2016 | Narayanan et al. |
| 2016/0128604 | A1 | 5/2016 | Eom et al. |
| 2016/0206239 | A1 | 7/2016 | Yoon et al. |
| 2016/0213979 | A1 | 7/2016 | Lee et al. |
| 2016/0287142 | A1 | 10/2016 | Han et al. |
| 2017/0001003 | A1 | 1/2017 | Pivonka et al. |
| 2017/0090475 | A1 | 3/2017 | Choi et al. |
| 2017/0143960 | A1* | 5/2017 | Kent .................. A61B 5/4818 |
| 2017/0181680 | A1 | 6/2017 | Baek et al. |
| 2017/0213450 | A1 | 7/2017 | Park et al. |
| 2017/0224990 | A1 | 8/2017 | Goldwasser et al. |
| 2017/0249429 | A1 | 8/2017 | Jain et al. |
| 2017/0333695 | A1 | 11/2017 | Kaplan et al. |
| 2018/0116606 | A1 | 5/2018 | Li et al. |
| 2018/0116877 | A1 | 5/2018 | Ineichen |
| 2018/0125422 | A1 | 5/2018 | Jang et al. |
| 2018/0133479 | A1 | 5/2018 | Bennett et al. |
| 2018/0279891 | A1 | 10/2018 | Miao et al. |
| 2018/0318585 | A1 | 11/2018 | Pfeifer |
| 2019/0000332 | A1 | 1/2019 | Li et al. |
| 2019/0038184 | A1 | 2/2019 | Narasimhan et al. |
| 2019/0046054 | A1 | 2/2019 | Li |
| 2020/0069941 | A1 | 3/2020 | Campean et al. |
| 2020/0069942 | A1 | 3/2020 | Campean et al. |

OTHER PUBLICATIONS

Eastwood, PR, et al.; Treating Obstructive Sleep Apnea with Hypoglossal Nerve Stimulation; Sleep; 2011; 34(11); 1479-1486.

Eckert, DJ, et al.; Genioglossus reflex inhibition to upper-airway negative-pressure stimuli during wakefulness and sleep in healthy males; Journal of Physiology; 2007; 581(3); 1193-1205.

Eckert, DJ, et al.; Pathophysiology of adult obstructive sleep apnea; Proceedings of the American Thoracic Society; 2008; 5(2); 144-153.

Edmonds, LC, et al.; The Effects of Transcutaneous Electrical Stimulation during Wakefulness and Sleep in Patients with Obstructive Sleep Apnea; American Review of Respiratory Disease; 1992; 146(4); 1030-1036.

Eisele, DW, et al.; Tongue neuromuscular and direct hypoglossal nerve stimulation for obstructive sleep apnea; Otolaryngologic Clinics of North America; 2003; 36(3); 501-510.

Eiseman, NA, et al.; The impact of body posture and sleep stages on sleep apnea severity in adults; Journal of Clinical Sleep Medicine; 2012; 8(6); 655-666.

Erden, F, et al.; Breathing detection based on the topological features of IR sensor and accelerometer signals; Conference Record—Asilomar Conference on Signals, Systems and Computers; 2017; 1763-1767.

Erdogan, F, et al.; Genioglossal response to mechanical vibrations of the mandible and the submandibular muscles; Journal of Applied Physiology; 2019; 127(1); 11-21.

Fitzpatrick, MF, et al.; Effect of nasal or oral breathing route on upper airway resistance during sleep; European Respiratory Journal; 2003; 22(5); 827-832.

Fleury Curado, T, et al.; Neurostimulation Treatment of OSA; Chest; 2018; 154(6); 1435-1447.

Fleury Curado, TA, et al.; Silencing of hypoglossal motoneurons leads to sleep disordered breathing in lean mice; Frontiers in Neurology; 2018; 9(NOV); 19-20.

Fleury, B; Pharyngeal musculature and obstructive sleep apnea syndromes; Revue des Maladies Respiratoires; 1999; 16(1); 51-56.

Fogel, RB, et al.; Reduced genioglossal activity with upper airway anesthesia in awake patients with OSA; Journal of Applied Physiology; 2000; 88(4); 1346-1354.

Fregosi, RF, et al.; Respiratory-related control of extrinsic tongue muscle activity; Respiration Physiology; 1997; 110(2-3); 295-306.

Freire, AO, et al.; Immediate effect of acupuncture on the sleep pattern of patients with obstructive sleep apnoea; Acupuncture in Medicine; 2010; 28(3); 115-119.

Freire, AO, et al.; Treatment of moderate obstructive sleep apnea syndrome with acupuncture: A randomised, placebo-controlled pilot trial; Sleep Medicine; 2007; 8(1); 43-50.

Friedman, M, et al.; Targeted hypoglossal nerve stimulation for the treatment of obstructive sleep apnea: Six-month results; Laryngoscope; 2016; 126(11); 2618-2623.

Garvey, JF, et al.; Epidemiological aspects of obstructive sleep apnea.; Journal of thoracic disease; 2015; 7(5); 920-9.

George, CF, et al.; Sleep apnea and body position during sleep; Sleep; 1988; 11(1); 90-99.

Guay, P, et al.; Wearable contactless respiration sensor based on multi-material fibers integrated into textile; Sensors (Switzerland); 2017; 17(5).

Güder, F, et al.; Paper-Based Electrical Respiration Sensor; Angewandte Chemie—International Edition; 2016; 55(19); 5727-5732.

Guilleminault, C, et al.; The effect of electrical stimulation on obstructive sleep apnea syndrome; Chest; 1995; 107(1); 67-73.

Haxhiu, MA, et al.; Comparison of the responses of the diaphragm and upper airway muscles to central stimulation of the sciatic nerve; Respiration Physiology; 1984; 58(1); 65-76.

He, B, et al.; Domiciliary use of transcutaneous electrical stimulation for patients with obstructive sleep apnoea: A conceptual framework for the TESLA home programme; Journal of Thoracic Disease; 2019; 11(5); 2153-2164.

He, D, et al.; An approach to sleep apnea syndrome detection based on change characteristics of blood oxygen saturation and pulse rate; 2018 IEEE International Conference on Real-Time Computing and Robotics, RCAR 2018; 2019; (0); 451-456.

Heiser, C, et al.; Nerve monitoring-guided selective hypoglossal nerve stimulation in obstructive sleep apnea patients; Laryngoscope; 2016; 126(12); 2852-2858.

Heiser, C, et al.; Selective upper airway stimulation for obstructive sleep apnea: a single center clinical experience; European Archives of Oto-Rhino-Laryngology; 2017; 274(3); 1727-1734.

Hida, W, et al.; Effects of submental stimulation for several consecutive nights in patients with obstructive sleep apnoea; Thorax; 1994; 49(5); 446-452.

Hida, W, et al.; The Effect of Submental Electrical Stimulation on Sleep Disordered Breathing in Patients with Obstructive Apnea; Sleep; 1993; 16(suppl_8); S96-S97.

Hida, W; New strategies of screening and treatment for sleep apnea syndrome.; The Tohoku journal of experimental medicine; 1998; 186(4); 225-241.

Hiyama, S, et al.; Genioglossus muscle activity during rhythmic open-close jaw movements; Journal of Oral Rehabilitation; 2000; 27(8); 664 670.

Hong, S ok, et al.; Hypoglossal nerve stimulation for treatment of obstructive sleep apnea (OSA): a primer for oral and maxillofacial surgeons; Maxillofacial Plastic and Reconstructive Surgery; 2017; 39(1); 1-10.

Horner, RL, et al.; Evidence for reflex upper airway dilator muscle activation by sudden negative airway pressure in man.; The Journal of Physiology; 1991; 436(1); 15-29.

Horner, RL, et al.; Reflex Pharyngeal Dilator Muscle Activation by Stimuli of Negative Airway Pressure in Awake Man; Sleep; 1993; 16(suppl_8); S85-S86.

Horner, RL, et al.; The effect of sleep on reflex genioglossus muscle activation by stimuli of negative airway pressure in humans.; The Journal of Physiology; 1994; 476(1); 141-151.

(56) References Cited

OTHER PUBLICATIONS

Hoshino, T, et al.; Effect of rapid eye movement-related obstructive sleep apnea on adherence to continuous positive airway pressure; Journal of International Medical Research; 2018; 46(6); 2238-2248.
Hsiao, MY, et al.; Ultrasonography in Assessing Oropharyngeal Dysphagia; Journal of Medical Ultrasound; 2013; 21(4); 181-188.
Hu, L, et al.; Percutaneous biphasic electrical stimulation for treatment of obstructive sleep apnea syndrome; IEEE Transactions on Biomedical Engineering; 2008; 55(1); 181-187.
Hu, Y, et al.; Current density distribution under surface electrode on posterior tibial nerve electrical stimulation; Annual International Conference of the IEEE Engineering in Medicine and Biology—Proceedings; 2005; 7 vols. (1); 3650-3652.
Hug, M, et al.; Screening for obstructive sleep apnea among hospital outpatients; PLoS ONE; 2018; 13(5); 1-17.
Hult, P, et al.; Method for respiration monitoring by the use of a bioacoustic signal; IEE Conference Publication; 2000; (476); 22-25.
Iaconetta, G, et al.; The Hypoglossal Nerve: Anatomical Study of Its Entire Course; World Neurosurgery; 2018; 109; e486-e492.
Inzelberg, L, et al.; Electrophysiology meets printed electronics: The beginning of a beautiful friendship; Frontiers in Neuroscience; 2019; 12; 1-14.
Isaiah, A, et al.; Ultrasonographic Detection of Airway Obstruction in a Model of Obstructive Sleep Apnea; Ultrasound International Open; 2017; 03(01); E34-E42.
Ishiwata, Y, et al.; Human jaw-tongue reflex as revealed by intraoral surface recording; Journal of Oral Rehabilitation; 2008; 24(11); 857-862.
Ishiwata, Y, et al.; Jaw-tongue reflex: Afferents, central pathways, and synoptic potentials in hypoglossal motoneurons in the cat; Journal of Dental Research; 2000; 79(8); 1626-1634.
Jafari, S, et al.; Sensory regulation of swallowing and airway protection: A role for the internal superior laryngeal nerve in humans; Journal of Physiology; 2003; 550(1); 287-304.
Javaheri, S, et al.; Sleep Apnea: Types, Mechanisms, and Clinical Cardiovascular Consequences; Journal of the American College of Cardiology; 2017; 69(7); 841-858.
Jordan, AS, et al.; Mechanisms used to restore ventilation after partial upper airway collapse during sleep in humans; Thorax; 2007; 62(10); 861-867.
Ahmadian, M; Transmission Line Matrix (TLM) modelling of medical ultrasound; Jun. 2001; 1-210.
Akahoshi, T, et al.; Phasic mechanoreceptor stimuli can induce phasic; 2001.
Akgul, YS, et al.; Automatic extraction and tracking of the tongue contours; IEEE Transactions on Medical Imaging; 1999; 18(10); 1035-1045.
Al Oweidat, K, et al.; Comparing REM- and NREM-Related Obstructive Sleep Apnea in Jordan: A Cross-Sectional Study; Canadian Respiratory Journal; 2018; 2018; 1-6.
Al-Abed, MA, et al.; Detection of airway occlusion in simulated obstructive sleep apnea/hypopnea using ultrasound: An in vitro study; 2010 Annual International Conference of the IEEE Engineering in Medicine and Biology Society, EMBC'10; 2010; 284-287.
Al-Abed, MA, et al.; In vivo characterization of ultrasonic transducers for the detection of airway occlusion in Sleep Disordered Breathing; Proceedings of the Annual International Conference of the IEEE Engineering in Medicine and Biology Society, EMBS; 2011; 7687-7690.
Al-Mardini, M, et al.; Classifying obstructive sleep apnea using smartphones; Journal of Biomedical Informatics; 2014; 52; 251-259.
Almazaydeh, L, et al.; Apnea detection based on respiratory signal classification; Procedia Computer Science; 2013; 21; 310-316.
Alves, P; Imaging the hypoglossal nerve; European Journal of Radiology; 2010; 74(2); 368-377.
Alzoubaidi, M, et al.; Obstructive sleep apnea during REM sleep; 2017; 22(6); 545-554.
Arlotto, P, et al.; An Ultrasonic Contactless Sensor for Breathing Monitoring; Sensors; 2014; 14(8); 15371-15386.
Armitage, H; Scientific innovations harness noise and acoustics for healing; Sound Research; 2019; 1-8.
Bailey, EF et al.; Firing patterns of human genioglossus motor units during voluntary tongue movement; Journal of Neurophysiology; 2007; 97(1); 933-936.
Barberi, L, et al.; Molecular and cellular mechanisms of muscle aging and sarcopenia and effects of electrical stimulation in seniors; European Journal of Translational Myology; 2015; 25(4); 231.
Barikroo, A, et al.; Transcutaneous electrical stimulation on the anterior neck region: The impact of pulse duration and frequency on maximum amplitude tolerance and perceived discomfort; Journal of Oral Rehabilitation; 2018; 45(6); 436-441.
Basner, RC, et al.; Breathing route influences upper airway muscle activity in awake normal adults; Journal of Applied Physiology; 1989; 66(4); 1766-1771.
Benjafield, A V., et al.; Estimation of the global prevalence and burden of obstructive sleep apnoea: a literature-based analysis; The Lancet Respiratory Medicine; 2019; 7(8); 687-698.
Benjafield, a, et al.; Global prevalence of obstructive sleep apnea in adults; Risk and prevalence of sleep disordered breathing; 2018; A3962-A3962.
Berry, GA, et al.; Note on Pflüger's Law of Contraction; Journal of anatomy and physiology; 1876; 10(Pt 3); 604-8.
Berry, RB, et al.; 0463 Validation of a Home Sleep Apnea Testing Device for the Diagnosis of Sleep Disordered Breathing based on AASM 2012 guidelines; Sleep; 2019; 42(Supplement_1); A186-A186.
Berry, RB, et al.; A novel nasal Expiratory Positive Airway Pressure (EPAP) device for the treatment of obstructive sleep apnea: A randomized controlled trial; Sleep; 2011; 34(4); 479-485.
Billings, ME; Interpreting Sleep Study Reports: A Primer for Pulmonary Fellows; 2019; 1-9.
Bisogni, V, et al.; Electrical stimulation for the treatment of obstructive sleep apnoea: a review of the evidence; Expert Review of Respiratory Medicine; 2017; 11(9); 711-720.
Blumen, M, et al.; Dilator muscles of the pharynx and their implication in the sleep apnea syndrome of obstructive type. Review of the literature; Annales d'oto-laryngologie etde chirurgie cervico faciale?: bulletin de la Société d'oto-laryngologie des hôpitaux de Paris; 1998; 115(2); 73-84.
Bogosanovi?, M, et al.; Microstrip antenna array with a beam focused in the near-field zone for application in noncontact microwave industrial inspection; IEEE Transactions on Instrumentation and Measurement; 2007; 56(6); 2186-2195.
Braley, T, et al.; OSA in older adults: Often present, seldom investigated; 2019; 1-4.
Braley, TJ, et al.; Recognition and Diagnosis of Obstructive Sleep Apnea in Older Americans; Journal of the American Geriatrics Society; 2018; 66(7); 1296-1302.
Bressmann, T; Quantitative Assessment of Tongue Shape and Movement Using Ultrasound Imaging; Proceedings from the 3rd Conference on Laboratory Approaches to Spanish Phonology; 2008; 101-106.
Bucklin, CL, et al.; An inexpensive accelerometer-based sleep-apnea screening technique; Proceedings of the IEEE 2010 National Aerospace and Electronics Conference, NAECON 2010; 2010; 396-399.
Buffi, A, et al.; Design criteria for near-field-focused planar arrays; IEEE Antennas and Propagation Magazine; 2012; 54(1); 40-50.
Campbell, T, et al.; Patients' preference of established and emerging treatment options for obstructive sleep apnoea; Journal of Thoracic Disease; 2015; 7(5); 938-942.
Castillo, Y, et al.; Characterization of microphones for snoring and breathing events analysis in mHealth; Proceedings of the Annual International Conference of the IEEE Engineering in Medicine and Biology Society, EMBS; 2017; 1547-1550.
Certal, VF, et al.; Hypoglossal nerve stimulation in the treatment of obstructive sleep apnea: A systematic review and meta-analysis; Laryngoscope; 2015; 125(5); 1254 1264.

(56) References Cited

OTHER PUBLICATIONS

Charthad, J, et al.; A mm-Sized wireless implantable device for electrical stimulation of peripheral nerves; IEEE Transactions on Biomedical Circuits and Systems; 2018; 12(2); 257-270.

Chen, B, et al.; Design and validation of a novel MR-compatible sensor for respiratory motion modeling and correction; IEEE Transactions on Biomedical Engineering; 2017; 64(1); 123-133.

Chen, J-W, et al.; 0461 Patterns of Tongue Thickness Changes in Obstructive Sleep Apnea Patients: A Whole-Night Simultaneous Ultrasound and Polysomnographic Study; Sleep; 2019; 42(Supplement_1); A185-A186.

Chen, JW, et al.; Simultaneous recording of ultrasound and polysomnography during natural sleep in patients with obstructive sleep apnea: a pilot study; Journal of Sleep Research; 2017; 26(4); 481-486.

Cheng, S, et al.; Movement of the tongue during normal breathing in awake healthy humans; Journal of Physiology; 2008; 586(17); 4283-4294.

Cherian, A, et al.; Ultrasound imaging of the airway and its applications; Airway; 2018; 1(1); 9-12.

Chwieśko-Minarowska, S, et al.; Efficacy of daytime transcutaneous electrical stimulation of the genioglossus muscle in patients with obstructive sleep apnea syndrome: short report; European Archives of Oto-Rhino-Laryngology; 2016; 273(11); 3891-3895.

Collop, NA, et al.; Obstructive sleep apnea devices for Out-Of-Center (OOC) testing: Technology evaluation; Journal of Clinical Sleep Medicine; 2011; 7(5); 531-548.

Corbishley, P, et al.; Breathing detection: Towards a miniaturized, wearable, battery-operated monitoring system; IEEE Transactions on Biomedical Engineering; 2008; 55(1); 196-204.

Cori, JM, et al.; Sleeping tongue: Current perspectives of genioglossus control in healthy individuals and patients with obstructive sleep apnea; Nature and Science of Sleep; 2018; 10; 169-179.

Daulatzai, MA; Role of Sensory Stimulation in Amelioration of Obstructive Sleep Apnea; Sleep Disorders; 2011; 2011; 1-12.

Decker, MJ, et al.; Functional electrical stimulation and respiration during sleep; Journal of Applied Physiology; 1993; 75(3); 1053-1061.

Dedhia, RC, et al.; Upper Airway Stimulation for Obstructive Sleep Apnea: Past, Present, and Future; Sleep; 2015; 26(4); 216-220.

Delaey, P, et al.; Specific branches of hypoglossal nerve to genioglossus muscle as a potential target of selective neurostimulation in obstructive sleep apnea: anatomical and morphometric study; Surgical and Radiologic Anatomy; 2017; 39(5); 507-515.

Dempsey, JA, et al.; Pathophysiology of sleep apnea; Physiological Reviews; 2010; 90(1); 47-112.

Dirjish, M; Respiration Sensor Embarks As A Smaller, Flexible Upgrade; 2019; 2017-2020.

Dotan, Y, et al.; Parameters affecting pharyngeal response to genioglossus stimulation in sleep apnoea; European Respiratory Journal; 2011; 38(2); 338-347.

Jordan, AS, et al.; Pharyngeal motor control and the pathogenesis of obstructive sleep apnea; Respiratory Physiology and Neurobiology; 2008; 160(1); 1-7.

Joy, K; Apnea?: New Guidelines Help Doctors Decide; 2019; 2017-2020.

Joy, K; When Is a Home Sleep Apnea Test Appropriate??; 2019; 1-4.

Kagaya, H, et al.; Development of peripheral magnetic stimulation system to stimulate suprahyoid muscles; Annals of Physical and Rehabilitation Medicine; 2018; 61; e348.

Kaniusas, E, et al.; Acoustical signal properties for cardiac/respiratory activity and apneas; IEEE Transactions on Biomedical Engineering; 2005; 52(11); 1812-1822.

Kesavan, K, et al.; Neuromodulation of limb proprioceptive afferents decreases apnea of prematurity and accompanying intermittent hypoxia and bradycardia; PLoS ONE; 2016; 11(6); 1-16.

Kezirian, EJ, et al.; NIH Public Access Apnea?: 12 Month Outcomes; 2015; 23(1); 77-83.

Kim, T, et al.; Detection of sleep disordered breathing severity using acoustic biomarker and machine learning techniques; BioMedical Engineering Online; 2018; 17(1); 1-19.

Kimoff, RJ, et al.; Mechanisms of apnea termination in obstructive sleep apnea: Role of chemoreceptor and mechanoreceptor stimuli; American Journal of Respiratory and Critical Care Medicine; 1994; 149(3 I); 707-714.

Kompelli, AR, et al.; The outcomes of hypoglossal nerve stimulation in the management of OSA: A systematic review and meta-analysis; World Journal of Otorhinolaryngology—Head and Neck Surgery; 2019; 5(1); 41-48.

Kroutil, J, et al.; Monitoring of Respiration by Bioacoustic Method; Short Paper Int. J. on Recent Trends in Engineering and Technology; 2011; 6(1); 128-130.

Kundra, P, et al.; Ultrasound of the airway; Indian Journal of Anaesthesia; 2011; 55(5); 456-462.

Kwan, BCH, et al.; A novel ultrasound technique to measure genioglossus movement in vivo; Journal of Applied Physiology; 2014; 117(5); 556-562.

Kwan, BCH, et al.; Influence of respiratory mechanics and drive on genioglossus movement under ultrasound imaging; PLoS ONE; 2018; 13(4); 1-15.

Kwan, BCH, et al.; Sagittal Measurement of Tongue Movement During Respiration: Comparison Between Ultrasonography and Magnetic Resonance Imaging; Ultrasound in Medicine and Biology; 2019; 45(4); 921-934.

Le, TQ, et al.; Nonlinear dynamics forecasting of obstructive sleep apnea onsets; PLoS ONE; 2016; 11(11); 1-12.

Lee, W, et al.; Epidemiology of obstructive sleep apnea: a population-based perspective; Expert Review of Respiratory Medicine; 2008; 2(3); 349-364.

Leiter, JC, et al.; Selective reflex activation of the genioglossus in humans; Journal of Applied Physiology; 1990; 68(6); 2581-2587.

Levendowski, DJ, et al.; Assessment of a neck-based treatment and monitoring device for positional obstructive sleep apnea; Journal of Clinical Sleep Medicine; 2014; 10(8); 863-871.

Li, GF, et al.; Improved Anatomical Specificity of Non-invasive Neuro-stimulation by High Frequency (5 MHz) Ultrasound; Scientific Reports; 2016; 6(April).

Li, Y, et al.; Effects of Chronic Sleep Fragmentation on Wake-Active Neurons and the Hypercapnic Arousal Response; Sleep; 2014; 37(1); 51-64.

Liu, GZ, et al.; Estimation of respiration rate from three-dimensional acceleration data based on body sensor network.; Telemedicine journal and e-health?: the official journal of the American Telemedicine Association; 2011; 17(9); 705-711.

Lorenzi-Filho, G, et al.; Treating OSA: Current and emerging therapies beyond CPAP; Respirology; 2017; 22(8); 1500-1507.

Luis, JA, et al.; Design and implementation of a smart sensor for respiratory rate monitoring; Sensors (Switzerland); 2014; 14(2); 3019-3032.

Lux, L; Effectiveness of Portable Monitoring Devices for Diagnosing Obstructive Sleep Apnea?: Update of a Systematic Review; 2004; (290); C3-C50.

Lv, ZT, et al.; The Clinical Effect of Acupuncture in the Treatment of Obstructive Sleep Apnea: A Systematic Review and Meta-Analysis of Randomized Controlled Trials; Evidence-based Complementary and Alternative Medicine; 2016; 2016.

Mador, MJ, et al.; Prevalence of positional sleep apnea in patients undergoing polysomnography; Chest; 2005; 128(4); 2130-2137.

Malhotra, A, et al.; Pharyngeal pressure and flow effects on genioglossus activation in normal subjects; American Journal of Respiratory and Critical Care Medicine; 2002; 165(1); 71-77.

Malhotra, A, et al.; Postural effects on pharyngeal protective reflex mechanisms; Sleep; 2004; 27(6); 1105-1112.

Malhotra, A; Hypoglossal-Nerve Stimulation for Obstructive Sleep Apnea; New England Journal of Medicine; 2014; 370(2); 170-171.

Marklund, M, et al.; Non-CPAP therapies in obstructive sleep apnoea: Mandibular advancement device therapy; European Respiratory Journal; 2012; 39(5); 1241-1247.

Marques, M, et al.; Effect of sleeping position on upper airway patency in obstructive sleep apnea is determined by the pharyngeal structure causing collapse; Sleep; 2017; 40(3); 4-11.

(56) References Cited

OTHER PUBLICATIONS

Marques, M, et al.; Retropalatal and retroglossal airway compliance in patients with obstructive sleep apnea; Respiratory Physiology and Neurobiology; 2018; 258; 98-103.
Martin-Harris, B; Coordination of respiration and swallowing; GI Motility online; 2006; 10; 1-26.
Mateika, JH, et al.; Response of human tongue protrudor and retractors to hypoxia and hypercapnia; American Journal of Respiratory and Critical Care Medicine; 1999; 160(6); 1976-1982.
Maurer, JT, et al.; Operative technique of upper airway stimulation: An implantable treatment of obstructive sleep apnea; Operative Techniques in Otolaryngology—Head and Neck Surgery; 2012; 23(3); 227-233.
McSharry, D, et al.; Genioglossus fatigue in obstructive sleep apnea; Respiratory Physiology and Neurobiology; 2012; 183(2); 59-66.
Medina, LE, et al.; Nerve excitation using an amplitude-modulated signal with kilohertz-frequency carrier and non-zero offset; Journal of NeuroEngineering and Rehabilitation; 2016; 13(1); 1-11.
Medina, LE, et al.; Volume conductor model of transcutaneous electrical stimulation with kilohertz signals; Journal of Neural Engineering; 2014; 11(6); 066012.
Meier, JH, et al.; Force recruitment during electrical nerve stimulation with multipolar intrafascicular electrodes; Medical & Biological Engineering & Computing; 1995; 33(3); 409-417.
Meisal, K; Tackling respiration monitoring with non-contact sensor technology; 2019; (Figure 1); 1-5.
Mendonça, F, et al.; Devices for home detection of obstructive sleep apnea: A review; Sleep Medicine Reviews; 2018; 41; 149-160.
Merritt, CR, et al.; Textile-based capacitive sensors for respiration monitoring; IEEE Sensors Journal; 2009; 9(1); 71-78.
Mezzanotte, WS, et al.; Influence of sleep onset on upper-airway muscle activity in apnea patients versus normal controls; American Journal of Respiratory and Critical Care Medicine; 1996; 153(6 I); 1880-1887.
Miki, H, et al.; Effects of pharyngeal lubrication on the opening of obstructed upper airway; Journal of Applied Physiology; 1992; 72(6); 2311-2316.
Miki, H, et al.; Effects of submental electrical stimulation during sleep on upper airway patency in patients with obstructive sleep apnea; American Review of Respiratory Disease; 1989; 140(5); 1285-1289.
Miller, AJ; Oral and Pharyngeal Reflexes in the Mammalian Nervous System: Their Diverse Range in Complexity and the Pivotal Role of the Tongue; Critical Reviews in Oral Biology & Medicine; 2002; 13(5); 409-425.
Mohamed, HM, et al.; Transcutaneous electrical nerve stimulation of the hypoglossal nerve as adjuvant treatment of obstructive sleep apnea; Jul. 2013; 147-152.
Mokhlesi, B, et al.; "REM-related" Obstructive Sleep Apnea: An Epiphenomenon or a Clinically Important Entity? Sleep; 2012; 35(1); 5-7.
Mokhlesi, B, et al.; Growing Evidence Linking OSA During Rapid Eye Movement Sleep to Systemic Hypertension; Chest; 2016; 150(3); 475-477.
Mokhlesi, B; REM-related obstructive sleep apnea: To treat or not to treat?; Journal of Clinical Sleep Medicine; 2012; 8(3); 249-250.
Morillo, DS, et al.; An Accelerometer-Based Device for Sleep Apnea Screening; IEEE Transactions on Information Technology in Biomedicine; 2010; 14(2); 491-499.
Morimoto, T, et al.; Effect of lingual nerve stimulation on hypoglossal motoneurons; Experimental Neurology; 1968; 22(2); 174-190.
Morimoto, T, et al.; Reflex activation of extrinsic tongue muscles by jaw closing muscle proprioceptors; The Japanese Journal of Physiology; 1978; 28(4); 461-471.
Morrell, MJ, et al.; Effect of surfactant on pharyngeal mechanics in sleeping humans: Implications for sleep apnoea; European Respiratory Journal; 2002; 20(2); 451-457.
Mu, L, et al.; Human tongue neuroanatomy: Nerve supply and motor endplates; Clinical Anatomy; 2010; 23(7); 777-791.

Mwenge, GB, et al.; Hypoglossal nerve stimulation for obstructive sleep apnea; Progress in Neurological Surgery; 2015; 29; 94-105.
Mwenge, GB, et al.; Targeted hypoglossal neurostimulation for obstructive sleep apnoea: A 1-year pilot study; European Respiratory Journal; 2013; 41(2); 360-367.
Nam, Y, et al.; Sleep monitoring based on a tri-axial accelerometer and a pressure sensor; Sensors (Switzerland); 2016; 16(5); 1-14.
Nandakumar, R, et al.; Contactless sleep apnea detection on smartphones; MobiSys 2015—Proceedings of the 13th Annual International Conference on Mobile Systems, Applications, and Services; 2015; 45-57.
Nishino, T; Physiological and pathophysiological implications of upper airway reflexes in humans; Japanese Journal of Physiology; 2000; 50(1); 3-14.
Niu, J, et al.; A Novel Method for Automatic Identification of Breathing State; Scientific Reports; 2019; 9(1); 1-13.
Okabe, S, et al.; Role of chemical drive in recruiting upper airway and inspiratory intercostal muscles in patients with obstructive sleep apnea; American Review of Respiratory Disease; 1993; 147(1); 190-195.
Oliven, A, et al.; Distribution of motor activity to expiratory muscles during sciatic nerve stimulation in the dog; Respiration Physiology; 1990; 81(2); 165-175.
Oliven, A, et al.; Effect of genioglossus contraction on pharyngeal lumen and airflow in sleep apnoea patients; European Respiratory Journal; 2007; 30(4); 748-758.
Omobomi, O, et al.; Positional therapy in the management of positional obstructive sleep apnea—a review of the current literature; Sleep and Breathing; 2018; 22(2); 297-304.
Ono, T; Tongue and upper airway function in subjects with and without obstructive sleep apnea; Japanese Dental Science Review; 2012; 48(2); 71-80.
Ozdemir, G, et al.; A Time-Series Approach to Predict Obstructive Sleep Apnea (OSA) Episodes; Proceedings of the 2nd World Congress on Electrical Engineering and Computer Systems and Science; 2016; 1-8.
Ozdemir, G, et al.; An Early Warning Algorithm to Predict Obstructive Sleep Apnea (OSA) Episodes; Avestia Publishing Journal of Biomedical Engineering and Biosciences; 2016; 3; 34-42.
Palmer, PM, et al.; Contributions of Individual Muscles to the Submental Surface Electromyogram During Swallowing; Journal of Speech, Language, and Hearing Research; 1999; 42(6); 1378-1391.
Pang, PCW, et al.; Monitoring respiratory activity in neonates using diaphragmatic electromyograph; Medical & Biological Engineering & Computing; 1995; 33(3); 385-390.
Pengo, MF, et al.; Emerging technology: Electrical stimulation in obstructive sleep apnoea; Journal of Thoracic Disease; 2015; 7(8); 1286-1297.
Pengo, MF, et al.; Randomised sham-controlled trial of transcutaneous electrical stimulation in obstructive sleep apnoea; Thorax; 2016; 71(10); 923-931.
Penzel, T, et al.; Ambulatory recording of sleep apnea using peripheral arterial tonometry; Annual International Conference of the IEEE Engineering in Medicine and Biology—Proceedings; 2004; 26 V; 3856-3859.
Peregrim, I, et al.; Does obstructive sleep apnea worsen during REM sleep?; Physiological Research; 2013; 62(5); 569-575.
Pillar, G, et al.; Genioglossal inspiratory activation: Central respiratory vs mechanoreceptive influences; Respiration Physiology; 2001; 127(1); 23-38.
Preston, JL, et al.; Ultrasound images of the tongue: A tutorial for assessment and remediation of speech sound errors; Journal of Visualized Experiments; 2017; 2017(119); 1-10.
Priyadarshan, S, et al.; Etiology of obstructive sleep apnoea syndrome; International Journal of Otorhinolaryngology and Head and Neck Surgery; 2017; 3(4); 952.
Punjabi, NM, et al.; Sleep-disordered breathing and mortality: A prospective cohort study; PLoS Medicine; 2009; 6(8).
Punjabi, NM; The epidemiology of adult obstructive sleep apnea; Proceedings of the American Thoracic Society; 2008; 5(2); 136-143.

(56) References Cited

OTHER PUBLICATIONS

Qing, KY, et al.; Burst-Modulated Waveforms Optimize Electrical Stimuli for Charge Efficiency and Fiber Selectivity; IEEE Transactions on Neural Systems and Rehabilitation Engineering; 2015; 23(6); 936-945.

Qing, KY; Optimizing the neural response to electrical stimulation and exploring new applications of neurostimulation.; Dissertation Abstracts International: Section B: The Sciences and Engineering; 2016; 77(1-B(E)); No-Specified.

Rajfur, J, et al.; Efficacy of selected electrical therapies on chronic low back pain: A comparative clinical pilot study; Medical Science Monitor; 2017; 23; 85-100.

Ramchandren, S, et al.; Hypoglossal nerve conduction findings in obstructive sleep apnea; Muscle & Nerve; 2010; 42(2); 257-261.

Randerath, WJ, et al.; Tongue-muscle training by intraoral electrical neurostimulation in patients with obstructive sleep apnea; Sleep; 2004; 27(2); 254-259.

Ravesloot, MJL, et al.; Obstructive Sleep Apnea (OSA) is the Most Prevalent Sleep Disordered Breathing Prob-Lem, Affecting 2% to 26% of the General population, depending on gender, age, and definition; Sleep; 2011; 34(1).

Ravesloot, MJL, et al.; Positional OSA part 2: retrospective cohort analysis with a new classification system (APOC); Sleep and Breathing; 2016; 20(2); 881-888.

Ravesloot, MJL, et al.; The undervalued potential of positional therapy in position-dependent snoring and obstructive sleep apnea—A review of the literature; Sleep and Breathing; 2013; 17(1); 39-49.

Remmers, JE; Wagging the Tongue and Guarding the Airway; American Journal of Respiratory and Critical Care Medicine; 2001; 164(11); 2013-2014.

Rodenstein, D, et al.; Residual effect of THN hypoglossal stimulation in obstructive sleep apnea: A disease-modifying therapy; American Journal of Respiratory and Critical Care Medicine; 2013; 187(11); 1276-1278.

Roebuck, A, et al.; A review of signals used in sleep analysis; Physiological Measurement; 2014; 35(1); R1-R57.

Rosenwein, T, et al.; Breath-by-breath detection of apneic events for OSA severity estimation using non-contact audio recordings; Proceedings of the Annual International Conference of the IEEE Engineering in Medicine and Biology Society, EMBS; 2015; Nov. 2015; 7688-7691.

Sagi-Dolev, AM, et al.; Three-dimensional current density distribution under surface stimulation electrodes; Medical & Biological Engineering & Computing; 1995; 33(3); 403-408.

Sahin, M, et al.; Obstructive Sleep Apnea: Electrical Stimulation Treatment; Wiley Encyclopedia of Biomedical Engineering; 2006; (1).

Sands, SA, et al.; New Approaches to Diagnosing Sleep-Disordered Breathing; Sleep Medicine Clinics; 2016; 11(2); 143-152.

Sankri-Tarbichi, A; Obstructive sleep apnea-hypopnea syndrome: Etiology and diagnosis; Avicenna Journal of Medicine; 2012; 2(1); 3.

Sawczuk, A, et al.; Neural control of tongue movement with respect to respiration and swallowing; Critical Reviews in Oral Biology and Medicine; 2001; 12(1); 18-37.

Schiefer, M, et al.; Sciatic nerve stimulation and its effects on upper airway resistance in the anesthetized rabbit model relevant to sleep apnea; Journal of Applied Physiology; 2018; 125(3); 763-769.

Schwartz, AR, et al.; Acute upper airway responses to hypoglossal nerve stimulation during sleep in obstructive sleep apnea; American Journal of Respiratory and Critical Care Medicine; 2012; 185(4); 420-426.

Schwartz, AR, et al.; Electrical stimulation of the hypoglossal nerve: A potential therapy; Journal of Applied Physiology; 2014; 116(3); 337-344.

Schwartz, AR, et al.; Electrical stimulation of the lingual musculature in obstructive sleep apnea; Journal of Applied Physiology; 1996; 81(2); 643-652.

Schwartz, AR, et al.; Therapeutic Electrical Stimulation of the Hypoglossal Nerve in Obstructive Sleep Apnea; Archives of Otolaryngology-Head & Neck Surgery; 2001; 127(10); 1216.

Selvaraj, N, et al.; Detection of sleep apnea on a per-second basis using respiratory signals; Proceedings of the Annual International Conference of the IEEE Engineering in Medicine and Biology Society, EMBS; 2013; 2124-2127.

Senaratna, C V., et al.; Prevalence of obstructive sleep apnea in the general population: A systematic review; Sleep Medicine Reviews; 2017; 34(October); 70-81.

Shaker, R; Reflex interaction of pharynx, esophagus , and airways?: GI Motility online p. 1 of 38 nature . com Reflex interaction of pharynx , esophagus , and airways; Review Literature And Arts Of The Americas; 2009; (2); 1-38.

Shevtsova, NA, et al.; Modulation of Respiratory System by Limb Muscle Afferents in Intact and Injured Spinal Cord; Frontiers in Neuroscience; 2019; 13; 1-26.

Shustak, S, et al.; Home monitoring of sleep with a temporary-tattoo EEG, EOG and EMG electrode array: A feasibility study; Journal of Neural Engineering; 2019; 16(2); 12-13.

Silverstein, K, et al.; Genioglossus muscle attachments: An anatomic analysis and the implications for genioglossus advancement; Oral Surgery, Oral Medicine, Oral Pathology, Oral Radiology, and Endodontics; 2000; 90(6); 686-688.

Slaughter, K, et al.; Neuromuscular organization of the superior longitudinalis muscle in the human tongue 1. Motor endplate morphology and muscle fiber architecture; Cells Tissues Organs; 2005; 181(1); 51-64.

Sluka, KA, et al.; What Makes Transcutaneous Electrical Nerve Stimulation Work? Making Sense of the Mixed Results in the Clinical Literature; Physical Therapy; 2013; 93(10); 1397-1402.

Sreedharan, S, et al.; Central sleep apnea in untreated hypothyroidism: A rare association; Thyroid Research and Practice; 2016; 13(2); 83.

Steier, J, et al.; Continuous transcutaneous submental electrical stimulation in obstructive sleep apnea: A feasibility study; Chest; 2011; 140(4); 998-1007.

Stepp, CE; Surface Electromyography for Speech and Swallowing Systems: Measurement, Analysis, and Interpretation; Journal of Speech, Language, and Hearing Research; 2012; 55(4); 1232-1246.

Stone, M, et al.; Speech patterns in a muscular hydrostat: normal and glossectomy tongue movement; Isbhi 2008; 2008; (Jan. 2007).

Stone, M; A guide to analysing tongue motion from ultrasound images; Clinical Linguistics & Phonetics; 2005; 19(6-7); 455-501.

Strohl, M.D., KP, et al.; Origins of and implementation concepts for upper airway stimulation therapy for obstructive sleep apnea; Respiratory Investigation; 2016; 54(4); 241-249.

Strollo, PJ, et al.; Upper-airway stimulation for obstructive sleep apnea; New England Journal of Medicine; 2014; 370(2); 139-149.

Su, CS, et al.; Functional outcomes in patients with REM-related obstructive sleep apnea treated with positive airway pressure therapy; Journal of Clinical Sleep Medicine; 2012; 8(3); 243-247.

Sunnetcioglu, A, et al.; Obstructive sleep apnea related to rapid-eye-movement or non-rapid-eye-movement sleep: comparison of demographic, anthropometric, and polysomnographic features; Jornal Brasileiro de Pneumologia; 2016; 42(1); 48-54.

Sweeney, JD, et al.; Neuromuscular stimulation selectivity of multiple-contact nerve cuff electrode arrays; Medical & Biological Engineering & Computing; 1995; 33(3); 418-425.

Takata, M, et al.; Two components of inhibitory postsynaptic potentials evoked in hypoglossal motoneurons by lingual nerve stimulation; Experimental Neurology; 1980; 69(2); 299-310.

Tan, JW, et al.; Electrical stimulation therapy improves sleep respiratory parameters in obstructive sleep apnea syndrome: A meta-analysis; Journal of Huazhong University of Science and Technology—Medical Science; 2013; 33(5); 623-627.

Taranto-Montemurro, L, et al.; Neural memory of the genioglossus muscle during sleep is stage-dependent in healthy subjects and obstructive sleep apnoea patients; Journal of Physiology; 2018; 596(21); 5163-5173.

Tiago, RSL, et al.; Morphometric aspects of the human hypoglossal nerve in adults and the elderly; Brazilian Journal of Otorhinolaryngology; 2005; 71(5); 554 558.

(56) References Cited

OTHER PUBLICATIONS

Tice, J; Portable Devices for Home Testing; 2005; 1-30.

Tolu, E, et al.; Muscle spindle and periodontal trigeminal afferents modulate the hypoglossal motoneuronal activity.; Archives italiennes de biologie; 1994; 132(2); 93-104.

Toney, GM, et al.; Sensory modalities conveyed in the hindlimb somatic afferent input to nucleus tractus solitarius; Journal of Applied Physiology; 2000; 88(6); 2062-2073.

Tran, WH, et al.; Development of asynchronous, intralingual electrical stimulation to treat obstructive sleep apnea; Annual International Conference of the IEEE Engineering in Medicine and Biology—Proceedings; 2003; 1(0); 375-378.

Van De Heyning, PH, et al.; Implanted upper airway stimulation device for obstructive sleep apnea; Laryngoscope; 2012; 122(7); 1626-1633.

Van Maanen, JP, et al.; Evaluation of a new simple treatment for positional sleep apnoea patients; Journal of Sleep Research; 2012; 21(3); 322-329.

Van Maanen, JP, et al.; Exploration of the relationship between sleep position and isolated tongue base or multilevel surgery in obstructive sleep apnea; European Archives of Oto-Rhino-Laryngology; 2012; 269(9); 2129-2136.

Vanderveken, OM, et al.; Evaluation of drug-induced sleep endoscopy as a patient selection tool for implanted upper airway stimulation for obstructive sleep apnea; Journal of Clinical Sleep Medicine; 2013; 9(5); 433-438.

Venancio, RC, et al.; Effects of carrier frequency of interferential current on pressure pain threshold and sensory comfort in humans; Archives of Physical Medicine and Rehabilitation; 2013; 94(1); 95-102.

Verse, T, et al.; Transkutane, submentale Elektrostimulationstherapie bei obstruktiver Schlafapnoe; HNO; 2003; 51(12); 966-970.

Watson, T; Russian Stimulation; 2012; (c); 1-7.

White, DP, et al.; Local reflex mechanisms: Influence on basal genioglossal muscle activation in normal subjects; Sleep; 1998; 21(7); 719-728.

Wray, CM, et al.; Hypoglossal nerve stimulation for obstructive sleep apnea: A review of the literature; World Journal of Otorhinolaryngology—Head and Neck Surgery; 2016; 2(4); 230-233.

Yadollahi, A, et al.; Sleep apnea monitoring and diagnosis based on pulse oximetery and tracheal sound signals; Medical and Biological Engineering and Computing; 2010; 48(11); 1087-1097.

Yamauchi, M, et al.; Nonrapid eye movement-predominant obstructive sleep apnea: Detection and mechanism; Journal of Clinical Sleep Medicine; 2015; 11(9); 987-993.

Yang, By, et al.; Accelerometer-based breathing signal acquisition with empirical mode decomposition; ICISA 2014—2014 5th International Conference on Information Science and Applications; 2014; 1-2.

Yang, H, et al.; The position of submaxillary transcutaneous electrical stimulation for obstructive sleep apnea syndrome; Zhonghua er bi yan hou ke za zhi; 2000; 35(1); 55-58.

Yap, SM, et al.; Reflex Tongue Protrusion as a Novel Release Phenomenon in Dementia in Adulthood; Movement Disorders Clinical Practice; 2018; 5(6); 661-662.

Younes, M, et al.; Genioglossus activity available via non-arousal mechanisms vs. that required for opening the airway in obstructive apnea patients; Journal of Applied Physiology; 2012; 112(2); 249-258.

Zaidi, FN, et al.; Tongue anatomy and physiology, the scientific basis for a novel targeted neurostimulation system designed for the treatment of obstructive sleep apnea; Neuromodulation; 2013; 16(4); 376-386.

Zhu, K, et al.; Influence of head position on obstructive sleep apnea severity; Sleep and Breathing; 2017; 21(4); 821-828.

Zulim, I, et al.; Antenna model for passive myelinated nerve fiber; 2015 23rd International Conference on Software, Telecommunications and Computer Networks, SoftCOM 2015; 2015; 87-91.

Zulim, I, et al.; Myelinated nerve fiber antenna model activation; 2016 24th International Conference on Software, Telecommunications and Computer Networks, SoftCOM 2016; 2016; c.

Yogi A. Patel; Kilohertz Electrical Stimulation Nerve Conduction Block: Effects of Electrode Surface Area; IEEE Transactions on Neural Systems and Rehabilitation Engineering, vol. 25, No. 10, Oct. 2017.

\* cited by examiner

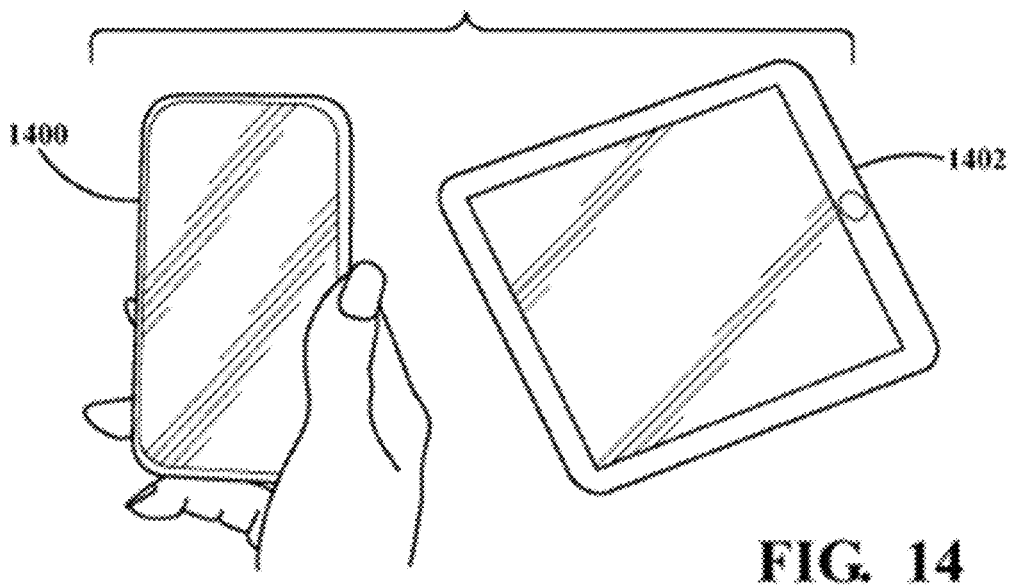
FIG. 14
FIG. 15
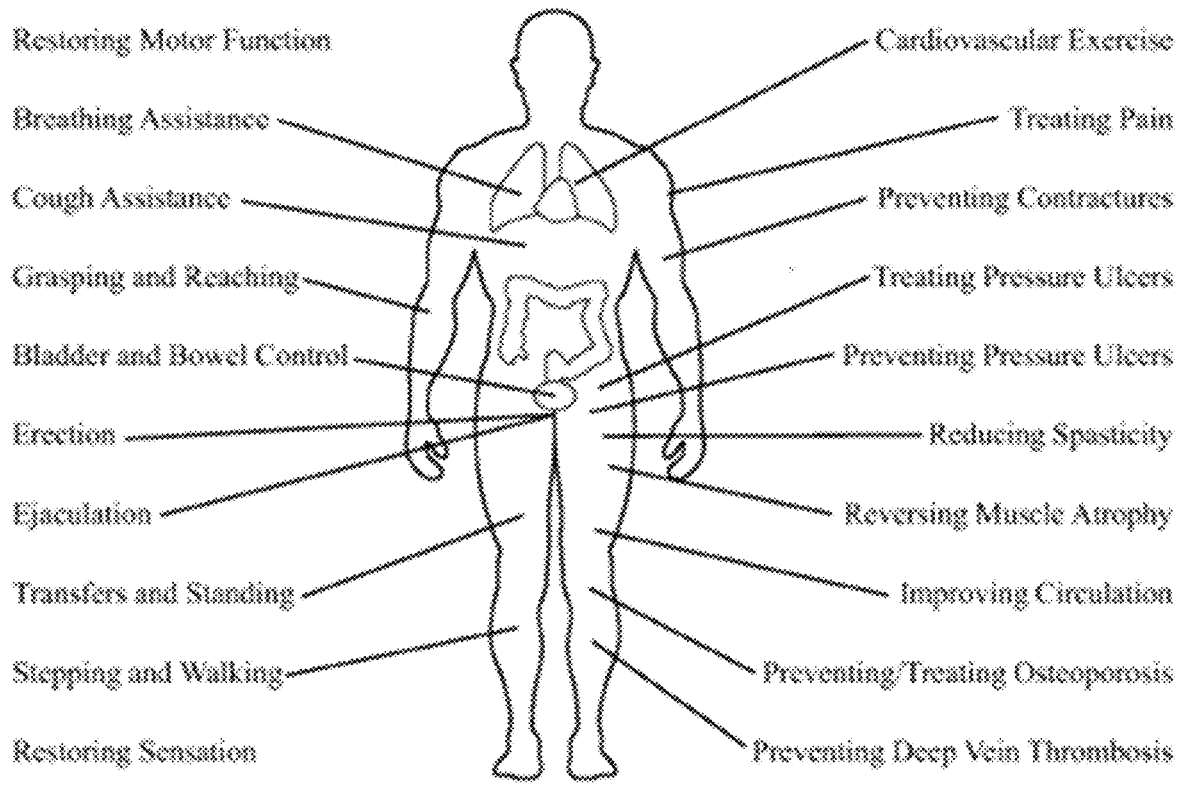

DETECTION AND TREATMENT OF OBSTRUCTIVE SLEEP APNEA

CROSS REFERENCE TO RELATED APPLICATIONS

This application claims priority to U.S. Provisional Patent Application Ser. No. 62/822,252, filed Mar. 22, 2019, U.S. Provisional Patent Application Ser. No. 62/844,381, filed May 7, 2019, and U.S. Provisional Patent Application Ser. No. 62/860,010, filed Jun. 11, 2019. The disclosure of each of these applications is hereby incorporated by reference.

FIELD

This invention is directed to obstructive sleep apnea, and more particularly to the detection and treatment, using externally applied electrical stimulation, of obstructive sleep apnea.

BACKGROUND INFORMATION

Obstructive sleep apnea (OSA) affects the quality of sleep. Obstructive sleep apnea is the intermittent occlusion of the upper airway (UAW), resulting in the reduction of airflow through the throat. This may be due to neuromuscular factors or anatomical causes. The muscles that keep the airway open when active can allow it to close when relaxed. An obstructed airflow causes imbalances in oxygen exchange, measurable in the hemoglobin of the blood.

BRIEF DESCRIPTION OF THE DRAWINGS

FIG. 14 are exemplary software platforms for communicating between the Control Units and the TNSS, gathering data, networking with other TNSSs, and external communications.

FIG. 15 represents TNSS applications for patients with spinal cord injury.

DETAILED DESCRIPTION

Figure 1:
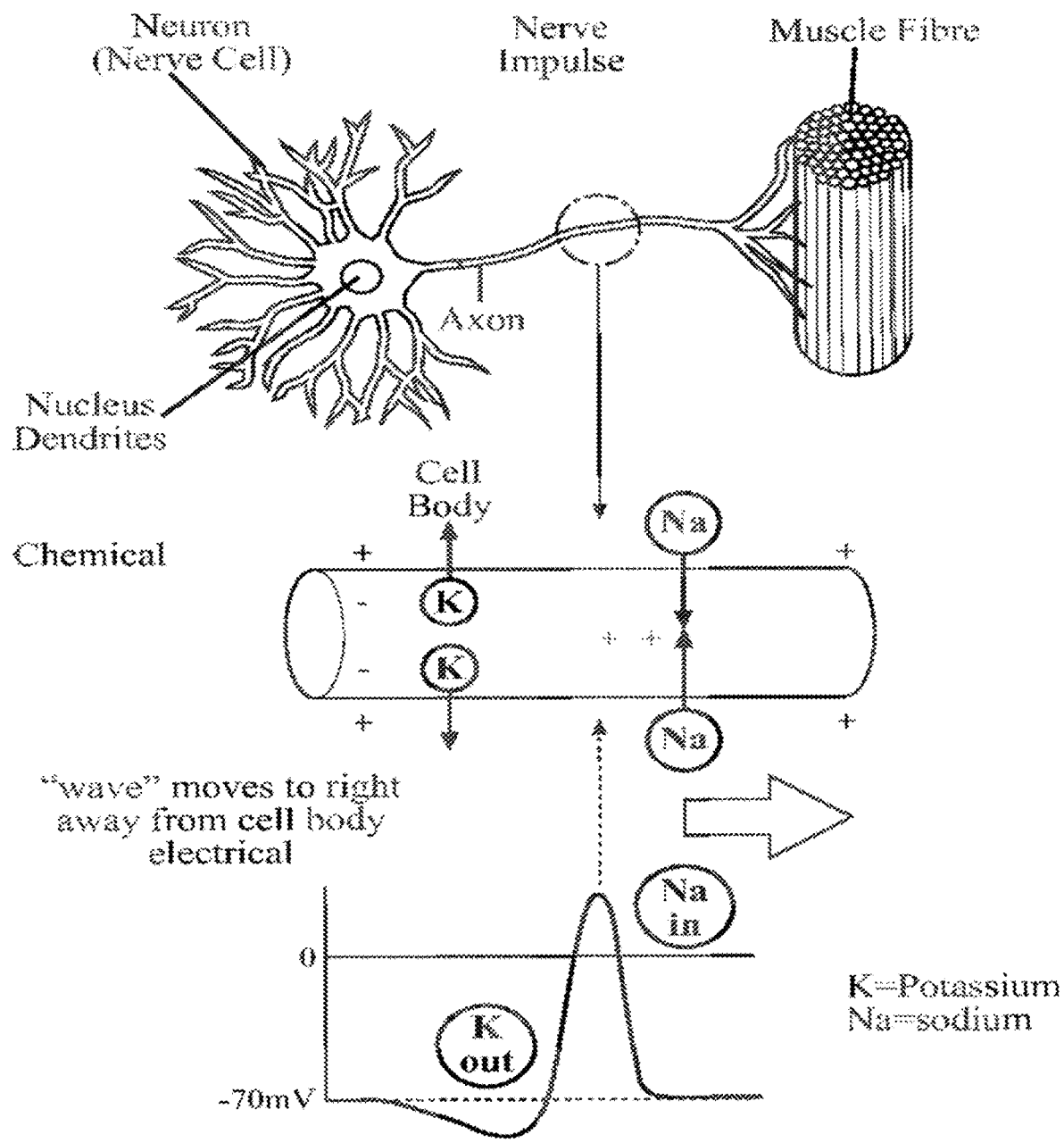
FIG. 1 is a depiction of a neuron activating a muscle by electrical impulse.

Example inventions can be used to detect and treat obstructive sleep apnea ("OSA"). Examples provide a method and system to address the effects of OSA without the discomfort and complexity of continuous positive airway pressure ("CPAP") machines or the use of surgically implanted devices. Further, examples are directed to a method for electrical, mechanical, chemical and/or optical interaction with a human or mammal nervous system to stimulate and/or record body functions using small electronic devices attached to the skin and capable of being wirelessly linked to and controlled by a cellphone, activator or computer network The body is controlled by a chemical system and a nervous system. Nerves and muscles produce and respond to electrical voltages and currents. Electrical stimulation of these tissues can restore movement or feeling when these have been lost, or can modify the behavior of the nervous system, a process known as neuro modulation. Recording of the electrical activity of nerves and muscles is widely used for diagnosis, as in the electrocardiogram, electromyogram, electroencephalogram, etc. Electrical stimulation and recording require electrical interfaces for input and output of information. Electrical interfaces between tissues and electronic systems are usually one of three types:

a. Devices implanted surgically into the body, such as pacemakers. These are being developed for a variety of functions, such as restoring movement to paralyzed muscles or restoring hearing, and can potentially be applied to any nerve or muscle. These are typically specialized and somewhat expensive devices.

b. Devices inserted temporarily into the tissues, such as needles or catheters, connected to other equipment outside the body. Health care practitioners use these devices for diagnosis or short-term treatment.

c. Devices that record voltage from the surface of the skin for diagnosis and data collection, or apply electrical stimuli to the surface of the skin using adhesive patches connected to a stimulator. Portable battery-powered stimulators have typically been simple devices operated by a patient, for example for pain relief. Their use has been limited by;

i. The inconvenience of chronically managing wires, patches and stimulator, particularly if there are interfaces to more than one site, and ii. The difficulty for patients to control a variety of stimulus parameters such as amplitude, frequency, pulse width, duty cycle, etc.

Nerves can also be stimulated mechanically to produce sensation or provoke or alter reflexes; this is the basis of touch sensation and tactile feedback. Nerves can also be affected chemically by medications delivered locally or systemically and sometimes targeted to particular nerves on the basis of location or chemical type. Nerves can also be stimulated or inhibited optically if they have had genes inserted to make them light sensitive like some of the nerves in the eye. The actions of nerves also produce electrical, mechanical and chemical changes that can be sensed.

The topical nerve stimulator/sensor (TNSS) is a device to stimulate nerves and sense the actions of the body that can be placed on the skin of a human or mammal to act on and respond to a nerve, muscle or tissue. One implementation of the TNSS is the Smart Band Aid™ (SBA). A system, incorporating a SBA, controls neuro modulation and neuro stimulation activities. It consists of one or more controllers or Control Units, one or more TNSS modules, software that resides in Control Units and TNSS modules, wireless communication between these components, and a data managing platform. The controller hosts software that will control the functions of the TNSS. The controller takes inputs from the TNSS of data or image data for analysis by said software, The controller provides a physical user interface for display to and recording from the user, such as activating or disabling the TNSS, logging of data and usage statistics, generating reporting data. Finally, the controller provides communications with other Controllers or the Internet cloud.

The controller communicates with the Neurostim module, also called TNSS module or SBA or patch, and also communicates with the user. In at least one example, both of these communications can go in both directions, so each set of communications is a control loop. Optionally, there may also be a control loop directly between the TNSS module and the body. So the system optionally may be a hierarchical control system with at least four control loops. One loop is between the TNSS and the body; another loop is between the TNSS and the controller; another loop is between the controller and the user; and another loop is between the controller and other users via the cloud. Each control loop has several functions including: (1) sending activation or disablement signals between the controller and the TNSS via a local network such as Bluetooth; (2) driving the user interface, as when the controller receives commands from the user and provides visual, auditory or tactile feedback to the user; (3) analyzing TNSS data, as well as other feedback data such as from the user, within the TNSS, and/or the controller and/or or the cloud; (4) making decisions about the appropriate treatment; (5) system diagnostics for operational correctness; and (6) communications with other controllers or users via the Internet cloud for data transmission or exchange, or to interact with apps residing in the Internet cloud.

The control loop is closed. This is as a result of having both stimulating and sensing. The sensing provides information about the effects of stimulation, allowing the stimulation to be adjusted to a desired level or improved automatically.

Typically, stimulation will be applied. Sensing will be used to measure the effects of stimulation. The measurements sensed will be used to specify the next stimulation. This process can be repeated indefinitely with various durations of each part. For example (where "a" is applying stimulation, "b" is sensing the results of stimulation, and "c" is correcting or revising the stimulation based on the applying and sensing): rapid cycling through the process (a-b-c-a-b-c-a-b-c); prolonged stimulation, occasional sensing (aaaa-b-c-aaaa-b-c-aaaa-b-c); or prolonged sensing, occasional stimulation (a-bbbb-c-a-bbbb-c-a-bbbb). The process may also start with sensing, and when an event in the body is detected this information is used to specify stimulation to treat or correct the event, for example, (bbbbbbbbb-c-a-bbbbbbbb-c-a-bbbbbbbb). Other patterns are possible and contemplated within the scope of the application.

The same components can be used for stimulating and sensing alternately, by switching their connection between the stimulating circuits and the sensing circuits. The switching can be done by standard electronic components. In the case of electrical stimulating and sensing, the same electrodes can be used for both. An electronic switch is used to connect stimulating circuits to the electrodes and electric stimulation is applied to the tissues. Then the electronic switch disconnects the stimulating circuits from the electrodes and connects the sensing circuits to the electrodes and electrical signals from the tissues are recorded.

In the case of acoustic stimulating and sensing, the same ultrasonic transducers can be used for both (as in ultrasound imaging or radar). An electronic switch is used to connect circuits to the transducers to send acoustic signals (sound waves) into the tissues. Then the electronic switch disconnects these circuits from the transducers and connects other circuits to the transducers (to listen for reflected sound waves) and these acoustic signals from the tissues are recorded.

Other modalities of stimulation and sensing may be used (e.g. light, magnetic fields, etc.) The closed loop control may be implemented autonomously by an individual TNSS or by multiple TNSS modules operating in a system such as that shown below in FIG. 16. Sensing might be carried out by some TNSSs and stimulation by others.

Stimulators are protocol controlled initiators of electrical stimulation, where such protocol may reside in either the TNSS and/or the controller and/or the cloud. Stimulators interact with associated sensors or activators, such as electrodes or MEMS devices.

The protocol, which may be located in the TNSS, the controller or the cloud, has several functions including:

(1) Sending activation or disablement signals between the controller and the TNSS via a local network such as Bluetooth. The protocol sends a signal by Bluetooth radio waves from the smartphone to the TNSS module on the skin, telling it to start or stop stimulating or sensing. Other wireless communication types are possible.

(2) Driving the user interface, as when the controller receives commands from the user and provides visual, auditory or tactile feedback to the user. The protocol receives a command from the user when the user touches an icon on the smartphone screen, and provides feedback to the user by displaying information on the smartphone screen, or causing the smartphone to beep or buzz.

(3) Analyzing TNSS data, as well as other feedback data such as from the user, within the TNSS, and/or the controller and/or or the cloud. The protocol analyzes data sensed by the TNSS, such as the position of a muscle, and data from the user such as the user's desires as expressed when the user touches an icon on the smartphone; this analysis can be done in the TNSS, in the smartphone, and/or in the cloud.

(4) Making decisions about the appropriate treatment. The protocol uses the data it analyzes to decide what stimulation to apply.

(5) System diagnostics for operational correctness. The protocol checks that the TNSS system is operating correctly.

(6) Communications with other controllers or users via the Internet cloud for data transmission or exchange, or to interact with apps residing in the Internet cloud. The protocol communicates with other smartphones or people via the internet wirelessly; this may include sending data over the internet, or using computer programs that are operating elsewhere on the internet.

A neurological control system, method and apparatus are configured in an ecosystem or modular platform that uses potentially disposable topical devices to provide interfaces between electronic computing systems and neural systems. These interfaces may be direct electrical connections via electrodes or may be indirect via transducers (sensors and actuators). It may have the following elements in various configurations: electrodes for sensing or activating electrical events in the body; actuators of various modalities; sensors of various modalities; wireless networking; and protocol applications, e.g. for data processing, recording, control systems. These components are integrated within the disposable topical device. This integration allows the topical device to function autonomously. It also allows the topical device along with a remote control unit (communicating wirelessly via an antenna, transmitter and receiver) to function autonomously.

Referring to FIG. 1, nerve cells are normally electrically polarized with the interior of the nerve being at an electric potential 70 mV negative relative to the exterior of the cell. Application of a suitable electric voltage to a nerve cell (raising the resting potential of the cell from −70 mV to above the firing threshold of −55 mV) can initiate a sequence of events in which this polarization is temporarily reversed in one region of the cell membrane and the change in polarization spreads along the length of the cell to influence other cells at a distance, e.g. to communicate with other nerve cells or to cause or prevent muscle contraction.

Figure 2:
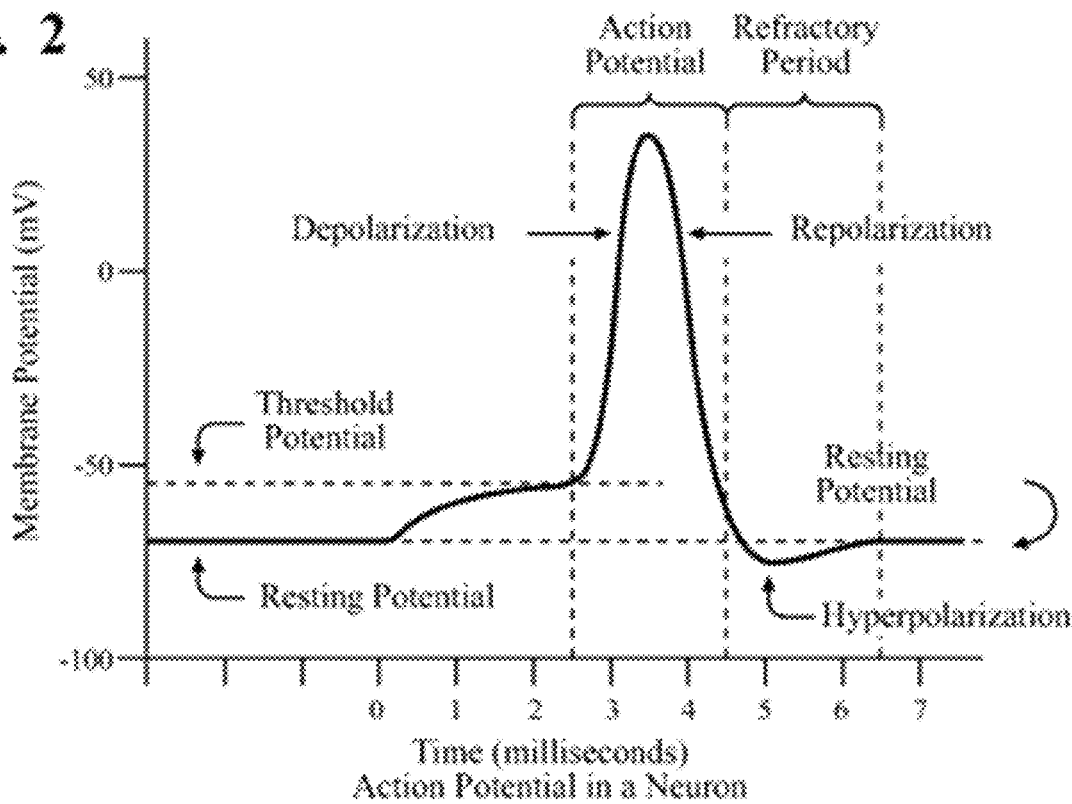
FIG. 2 is a representation of the electrical potential activation time of an electrical impulse in a nerve.

Referring to FIG. 2, a nerve impulse is graphically represented from a point of stimulation resulting in a wave of depolarization followed by a repolarization that travels along the membrane of a neuron during the measured period. This spreading action potential is a nerve impulse. It is this phenomenon that allows for external electrical nerve stimulation.

Figure 3:
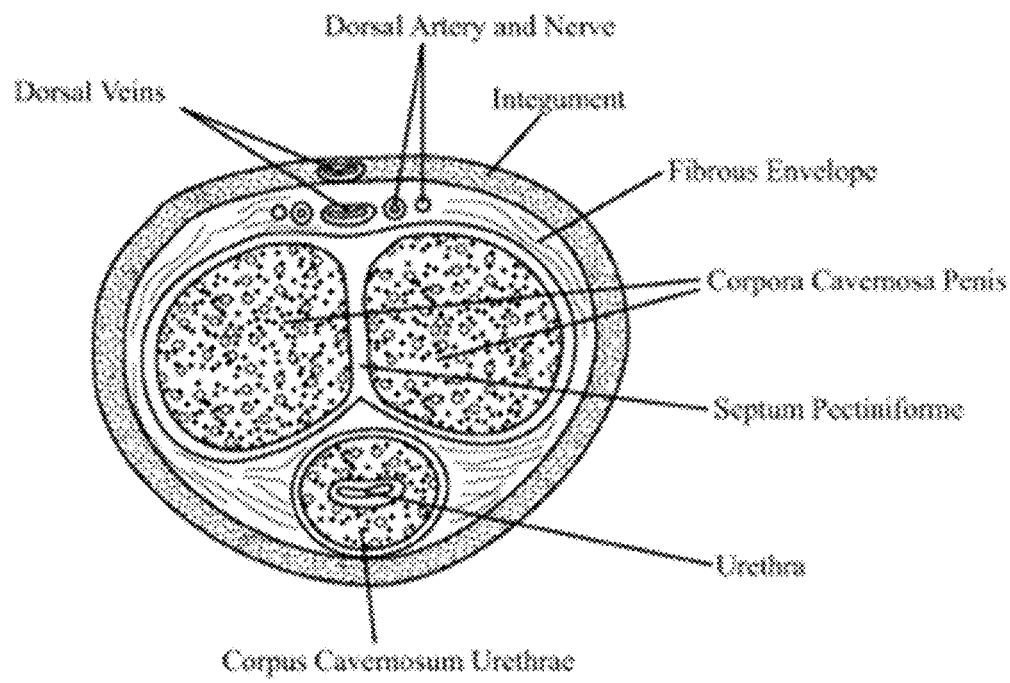
FIG. 3 is a cross section of a penis.

Referring to FIG. 3, the dorsal genital nerve on the back of the penis or clitoris just under the skin is a purely sensory nerve that is involved in normal inhibition of the activity of the bladder during sexual activity, and electrical stimulation of this nerve has been shown to reduce the symptoms of the Over Active Bladder. Stimulation of the underside of the penis may cause sexual arousal, erection, ejaculation and orgasm.

A Topical nerve stimulator/sensor (TNSS) is used to stimulate these nerves and is convenient, unobtrusive, self-powered, controlled from a smartphone or other control device. This has the advantage of being non-invasive, controlled by consumers themselves, and potentially distributed over the counter without a prescription.

Figure 4:
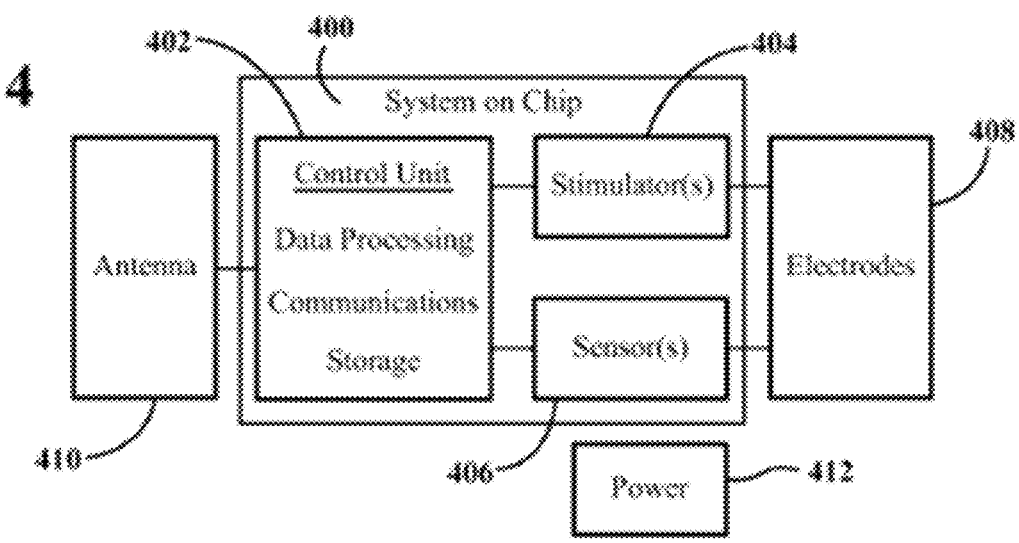
FIG. 4 is an illustration of a Topical Nerve Stimulator/Sensor (TNSS) component configuration including a system on a chip (SOC).

Referring to FIG. 4, the TNSS has one or more electronic circuits or chips that perform the functions of: communications with the controller, nerve stimulation via electrodes 408 that produce a wide range of electric field(s) according to treatment regimen, one or more antennae 410 that may also serve as electrodes and communication pathways, and a wide range of sensors 406 such as, but not limited to, mechanical motion and pressure, temperature, humidity, chemical and positioning sensors. One arrangement would be to integrate a wide variety of these functions into an SOC, system on chip 400. Within this is shown a control unit 402 for data processing, communications and storage and one or more stimulators 404 and sensors 406 that are connected to electrodes 408. An antenna 410 is incorporated for external communications by the control unit. Also present is an internal power supply 412, which may be, for example, a battery. An external power supply is another variation of the chip configuration. It may be necessary to include more than one chip to accommodate a wide range of voltages for data processing and stimulation. Electronic circuits and chips will communicate with each other via conductive tracks within the device capable of transferring data and/or power.

In one or more examples, a Smart Band Aid™ incorporating a battery and electronic circuit and electrodes in the form of adhesive conductive pads may be applied to the skin, and electrical stimuli is passed from the adhesive pads into the tissues. Stimuli may typically be trains of voltage-regulated square waves at frequencies between 15 and 50 Hz with currents between 20 and 100 mA. In other examples, the stimuli includes square waves having an amplitude between 10 and 100 volts, pulse widths between 100 and 500 microseconds, and a pulse repetition rate of between 3 and 30 pulses per second. The trains of stimuli are controlled from a smartphone operated by the user. Stimuli may be either initiated by the user when desired, or programmed according to a timed schedule, or initiated in response to an event detected by a sensor on the Smart Band Aid™ or elsewhere. Another implementation for males may be a TNSS incorporated in a ring that locates a stimulator conductively to selected nerves in a penis to be stimulated.

Figure 5:
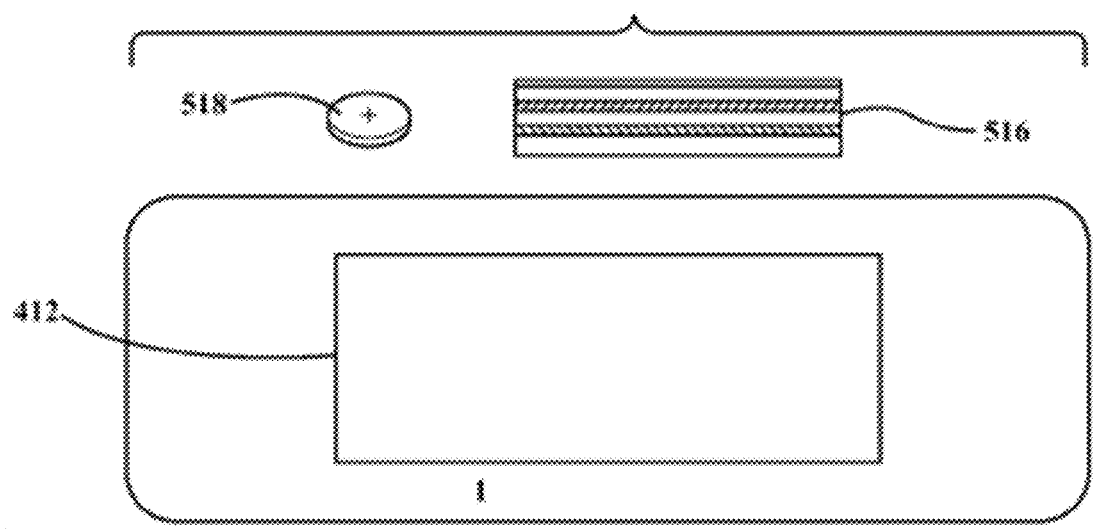
FIG. 5 is an illustration of the upper side of a Smart Band Aid implementation of a TNSS showing location of battery, which may be of various types.

Referring to FIG. 5, limited lifetime battery sources will be employed as internal power supply 412, to power the TNSS deployed in this illustration as a Smart Band Aid™. These may take the form of Lithium Ion technology or traditional non-toxic Mn02 technologies. FIG. 5 illustrates different battery options such as a printable Manganese Oxide battery 516 and a button battery 518. A TNSS of different shapes may require different battery packaging.

Figure 6:
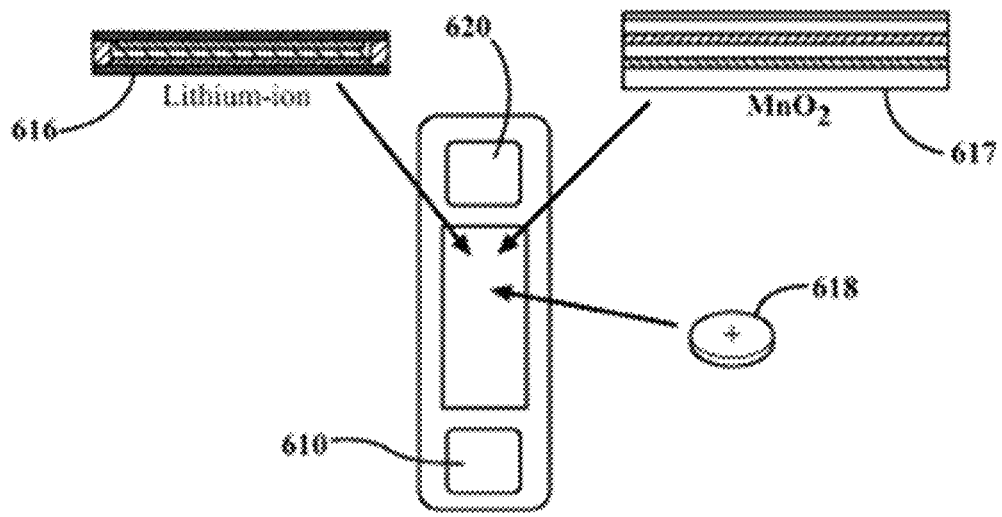
FIG. 6 is an illustration of the lower side of the SBA of FIG. 5.

FIG. 6 shows an alternate arrangement of these components where the batteries 616-618 are positioned on the bottom side of the SBA between the electrodes 610 and 620. In this example, battery 616 is a lithium ion battery, battery 617 is a Mn02 battery and battery 618 is a button battery. Other types of batteries and other battery configurations are possible within the scope of this application in other examples.

Aside from the Controller, the Smart Band Aid™ Packaging Platform (also referred to as a "smart patch" or "patch") consists of an assembly of an adhesive patch capable of being applied to the skin and containing the TNSS Electronics, protocol, and power described above.

Figure 7:
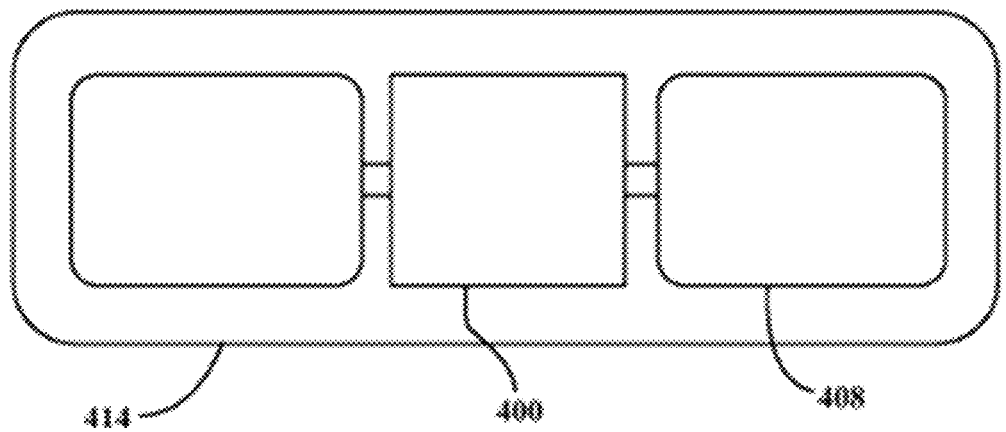
FIG. 7 is TNSS components incorporated into a SBA.

Referring to FIG. 7 is a TNSS deployed as a Smart Band Aid™ 414. The Smart Band Aid™ has a substrate with adhesive on a side for adherence to skin, the SOC 400 previously described in FIG. 4, or electronic package, and electrodes 408 disposed between the dermis and the adhesive surface. The electrodes provide electrical stimuli through the dermis to nerves and other tissue and in turn may collect electrical signals from the body, such as the electrical signals produced by muscles when they contract (the electromyogram) to provide data about body functions such as muscle actions.

Figure 8:
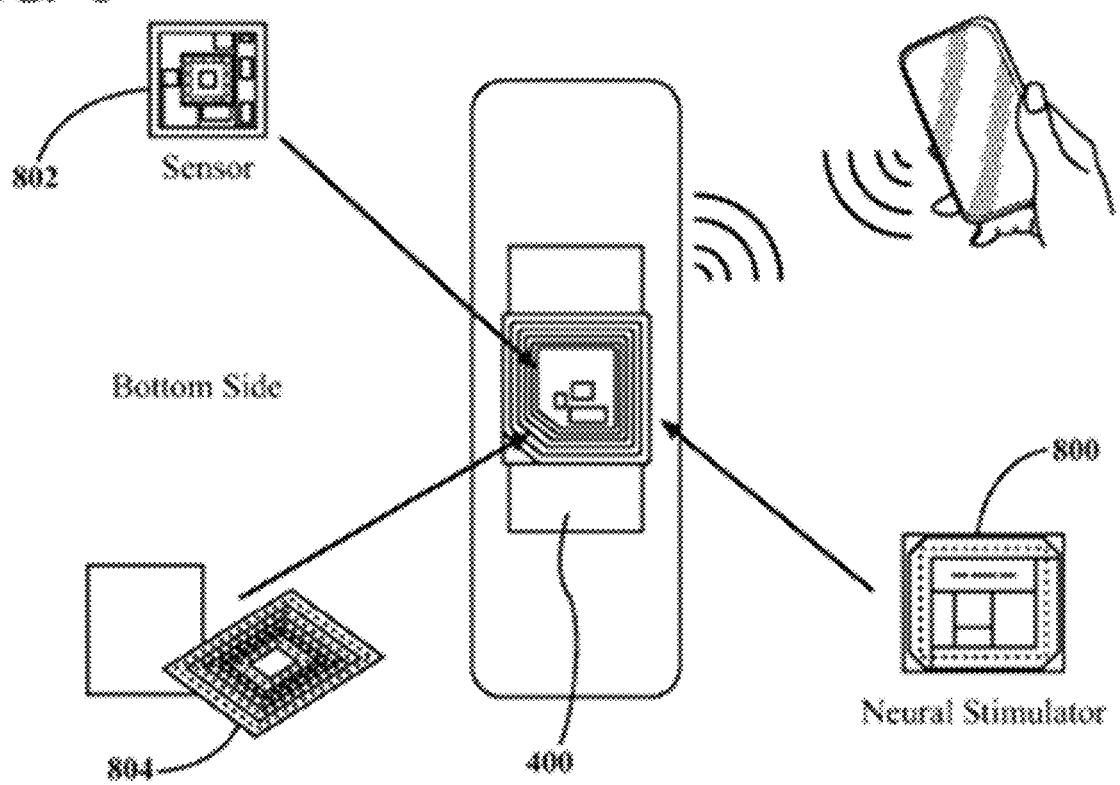
FIG. 8 is examples of optional neural stimulator and sensor chip sets incorporated into a SBA.

Referring to FIG. 8, different chips may be employed to design requirements. Shown are sample chips for packaging in a TNSS in this instance deployed as a SBA. For example, neural stimulator 800, sensor 802, processor/communications 804 are represented. The chips can be packaged separately on a substrate, including a flexible material, or as a system-on-chip (SOC) 400. The chip connections and electronics package are not shown but are known in the art.

Figure 9:
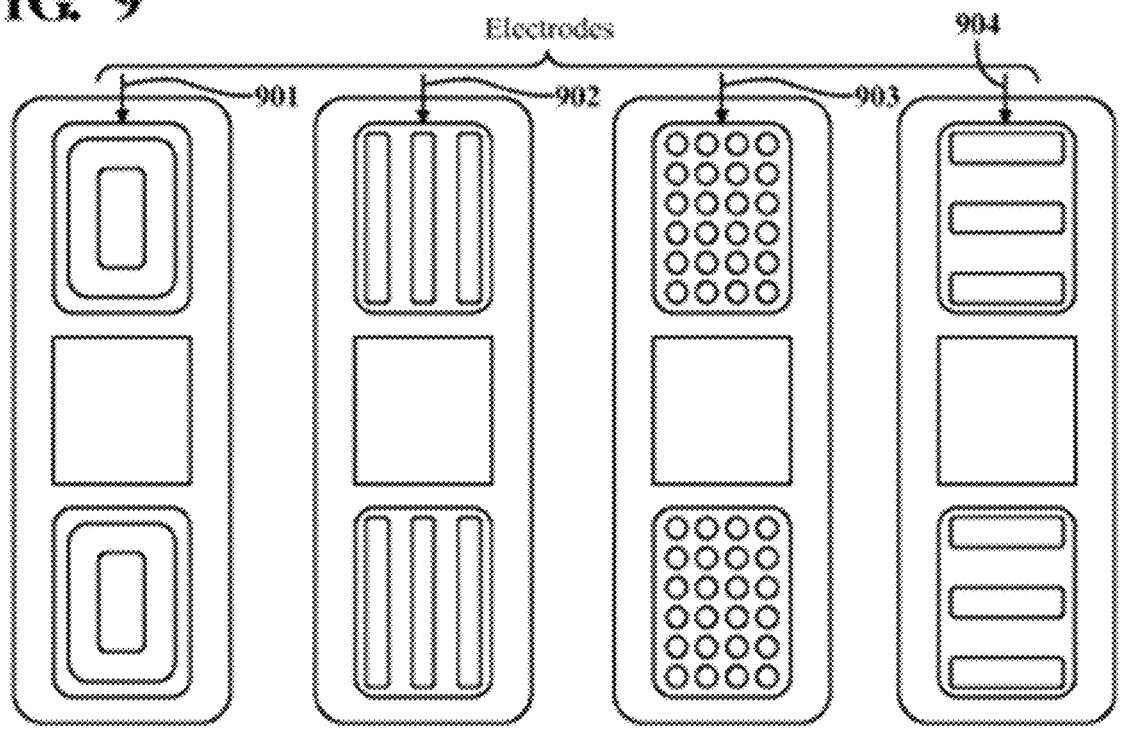
FIG. 9 is examples of optional electrode configurations for a SBA.

Referring to FIG. 9, SBAs with variations on arrangements of electrodes are shown. Each electrode may consist of a plurality of conductive contacts that give the electrode abilities to adjust the depth, directionality, and spatial distribution of the applied electric field. For all the example electrode configurations shown, 901-904, the depth of the electrical stimulation can be controlled by the voltage and power applied to the electrode contacts. Electric current can be applied to various electrode contacts at opposite end of the SBA, or within a plurality of electrode contacts on a single end of the SBA. The phase relationship of the signals applied to the electrode contacts can vary the directionality of the electric field. For all configurations of electrodes, the applied signals can vary over time and spatial dimensions. The configuration on the left, 901, shows a plurality of concentric electrode contacts at either end of the SBA. This configuration can be used to apply an electric stimulating field at various tissue depths by varying the power introduced to the electrode contacts. The next configuration, 902, shows electrodes 404 that are arranged in a plurality of parallel strips of electrical contacts. This allows the electric field to be oriented perpendicular or parallel to the SBA. The next configuration, 903, shows an example matrix of electrode contacts where the applied signal can generate a stimulating field between any two or more electrode contacts at either end of the SBA, or between two or more electrode contacts within a single matrix at one end of the SBA. Finally, the next configuration on the far right, 904, also shows electrodes that are arranged in a plurality of parallel strips of electrical contacts. As with the second configuration, this allows the electric field to be oriented perpendicular or parallel to the SBA. There may be many other arrangements of electrodes and contacts.

One or more TNSSs with one or more Controllers form a System. Systems can communicate and interact with each other and with distributed virtualized processing and storage services. This enables the gathering, exchange, and analysis of data among populations of systems for medical and non-medical applications.

Figure 10:
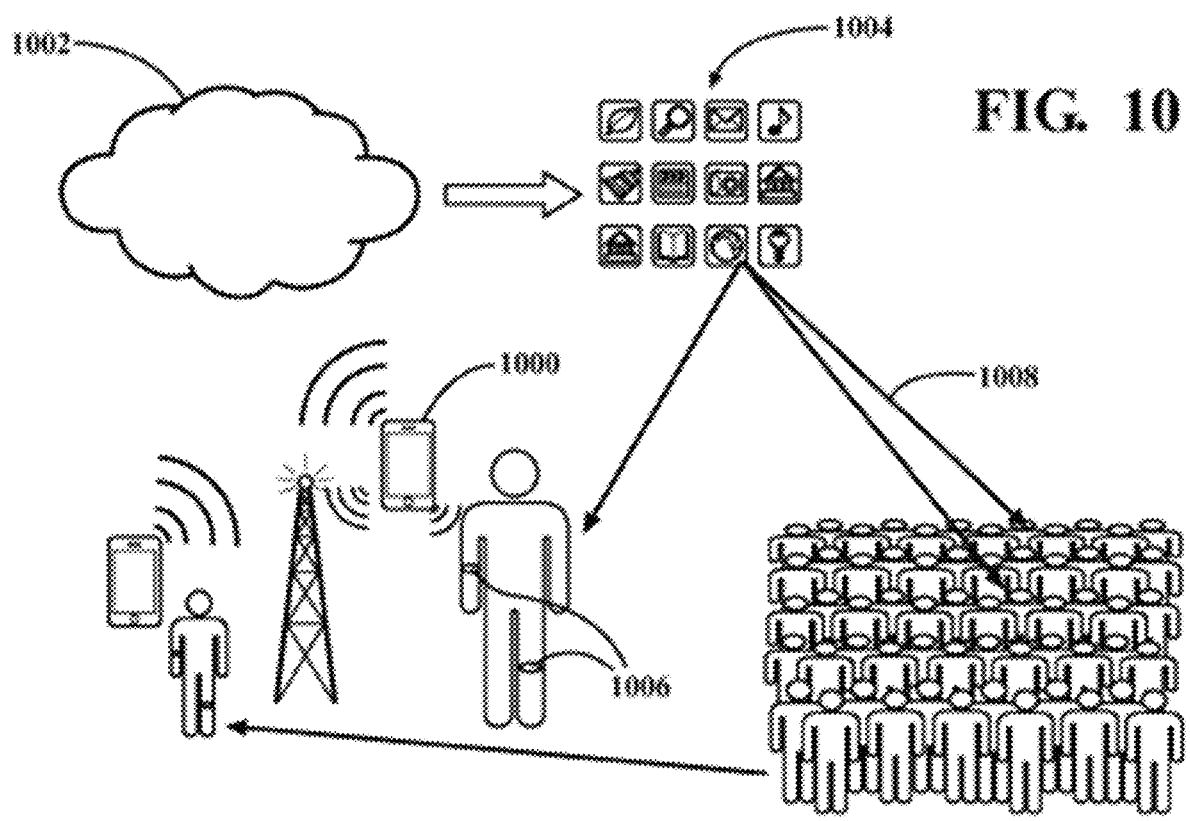
FIG. 10 is an example of the use of TNSS with a Control Unit as a System, in a population of Systems and software applications.

Referring to FIG. 10, a system is shown with two TNSS units 1006, with one on the wrist, one on the leg, communicating with its controller, a smartphone 1000 or other control device. The TNSS units can be both sensing and stimulating and can act independently and also work together in a Body Area Network (BAN). Systems communicate with each other over a communication bridge or network such as a cellular network. Systems also communicate with applications running in a distributed virtualized processing and storage environment generally via the Internet 1002. The purpose for communications with the distributed virtualized processing and storage environment is to communicate large amounts of user data for analysis and networking with other third parties such as hospitals, doctors, insurance companies, researchers, and others. There are applications that gather, exchange, and analyze data from multiple Systems 1004. Third party application developers can access TNSS systems and their data to deliver a wide range of applications. These applications can return data or control signals to the individual wearing the TNSS unit 1006. These applications can also send data or control signals to other members of the population who employ systems 1008. This may represent an individual's data, aggregated data from a population of users, data analyses, or supplementary data from other sources.

Figure 11:
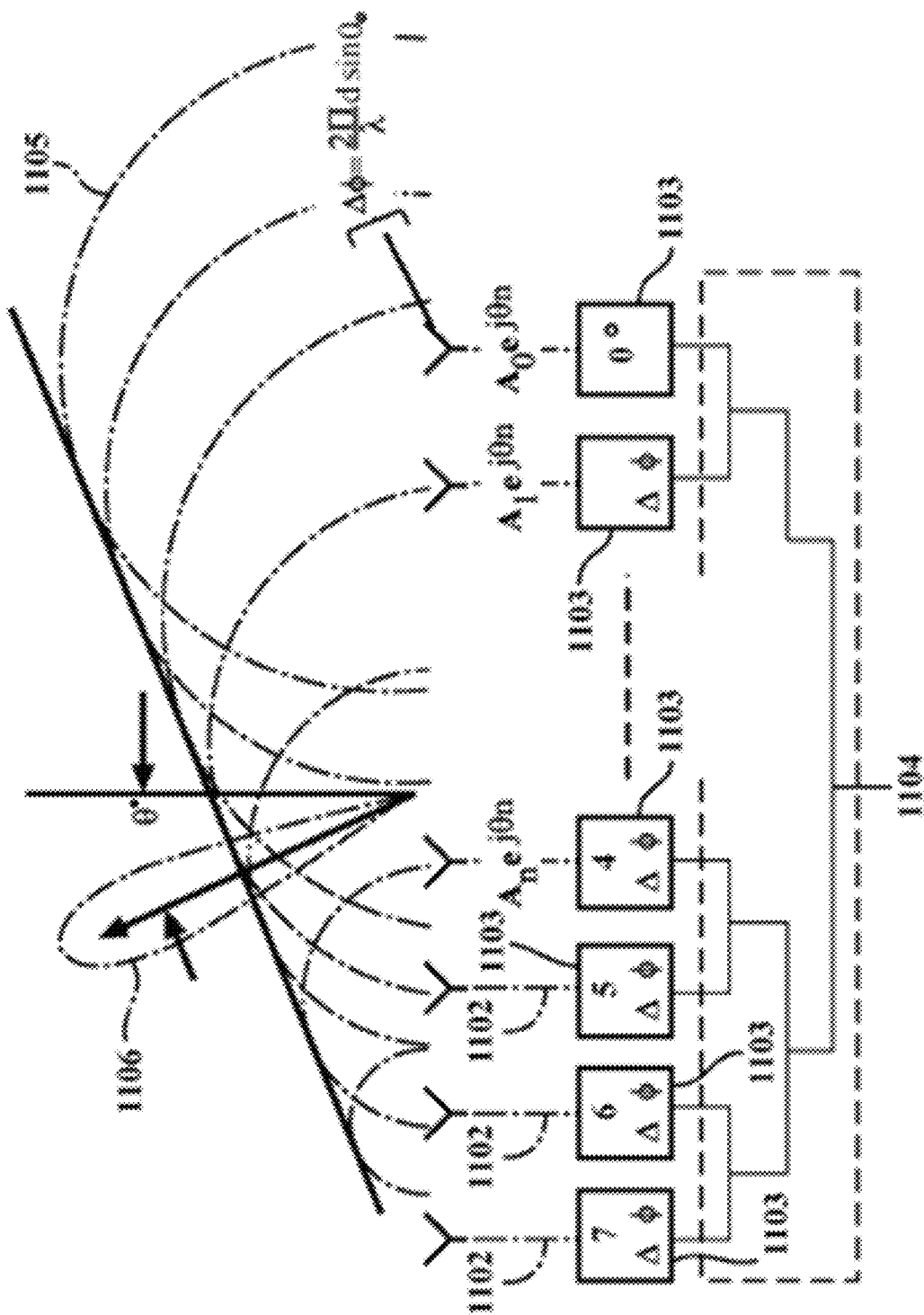
FIG. 11 shows a method for forming and steering a beam by the user of a plurality of radiators.

Referring to FIG. 11, shown is an example of an electrode array to affect beam forming and beam steering. Beam forming and steering allows a more selective application of stimulation energy by a TNSS to nerves and tissue. Beam steering also provides the opportunity for lower power for stimulation of cells including nerves by applying the stimulating mechanism directionally to a target. In the use of an electrical beam lower power demand lengthens battery life and allows for use of low power chip sets. Beam steering may be accomplished in multiple ways for instance by magnetic fields and formed gates. FIG. 11 shows a method for forming and steering a beam by the use of a plurality of radiators 1102 which are activated out of phase with each other by a plurality of phase shifters 1103 that are supplied power from a common source 1104. Because the radiated signals are out of phase they produce an interference pattern 1105 that results in the beam being formed and steered in varying controlled directions 1106. Electromagnetic radiation like light shows some properties of waves and can be focused on certain locations. This provides the opportunity to stimulate tissues such as nerves selectively. It also provides the opportunity to focus the transmission of energy and data on certain objects, including topical or implanted electronic devices, thereby not only improving the selectivity of activating or controlling those objects but also reducing the overall power required to operate them.

Figure 12:
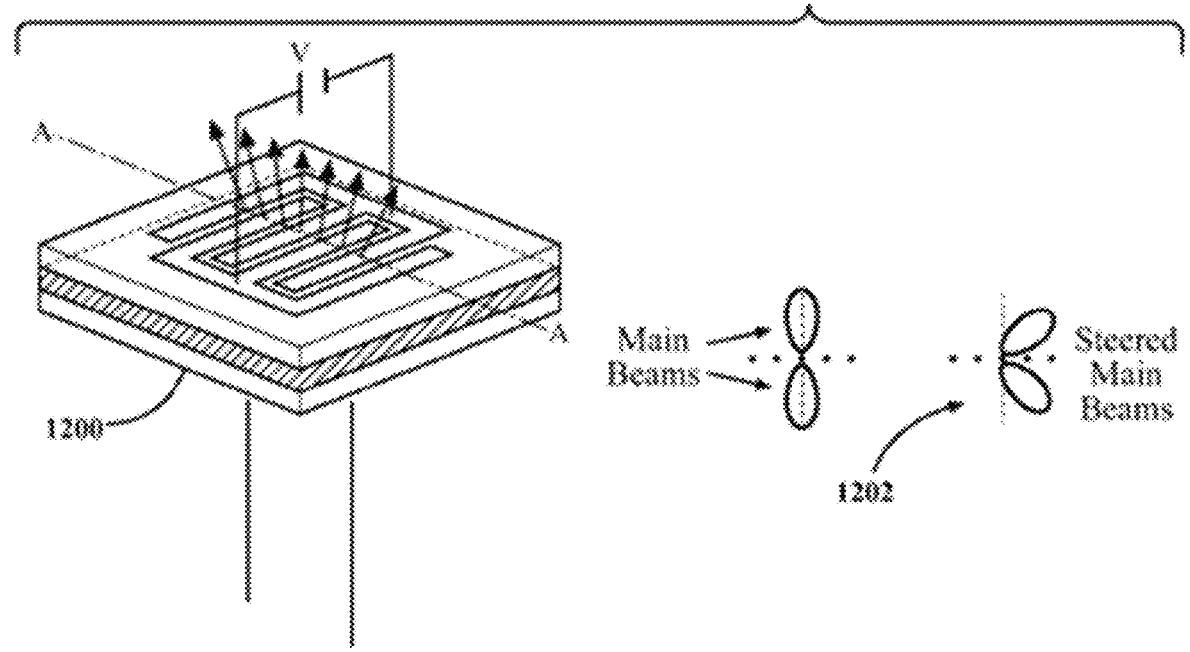
FIG. 12 is an exemplary beam forming and steering mechanism.

FIG. 12 is another example of a gating structure 1200 used for beam shaping and steering 1202. The gating structure 1200 shows an example of an interlocked pair of electrodes that can be used for simple beam forming through the application of time-varying voltages. The steering 1202 shows a generic picture of the main field lobes and how such beam steering works in this example. FIG. 12 is illustrative of a possible example that may be used.

The human and mammal body is an anisotropic medium with multiple layers of tissue of varying electrical properties. Steering of an electric field may be accomplished using multiple electrodes, or multiple SBAs, using the human or mammal body as an anisotropic volume conductor. Electric field steering will discussed below with reference to FIGS. 18 and 19.

Figure 13:
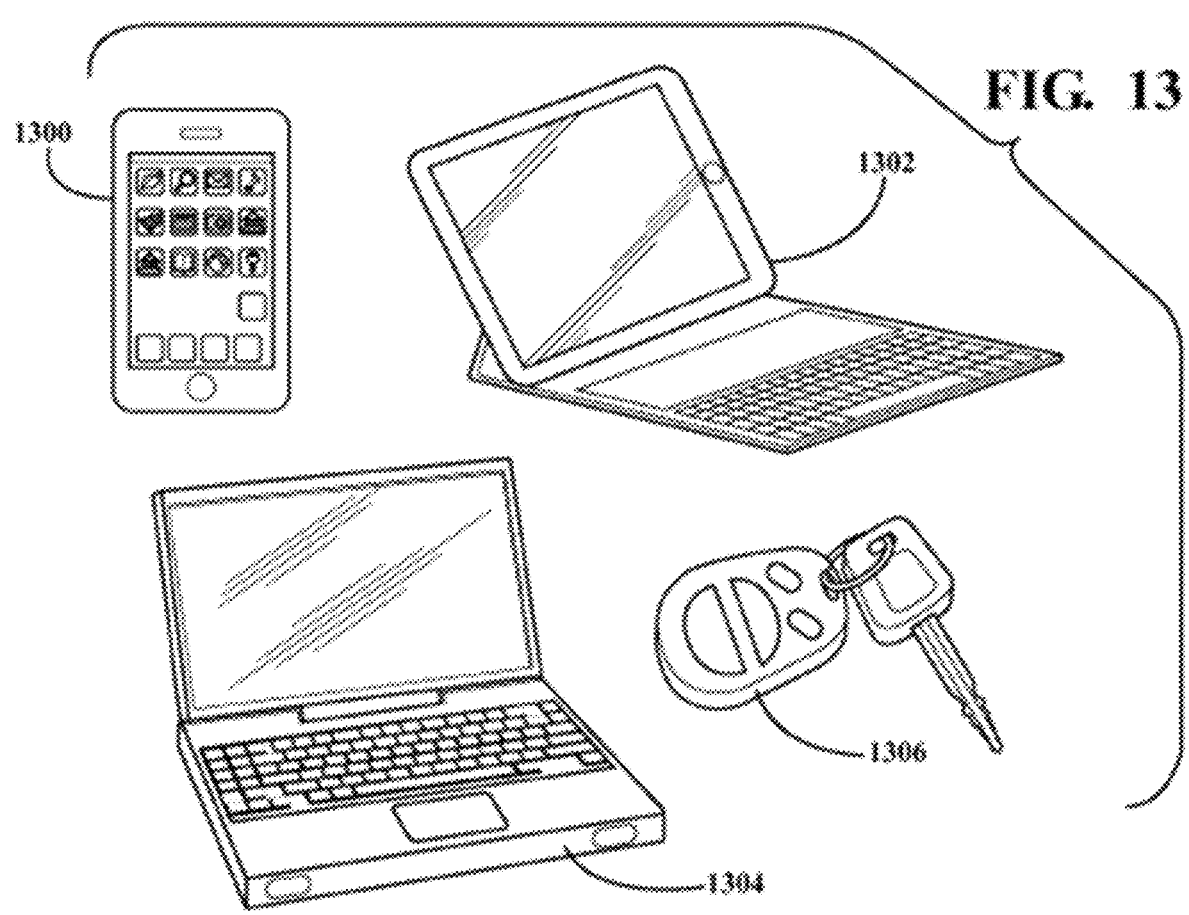
FIG. 13 illustrates exemplary Control Units for activating a nerve stimulation device.

Referring to FIG. 13, the controller is an electronics platform that is a smartphone 1300, tablet 1302, personal computer 1304, or dedicated module 1306 that hosts wireless communications capabilities, such as Near Field Communications, Bluetooth, or Wi-Fi technologies as enabled by the current set of communications chips, e.g. Broadcom BCM4334, TI WiLink 8 and others, and a wide range of protocol apps that can communicate with the TNSSs. There may be more than one controller, acting together. This may occur, for example, if the user has both a smartphone control app running, and a key fob controller in his/her pocket/purse.

TNSS protocol performs the functions of communications with the controller including transmitting and receiving of control and data signals, activation and control of the neural stimulation, data gathering from on board sensors, communications and coordination with other TNSSs, and data analysis. Typically the TNSS may receive commands from the controller, generate stimuli and apply these to the tissues, sense signals from the tissues, and transmit these to the controller. It may also analyze the signals sensed and use this information to modify the stimulation applied. In addition to communicating with the controller it may also communicate with other TNSSs using electrical or radio signals via a body area network.

Referring to FIG. 14, controller protocol executed and/or displayed on a smartphone 1400, tablet 1402 or other computing platform or mobile device, will perform the functions of communications with TNSS modules including transmitting and receiving of control and data signals, activation and control of the neuro modulation regimens, data gathering from on board sensors, communications and coordination with other controllers, and data analysis. In some cases local control of the neuro modulation regimens may be conducted by controller protocol without communications with the user.

FIG. 15 shows potential applications of electrical stimulation and sensing for the body, particularly for users who may suffer from paralysis or loss of sensation or altered reflexes such as spasticity or tremor due to neurological disorders and their complications, as well as users suffering from incontinence, pain, immobility and aging. Different example medical uses of the present system are discussed below.

Figure 16:
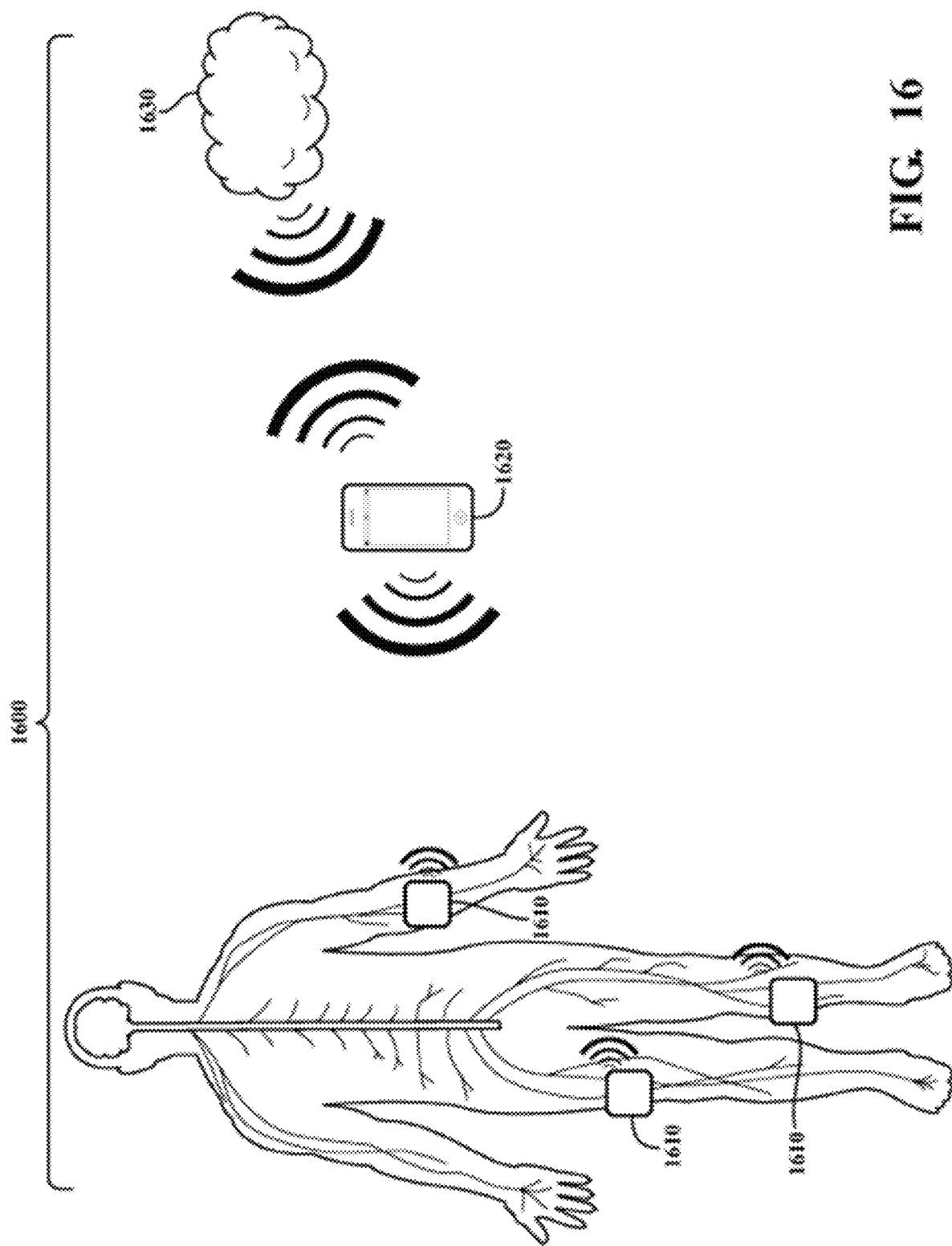
FIG. 16 shows an example TNSS system.

FIG. 16 shows the components of one example of a typical TNSS system 1600. TNSS devices 1610 are responsible for stimulation of nerves and for receiving data in the form of electrical, acoustic, imaging, chemical and other signals which then can be processed locally in the TNSS or passed to the Control Unit 1620. TNSS devices 1610 are also responsible for analysis and action. The TNSS device 1610 may contain a plurality of electrodes for stimulation and for sensing. The same electrodes may be used for both functions, but this is not required. The TNSS device 1610 may contain an imaging device, such as an ultrasonic transducer to create acoustic images of the structure beneath the electrodes or elsewhere in the body that may be affected by the neural stimulation.

In this example TNSS system, most of the data gathering and analysis is performed in the Control Unit 1620. The Control Unit 1620 may be a cellular telephone or a dedicated hardware device. The Control Unit 1620 runs an app that controls the local functions of the TNSS System 1600. The protocol app also communicates via the Internet or wireless networks 1630 with other TNSS systems and/or with 3rd party software applications.

Figure 17:
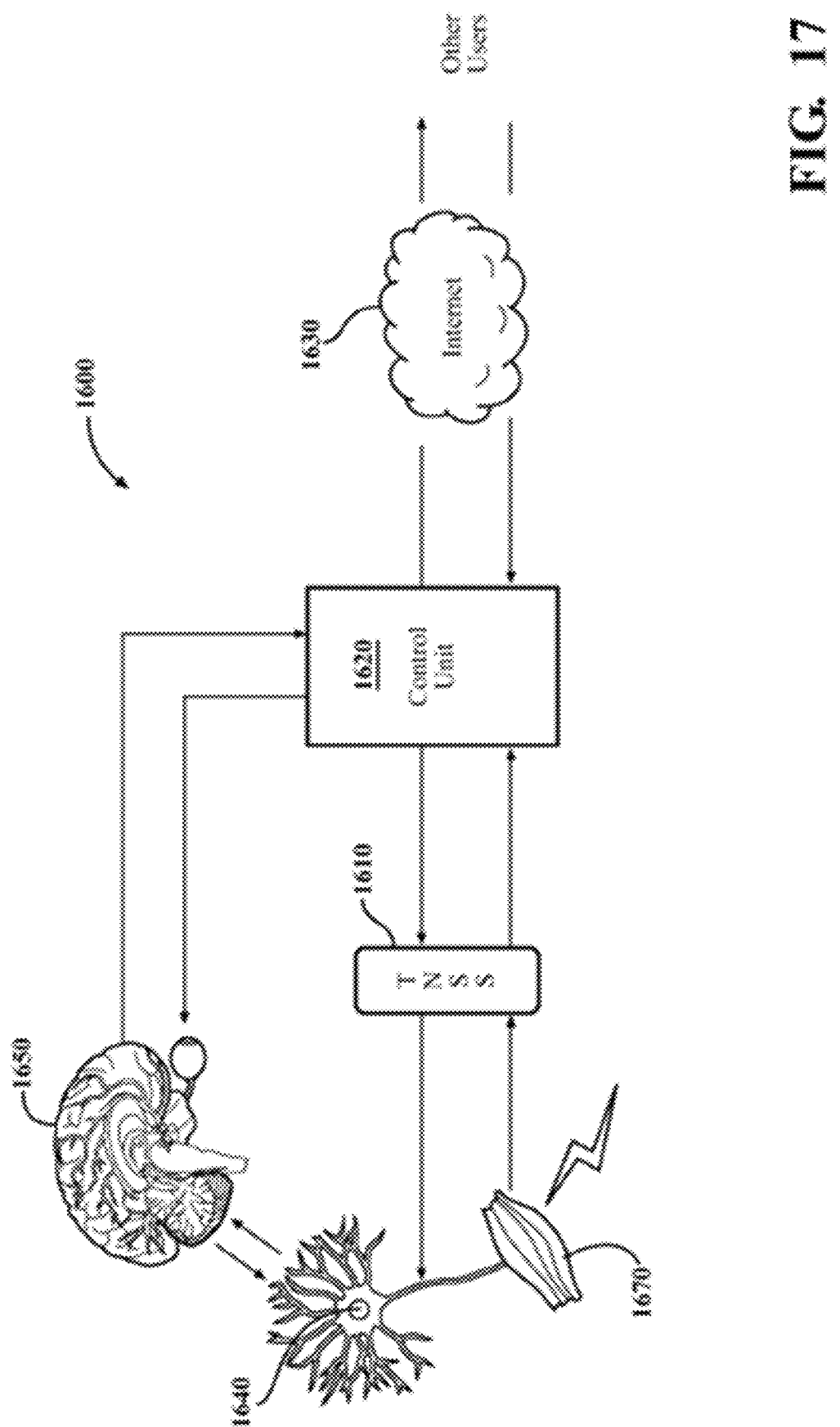
FIG. 17 shows communications among the components of the TNSS system of FIG. 16 and a user.

FIG. 17 shows the communications among the components of the TNSS system 1600 and the user. In this example, TNSS 1610 is capable of applying stimuli to nerves 1640 to produce action potentials in the nerves 1640 to produce actions in muscles 1670 or other organs such as the brain 1650. These actions may be sensed by the TNSS 1610, which may act on the information to modify the stimulation it provides. This closed loop constitutes the first level of the system 1600 in this example.

The TNSS 1610 may also be caused to operate by signals received from a Control Unit 1620 such as a cellphone, laptop, key fob, tablet, or other handheld device and may transmit information that it senses back to the Control Unit 1620. This constitutes the second level of the system 1600 in this example.

The Control Unit 1620 is caused to operate by commands from a user, who also receives information from the Control Unit 1620. The user may also receive information about actions of the body via natural senses such as vision or touch via sensory nerves and the spinal cord, and may in some cases cause actions in the body via natural pathways through the spinal cord to the muscles.

The Control Unit 1620 may also communicate information to other users, experts, or application programs via the Internet 1630, and receive information from them via the Internet 1630.

The user may choose to initiate or modify these processes, sometimes using protocol applications residing in the TNSS 1610, the Control Unit 1620, the Internet 1630, or wireless networks. This software may assist the user, for example by processing the stimulation to be delivered to the body to render it more selective or effective for the user, and/or by processing and displaying data received from the body or from the Internet 1630 or wireless networks to make it more intelligible or useful to the user.

Figure 18:
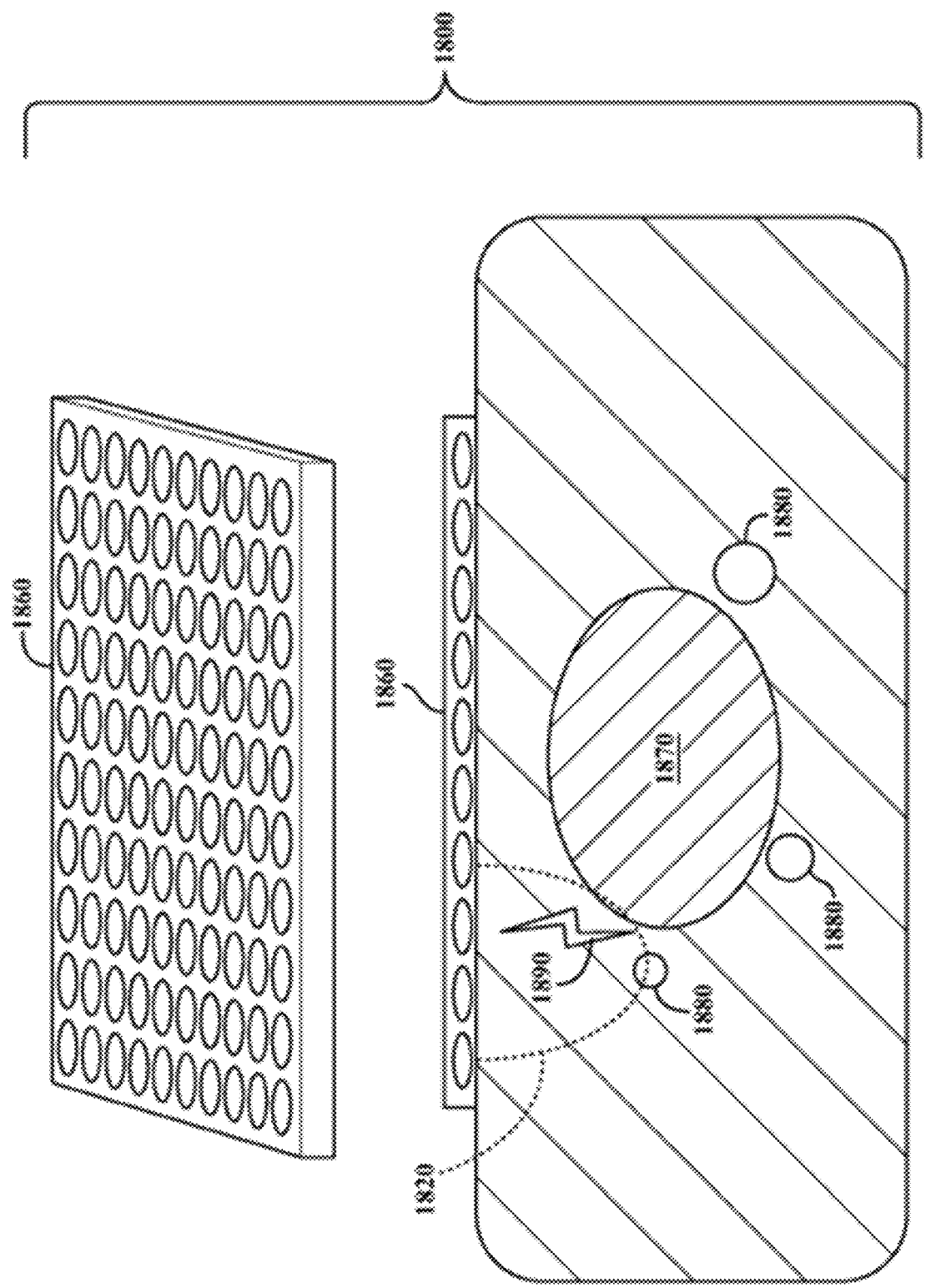
FIG. 18 shows an example electrode configuration for electric field steering and sensing.

FIG. 18 shows an example electrode configuration 1800 for Electric Field Steering. The application of an appropriate electric field to the body can cause a nerve to produce an electrical pulse known as an action potential. The shape of the electric field is influenced by the electrical properties of the different tissue through which it passes and the size, number and position of the electrodes used to apply it. The electrodes can therefore be designed to shape or steer or focus the electric field on some nerves more than on others, thereby providing more selective stimulation.

An example 10×10 matrix of electrical contacts 1860 is shown. By varying the pattern of electrical contacts 1860 employed to cause an electric field 1820 to form and by time varying the applied electrical power to this pattern of contacts 1860, it is possible to steer the field 1820 across different parts of the body, which may include muscle 1870, bone, fat, and other tissue, in three dimensions. This electric field 1820 can activate specific nerves or nerve bundles 1880 while sensing the electrical and mechanical actions produced 1890, and thereby enabling the TNSS to discover more effective or the most effective pattern of stimulation for producing the desired action.

Figure 19:
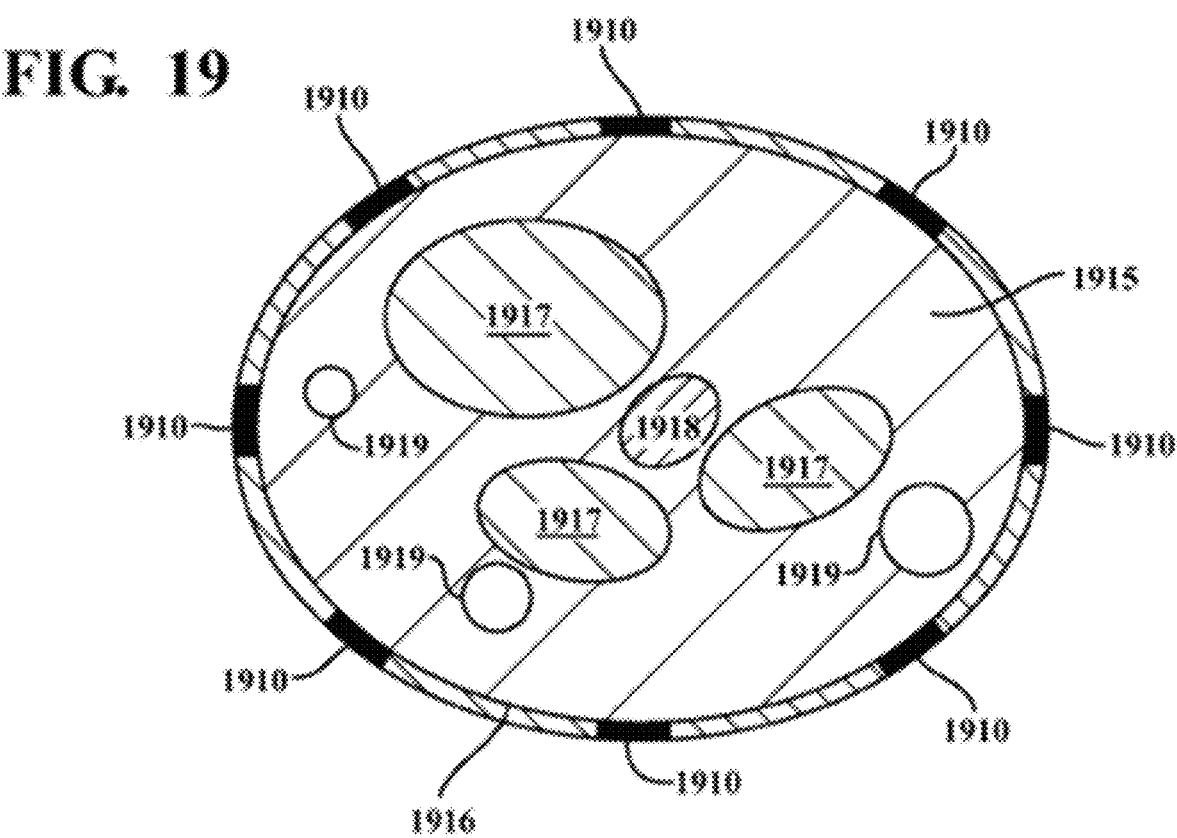
FIG. 19 shows an example of stimulating and sensing patterns of signals in a volume of tissue.

FIG. 19 shows an example of stimulating and sensing patterns of signals in a volume of tissue. Electrodes 1910 as part of a cuff arrangement are placed around limb 1915. The electrodes 1910 are external to a layer of skin 1916 on limb 1915. Internal components of the limb 1915 include muscle 1917, bone 1918, nerves 1919, and other tissues. By using electric field steering for stimulation, as described with reference to FIG. 18, the electrodes 1910 can activate nerves 1919 selectively. An array of sensors (e.g., piezoelectric sensors or micro-electro-mechanical sensors) in a TNSS can act as a phased array antenna for receiving ultrasound signals, to acquire ultrasonic images of body tissues. Electrodes 1910 may act as an array of electrodes sensing voltages at different times and locations on the surface of the body, with software processing this information to display information about the activity in body tissues, e.g., which muscles are activated by different patterns of stimulation.

The SBA's ability to stimulate and collect organic data has multiple applications including bladder control, reflex incontinence, sexual stimulations, pain control and wound healing among others. Examples of SBA's application for medical and other uses follow.

Medical Uses

Bladder Management

Overactive bladder: When the user feels a sensation of needing to empty the bladder urgently, he or she presses a button on the Controller to initiate stimulation via a Smart Band Aid™ applied over the dorsal nerve of the penis or clitoris. Activation of this nerve would inhibit the sensation of needing to empty the bladder urgently, and allow it to be emptied at a convenient time.

Incontinence: A person prone to incontinence of urine because of unwanted contraction of the bladder uses the SBA to activate the dorsal nerve of the penis or clitoris to inhibit contraction of the bladder and reduce incontinence of urine. The nerve could be activated continuously, or intermittently when the user became aware of the risk of incontinence, or in response to a sensor indicating the volume or pressure in the bladder.

Erection, ejaculation and orgasm: Stimulation of the nerves on the underside of the penis by a Smart Band Aid™ (electrical stimulation or mechanical vibration) can cause sexual arousal and might be used to produce or prolong erection and to produce orgasm and ejaculation.

Pain control: A person suffering from chronic pain from a particular region of the body applies a Smart Band Aid™ over that region and activates electrically the nerves conveying the sensation of touch, thereby reducing the sensation of pain from that region. This is based on the gate theory of pain.

Wound care: A person suffering from a chronic wound or ulcer applies a Smart Band Aid™ over the wound and applies electrical stimuli continuously to the tissues surrounding the wound to accelerate healing and reduce infection.

Essential tremor: A sensor on a Smart Band Aid™ detects the tremor and triggers neuro stimulation to the muscles and sensory nerves involved in the tremor with an appropriate frequency and phase relationship to the tremor. The stimulation frequency would typically be at the same frequency as the tremor but shifted in phase in order to cancel the tremor or reset the neural control system for hand position.

Reduction of spasticity: Electrical stimulation of peripheral nerves can reduce spasticity for several hours after stimulation. A Smart Band Aid™ operated by the patient when desired from a smartphone could provide this stimulation.

Restoration of sensation and sensory feedback: People who lack sensation, for example as a result of diabetes or stroke use a Smart Band Aid™ to sense movement or contact, for example of the foot striking the floor, and the SBA provides mechanical or electrical stimulation to another part of the body where the user has sensation, to improve safety or function. Mechanical stimulation is provided by the use of acoustic transducers in the SBA such as small vibrators. Applying a Smart Band Aid™ to the limb or other assistive device provides sensory feedback from artificial limbs. Sensory feedback can also be used to substitute one sense for another, e.g. touch in place of sight.

Recording of mechanical activity of the body: Sensors in a Smart Band Aid™ record position, location and orientation of a person or of body parts and transmit this data to a smartphone for the user and/or to other computer networks for safety monitoring, analysis of function and coordination of stimulation.

Recording of sound from the body or reflections of ultrasound waves generated by a transducer in a Smart Band Aid™ could provide information about body structure, e.g., bladder volume for persons unable to feel their bladder. Acoustic transducers may be piezoelectric devices or MEMS devices that transmit and receive the appropriate acoustic frequencies. Acoustic data may be processed to allow imaging of the interior of the body.

Recording of Electrical Activity of the Body

Electrocardiogram: Recording the electrical activity of the heart is widely used for diagnosing heart attacks and abnormal rhythms. It is sometimes necessary to record this activity for 24 hours or more to detect uncommon rhythms. A Smart Band Aid™ communicating wirelessly with a smartphone or computer network achieves this more simply than present systems.

Electromyogram: Recording the electrical activity of muscles is widely used for diagnosis in neurology and also used for movement analysis. Currently this requires the use of many needles or adhesive pads on the surface of the skin connected to recording equipment by many wires. Multiple Smart Band Aids™ record the electrical activity of many muscles and transmit this information wirelessly to a smartphone.

Recording of optical information from the body: A Smart Band Aid™ incorporating a light source (LED, laser) illuminates tissues and senses the characteristics of the reflected light to measure characteristics of value, e.g., oxygenation of the blood, and transmit this to a cellphone or other computer network.

Recording of chemical information from the body: The levels of chemicals or drugs in the body or body fluids is monitored continuously by a Smart Band Aid™ sensor and transmitted to other computer networks and appropriate feedback provided to the user or to medical staff. Levels of chemicals may be measured by optical methods (reflection of light at particular wavelengths) or by chemical sensors.

Special Populations of Disabled Users

There are many potential applications of electrical stimulation for therapy and restoration of function. However, few of these have been commercialized because of the lack of affordable convenient and easily controllable stimulation systems. Some applications are shown in the FIG. 15.

Limb Muscle stimulation: Lower limb muscles can be exercised by stimulating them electrically, even if they are paralyzed by stroke or spinal cord injury. This is often combined with the use of a stationary exercise cycle for stability. Smart Band Aid™ devices could be applied to the quadriceps muscle of the thigh to stimulate these, extending the knee for cycling, or to other muscles such as those of the calf. Sensors in the Smart Band Aid™ could trigger stimulation at the appropriate time during cycling, using an application on a smartphone, tablet, handheld hardware device such as a key fob, wearable computing device, laptop, or desktop computer, among other possible devices. Upper limb muscles can be exercised by stimulating them electrically, even if they are paralyzed by stroke of spinal cord injury. This is often combined with the use of an arm crank exercise machine for stability. Smart Band Aid™ devices are applied to multiple muscles in the upper limb and triggered by sensors in the Smart Band Aids™ at the appropriate times, using an application on a smartphone.

Prevention of osteoporosis: Exercise can prevent osteoporosis and pathological fractures of bones. This is applied using Smart Band Aids™ in conjunction with exercise machines such as rowing simulators, even for people with paralysis who are particularly prone to osteoporosis.

Prevention of deep vein thrombosis: Electric stimulation of the muscles of the calf can reduce the risk of deep vein thrombosis and potentially fatal pulmonary embolus. Electric stimulation of the calf muscles is applied by a Smart Band Aid™ with stimulation programmed from a smartphone, e.g., during a surgical operation, or on a preset schedule during a long plane flight.

Restoration of Function (Functional Electrical Stimulation) Lower Limb

1) Foot drop: People with stroke often cannot lift their forefoot and drag their toes on the ground. A Smart Band Aid™ is be applied just below the knee over the common peroneal nerve to stimulate the muscles that lift the forefoot at the appropriate time in the gait cycle, triggered by a sensor in the Smart Band Aid™.

2) Standing: People with spinal cord injury or some other paralyses can be aided to stand by electrical stimulation of the quadriceps muscles of their thigh. These muscles are stimulated by Smart Band Aids™ applied to the front of the thigh and triggered by sensors or buttons operated by the patient using an application on a smartphone. This may also assist patients to use lower limb muscles when transferring from a bed to a chair or other surface.

3) Walking: Patients with paralysis from spinal cord injury are aided to take simple steps using electrical stimulation of the lower limb muscles and nerves. Stimulation of the sensory nerves in the common peroneal nerve below the knee can cause a triple reflex withdrawal, flexing the ankle, knee and hip to lift the leg, and then stimulation of the quadriceps can extend the knee to bear weight. The process is then repeated on the other leg. Smart Band Aids™ coordinated by an application in a smartphone produce these actions.

Upper Limb

Hand grasp: People with paralysis from stroke or spinal cord injury have simple hand grasp restored by electrical stimulation of the muscles to open or close the hand. This is produced by Smart Band Aids™ applied to the back and front of the forearm and coordinated by sensors in the Smart Band Aids™ and an application in a smartphone.

Reaching: Patients with paralysis from spinal cord injury sometimes cannot extend their elbow to reach above the head. Application of a Smart Band Aid™ to the triceps muscle stimulates this muscle to extend the elbow. This is triggered by a sensor in the Smart Band Aid™ detecting arm movements and coordinating it with an application on a smartphone.

Posture: People whose trunk muscles are paralyzed may have difficulty maintaining their posture even in a wheelchair. They may fall forward unless they wear a seatbelt, and if they lean forward they may be unable to regain upright posture. Electrical stimulation of the muscles of the lower back using a Smart Band Aid™ allows them to maintain and regain upright posture. Sensors in the Smart Band Aid™ trigger this stimulation when a change in posture was detected.

Coughing: People whose abdominal muscles are paralyzed cannot produce a strong cough and are at risk for pneumonia. Stimulation of the muscles of the abdominal wall using a Smart Band Aid™ could produce a more forceful cough and prevent chest infections. The patient using a sensor in a Smart Band Aid™ triggers the stimulation.

Essential Tremor: It has been demonstrated that neuro stimulation can reduce or eliminate the signs of ET. ET may be controlled using a TNSS. A sensor on a Smart Band Aid™ detects the tremor and trigger neuro stimulation to the muscles and sensory nerves involved in the tremor with an appropriate frequency and phase relationship to the tremor. The stimulation frequency is typically be at the same frequency as the tremor but shifted in phase in order to cancel the tremor or reset the neural control system for hand position.

Non-Medical Applications

Sports Training

Sensing the position and orientation of multiple limb segments is used to provide visual feedback on a smartphone of, for example, a golf swing, and also mechanical or electrical feedback to the user at particular times during the swing to show them how to change their actions. The electromyogram of muscles could also be recorded from one or many Smart Band Aids™ and used for more detailed analysis.

Gaming

Sensing the position and orientation of arms, legs and the rest of the body produces a picture of an onscreen player that can interact with other players anywhere on the Internet. Tactile feedback would be provided to players by actuators in Smart Band Aids on various parts of the body to give the sensation of striking a ball, etc.

Motion Capture for Film and Animation

Wireless TNSS capture position, acceleration, and orientation of multiple parts of the body. This data may be used for animation of a human or mammal and has application for human factor analysis and design.

Sample Modes of Operation

An SBA system consists of at least a single Controller and a single SBA. Following application of the SBA to the user's skin, the user controls it via the Controller's app using Near Field Communications. The app appears on a smartphone screen and can be touch controlled by the user; for 'key fob' type Controllers. The SBA is controlled by pressing buttons on the key fob.

When the user feels the need to activate the SBA s/he presses the "go" button two or more times to prevent false triggering, thus delivering the neuro stimulation. The neuro stimulation may be delivered in a variety of patterns of frequency, duration, and strength and may continue until a button is pressed by the user or may be delivered for a length of time set in the application.

Sensor capabilities in the TNSS, are enabled to start collecting/analyzing data and communicating with the controller when activated.

The level of functionality in the protocol app, and the protocol embedded in the TNSS, will depend upon the neuro modulation or neuro stimulation regimen being employed.

In some cases there will be multiple TNSSs employed for the neuro modulation or neuro stimulation regimen. The basic activation will be the same for each TNSS.

However, once activated multiple TNSSs will automatically form a network of neuro modulation/stimulation points with communications enabled with the controller.

The need for multiple TNSSs arises from the fact that treatment regimens may need several points of access to be effective.

Controlling the Stimulation

In general, advantages of a wireless TNSS system as disclosed herein over existing transcutaneous electrical nerve stimulation devices include: (1) fine control of all stimulation parameters from a remote device such as a smartphone, either directly by the user or by stored programs; (2) multiple electrodes of a TNSS can form an array to shape an electric field in the tissues; (3) multiple TNSS devices can form an array to shape an electric field in the tissues; (4) multiple TNSS devices can stimulate multiple structures, coordinated by a smartphone; (5) selective stimulation of nerves and other structures at different locations and depths in a volume of tissue; (6) mechanical, acoustic or optical stimulation in addition to electrical stimulation; (7) the transmitting antenna of TNSS device can focus a beam of electromagnetic energy within tissues in short bursts to activate nerves directly without implanted devices; (8) inclusion of multiple sensors of multiple modalities, including but not limited to position, orientation, force, distance, acceleration, pressure, temperature, voltage, light and other electromagnetic radiation, sound, ions or chemical compounds, making it possible to sense electrical activities of muscles (EMG, EKG), mechanical effects of muscle contraction, chemical composition of body fluids, location or dimensions or shape of an organ or tissue by transmission and receiving of ultrasound.

Further advantages of the wireless TNSS system include: (1) TNSS devices are expected to have service lifetimes of days to weeks and their disposability places less demand on power sources and battery requirements; (2) the combination of stimulation with feedback from artificial or natural sensors for closed loop control of muscle contraction and force, position or orientation of parts of the body, pressure within organs, and concentrations of ions and chemical compounds in the tissues; (3) multiple TNSS devices can form a network with each other, with remote controllers, with other devices, with the Internet and with other users; (4) a collection of large amounts of data from one or many TNSS devices and one or many users regarding sensing and stimulation, collected and stored locally or through the internet; (5) analysis of large amounts of data to detect patterns of sensing and stimulation, apply machine learning, and improve algorithms and functions; (6) creation of databases and knowledge bases of value; (7) convenience, including the absence of wires to become entangled in clothing, showerproof and sweat proof, low profile, flexible, camouflaged or skin colored, (8) integrated power, communications, sensing and stimulating inexpensive disposable TNSS, consumable electronics; (9) power management that utilizes both hardware and software functions will be critical to the convenience factor and widespread deployment of TNSS device.

Referring again to FIG. 1, a nerve cell normally has a voltage across the cell membrane of 70 millivolts with the interior of the cell at a negative voltage with respect to the exterior of the cell. This is known as the resting potential and it is normally maintained by metabolic reactions which maintain different concentrations of electrical ions in the inside of the cell compared to the outside. Ions can be actively "pumped" across the cell membrane through ion channels in the membrane that are selective for different types of ion, such as sodium and potassium. The channels are voltage sensitive and can be opened or closed depending on the voltage across the membrane. An electric field produced within the tissues by a stimulator can change the normal resting voltage across the membrane, either increasing or decreasing the voltage from its resting voltage.

Referring again to FIG. 2, a decrease in voltage across the cell membrane to about 55 millivolts opens certain ion channels, allowing ions to flow through the membrane in a self-catalyzing but self-limited process which results in a transient decrease of the trans membrane potential to zero, and even positive, known as depolarization followed by a rapid restoration of the resting potential as a result of active pumping of ions across the membrane to restore the resting situation which is known as repolarization. This transient change of voltage is known as an action potential and it typically spreads over the entire surface of the cell. If the shape of the cell is such that it has a long extension known as an axon, the action potential spreads along the length of the axon. Axons that have insulating myelin sheaths propagate action potentials at much higher speeds than those axons without myelin sheaths or with damaged myelin sheaths.

If the action potential reaches a junction, known as a synapse, with another nerve cell, the transient change in membrane voltage results in the release of chemicals known as neuro-transmitters that can initiate an action potential in the other cell. This provides a means of rapid electrical communication between cells, analogous to passing a digital pulse from one cell to another.

If the action potential reaches a synapse with a muscle cell it can initiate an action potential that spreads over the surface of the muscle cell. This voltage change across the membrane of the muscle cell opens ion channels in the membrane that allow ions such as sodium, potassium and calcium to flow across the membrane, and can result in contraction of the muscle cell.

Increasing the voltage across the membrane of a cell below −70 millivolts is known as hyper-polarization and reduces the probability of an action potential being generated in the cell. This can be useful for reducing nerve activity and thereby reducing unwanted symptoms such as pain and spasticity The voltage across the membrane of a cell can be changed by creating an electric field in the tissues with a stimulator. It is important to note that action potentials are created within the mammalian nervous system by the brain, the sensory nervous system or other internal means. These action potentials travel along the body's nerve "highways". The TNSS creates an action potential through an externally applied electric field from outside the body. This is very different than how action potentials are naturally created within the body.

Electric Fields that can Cause Action Potentials

Referring to FIG. 2, electric fields capable of causing action potentials can be generated by electronic stimulators connected to electrodes that are implanted surgically in close proximity to the target nerves. To avoid the many issues associated with implanted devices, it is desirable to generate the required electric fields by electronic devices located on the surface of the skin. Such devices typically use square wave pulse trains of the form shown in FIG. 20. Such devices may be used instead of implants and/or with implants such as reflectors, conductors, refractors, or markers for tagging target nerves and the like, so as to shape electric fields to enhance nerve targeting and/or selectivity.

Figure 20:
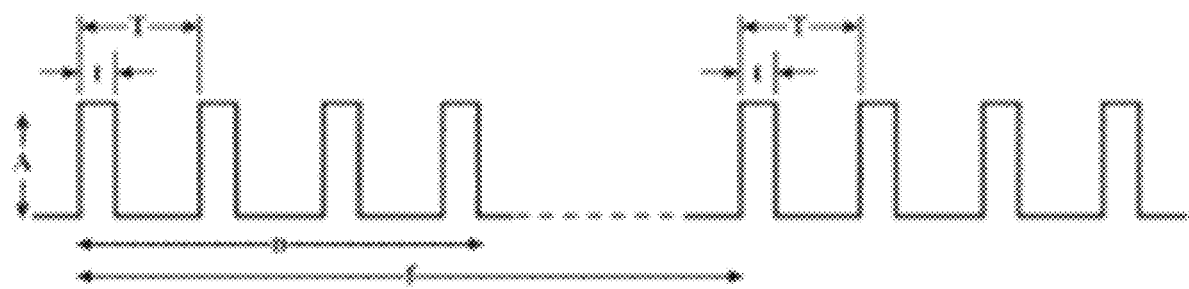
FIG. 20 is a graph showing pulses applied to the skin.
Figure 21:
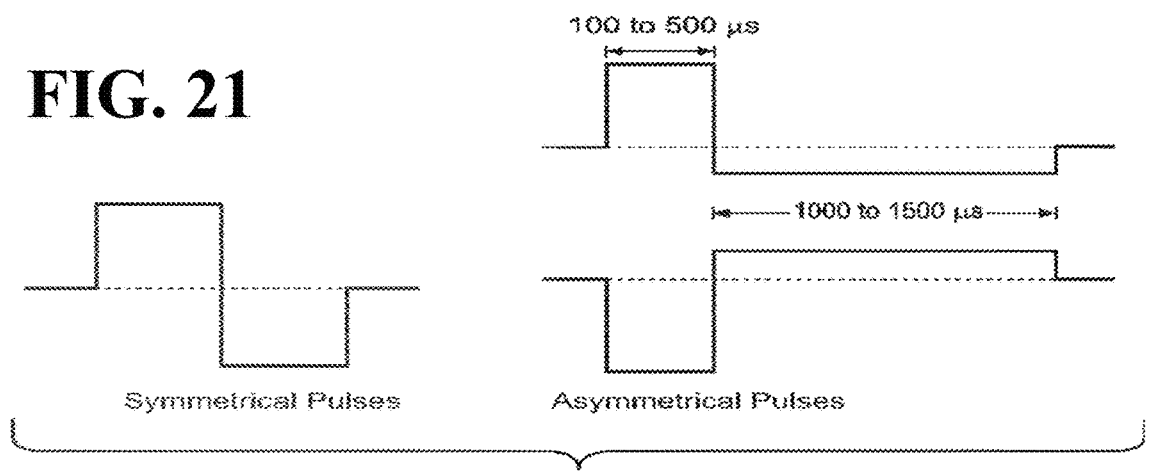
FIG. 21 is a graph showing symmetrical and asymmetrical pulses applied to the skin.

Referring to FIG. 20, the amplitude of the pulses "A", applied to the skin, may vary between 1 and 100 Volts, pulse width "t", between 100 microseconds and 10 milliseconds, duty cycle (t/T) between 0.1% and 50%, the frequency of the pulses within a group between 1 and 100/sec, and the number of pulses per group "n", between 1 and several hundred. Typically, pulses applied to the skin will have an amplitude of up to 60 volts, a pulse width of 250 microseconds and a frequency of 20 per second, resulting in a duty cycle of 0.5%. In some cases balanced-charge biphasic pulses will be used to avoid net current flow. Referring to FIG. 21, these pulses may be symmetrical, with the shape of the first part of the pulse similar to that of the second part of the pulse, or asymmetrical, in which the second part of the pulse has lower amplitude and a longer pulse width in order to avoid canceling the stimulatory effect of the first part of the pulse.

Formation of Electric Fields by Stimulators

The location and magnitude of the electric potential applied to the tissues by electrodes provides a method of shaping the electrical field. For example, applying two electrodes to the skin, one at a positive electrical potential with respect to the other, can produce a field in the underlying tissues such as that shown in the cross-sectional diagram of FIG. 22.

Figure 22:
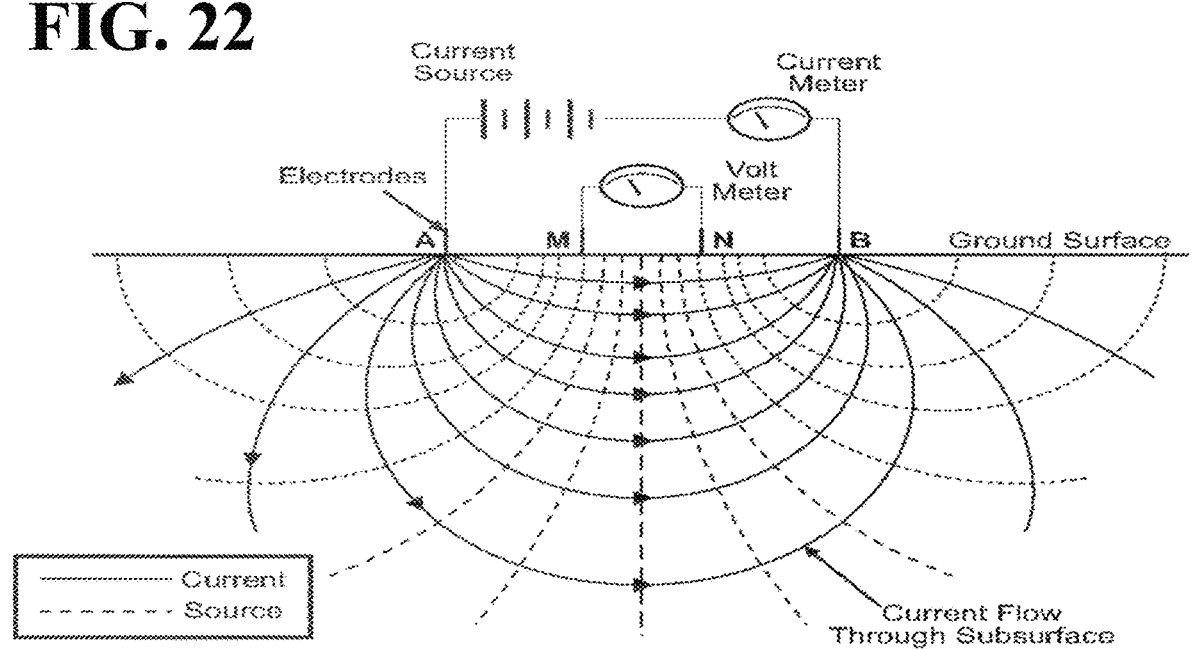
FIG. 22 is a cross-sectional diagram showing a field in underlying tissue produced by application of two electrodes to the skin.

The diagram in FIG. 22 assumes homogeneous tissue. The voltage gradient is highest close to the electrodes and lower at a distance from the electrodes. Nerves are more likely to be activated close to the electrodes than at a distance. For a given voltage gradient, nerves of large diameter are more likely to be activated than nerves of smaller diameter. Nerves whose long axis is aligned with the voltage gradient are more likely to be activated than nerves whose long axis is at right angles to the voltage gradient.

Figure 23:
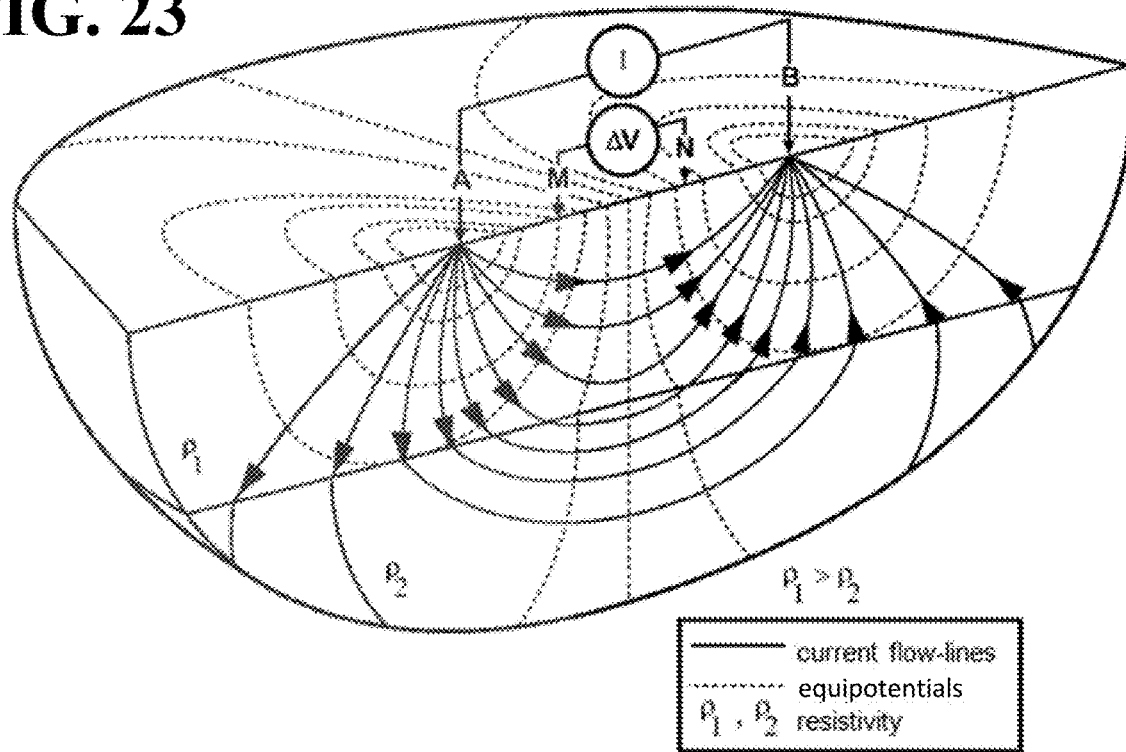
FIG. 23 is a cross-sectional diagram showing a field in underlying tissue produced by application of two electrodes to the skin, with two layers of tissue of different electrical resistivity.

Applying similar electrodes to a part of the body in which there are two layers of tissue of different electrical resistivity, such as fat and muscle, can produce a field such as that shown in FIG. 23. Layers of different tissue may act to refract and direct energy waves and be used for beam aiming and steering. An individual's tissue parameters may be measured and used to characterize the appropriate energy stimulation for a selected nerve.

Figure 24:
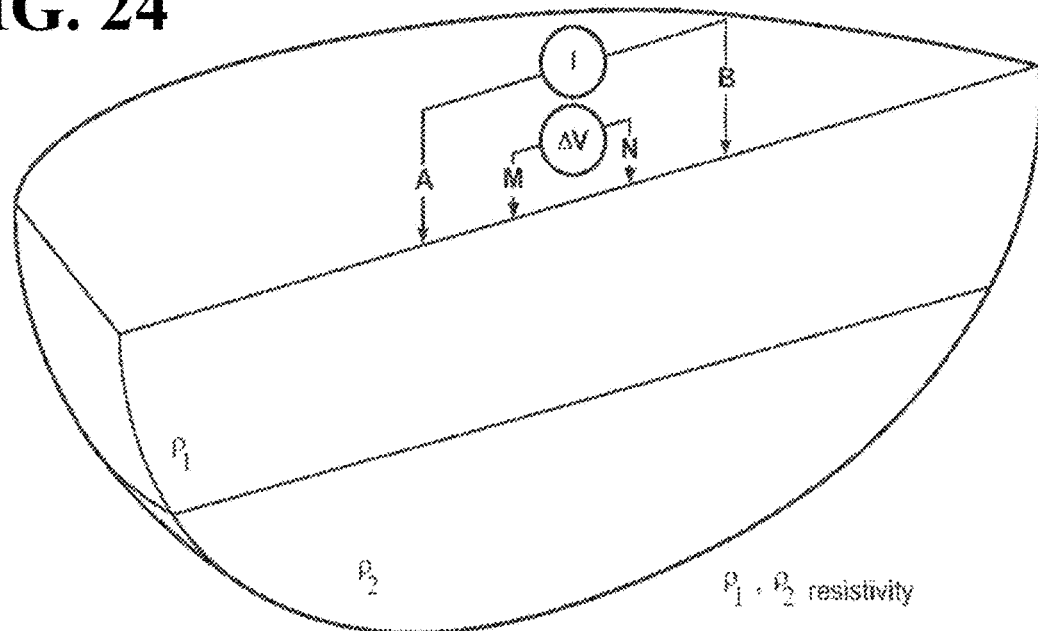
FIG. 24 is a cross-sectional diagram showing a field in underlying tissue when the stimulating pulse is turned off.

Referring to FIG. 24, when the stimulating pulse is turned off the electric field will collapse and the fields will be absent as shown. It is the change in electric field that will cause an action potential to be created in a nerve cell, provided sufficient voltage and the correct orientation of the electric field occurs. More complex three-dimensional arrangements of tissues with different electrical properties can result in more complex three-dimensional electric fields, particularly since tissues have different electrical properties and these properties are different along the length of a tissue and across it, as shown in Table 1.

TABLE 1

| Electrical Conductivity (siemens/m) | Direction | Average |
|---|---|---|
| Blood | | .65 |
| Bone | Along | .17 |
| Bone | Mixed | .095 |
| Fat | | .05 |
| Muscle | Along | .127 |
| Muscle | Across | .45 |
| Muscle | Mixed | .286 |
| Skin (Dry) | | .000125 |
| Skin (Wet) | | .00121 |

Modification of Electric Fields by Tissue

An important factor in the formation of electric fields used to create action potentials in nerve cells is the medium through which the electric fields must penetrate. For the human body this medium includes various types of tissue including bone, fat, muscle, and skin. Each of these tissues possesses different electrical resistivity or conductivity and different capacitance and these properties are anisotropic. They are not uniform in all directions within the tissues. For example, an axon has lower electrical resistivity along its axis than perpendicular to its axis. The wide range of conductivities is shown in Table 1. The three-dimensional structure and resistivity of the tissues will therefore affect the orientation and magnitude of the electric field at any given point in the body.

Modification of Electric Fields by Multiple Electrodes

Applying a larger number of electrodes to the skin can also produce more complex three-dimensional electrical fields that can be shaped by the location of the electrodes and the potential applied to each of them. Referring to FIG. 20, the pulse trains can differ from one another indicated by A, t/T, n, and f as well as have different phase relationships between the pulse trains. For example with an 8×8 array of electrodes, combinations of electrodes can be utilized ranging from simple dipoles, to quadripoles, to linear arrangements, to approximately circular configurations, to produce desired electric fields within tissues.

Applying multiple electrodes to a part of the body with complex tissue geometry will thus result in an electric field of a complex shape. The interaction of electrode arrangement and tissue geometry can be modeled using Finite Element Modeling, which is a mathematical method of dividing the tissues into many small elements in order to calculate the shape of a complex electric field. This can be used to design an electric field of a desired shape and orientation to a particular nerve.

High frequency techniques known for modifying an electric field, such as the relation between phases of a beam, cancelling and reinforcing by using phase shifts, may not apply to application of electric fields by TNSSs because they use low frequencies. Instead, examples use beam selection to move or shift or shape an electric field, also described as field steering or field shaping, by activating different electrodes, such as from an array of electrodes, to move the field. Selecting different combinations of electrodes from an array may result in beam or field steering. A particular combination of electrodes may shape a beam and/or change the direction of a beam by steering. This may shape the electric field to reach a target nerve selected for stimulation.

Activation of Nerves by Electric Fields

Typically, selectivity in activating nerves has required electrodes to be implanted surgically on or near nerves. Using electrodes on the surface of the skin to focus activation selectively on nerves deep in the tissues, as with examples of the invention, has many advantages. These include avoidance of surgery, avoidance of the cost of developing complex implants and gaining regulatory approval for them, and avoidance of the risks of long-term implants.

The features of the electric field that determine whether a nerve will be activated to produce an action potential can be modeled mathematically by the "Activating Function" disclosed in Rattay F., "The basic mechanism for the electrical stimulation of the nervous system", *Neuroscience* Vol. 89, No. 2, pp. 335-346 (1999). The electric field can produce a voltage, or extracellular potential, within the tissues that varies along the length of a nerve. If the voltage is proportional to distance along the nerve, the first order spatial derivative will be constant and the second order spatial derivative will be zero. If the voltage is not proportional to distance along the nerve, the first order spatial derivative will not be constant and the second order spatial derivative will not be zero. The Activating Function is proportional to the second-order spatial derivative of the extracellular potential along the nerve. If it is sufficiently greater than zero at a given point it predicts whether the electric field will produce an action potential in the nerve at that point. This prediction may be input to a nerve signature.

In practice, this means that electric fields that are varying sufficiently greatly in space or time can produce action potentials in nerves. These action potentials are also most likely to be produced where the orientation of the nerves to the fields change, either because the nerve or the field changes direction. The direction of the nerve can be determined from anatomical studies and imaging studies such as MRI scans. The direction of the field can be determined by the positions and configurations of electrodes and the voltages applied to them, together with the electrical properties of the tissues. As a result, it is possible to activate certain nerves at certain tissue locations selectively while not activating others.

To accurately control an organ or muscle, the nerve to be activated must be accurately selected. This selectivity may be improved by using examples disclosed herein as a nerve signature, in several ways, as follows:

(1) Improved algorithms to control the effects when a nerve is stimulated, for example, by measuring the resulting electrical or mechanical activity of muscles and feeding back this information to modify the stimulation and measuring the effects again. Repeated iterations of this process can result in optimizing the selectivity of the stimulation, either by classical closed loop control or by machine learning techniques such as pattern recognition and artificial intelligence;

(2) Improving nerve selectivity by labeling or tagging nerves chemically; for example, introduction of genes into some nerves to render them responsive to light or other electromagnetic radiation can result in the ability to activate these nerves and not others when light or electromagnetic radiation is applied from outside the body;

(3) Improving nerve selectivity by the use of electrical conductors to focus an electric field on a nerve; these conductors might be implanted, but could be passive and much simpler than the active implantable medical devices currently used;

(4) The use of reflectors or refractors, either outside or inside the body, is used to focus a beam of electromagnetic radiation on a nerve to improve nerve selectivity. If these reflectors or refractors are implanted, they may be passive and much simpler than the active implantable medical devices currently used;

(5) Improving nerve selectivity by the use of feedback from the person upon whom the stimulation is being performed; this may be an action taken by the person in response to a physical indication such as a muscle activation or a feeling from one or more nerve activations;

(6) Improving nerve selectivity by the use of feedback from sensors associated with the TNSS, or separately from other sensors, that monitor electrical activity associated with the stimulation; and (7) Improving nerve selectivity by the combination of feedback from both the person or sensors and the TNSS that may be used to create a unique profile of the user's nerve physiology for selected nerve stimulation.

Potential applications of electrical stimulation to the body, as previously disclosed, are shown in FIG. 15.

Figure 25A:
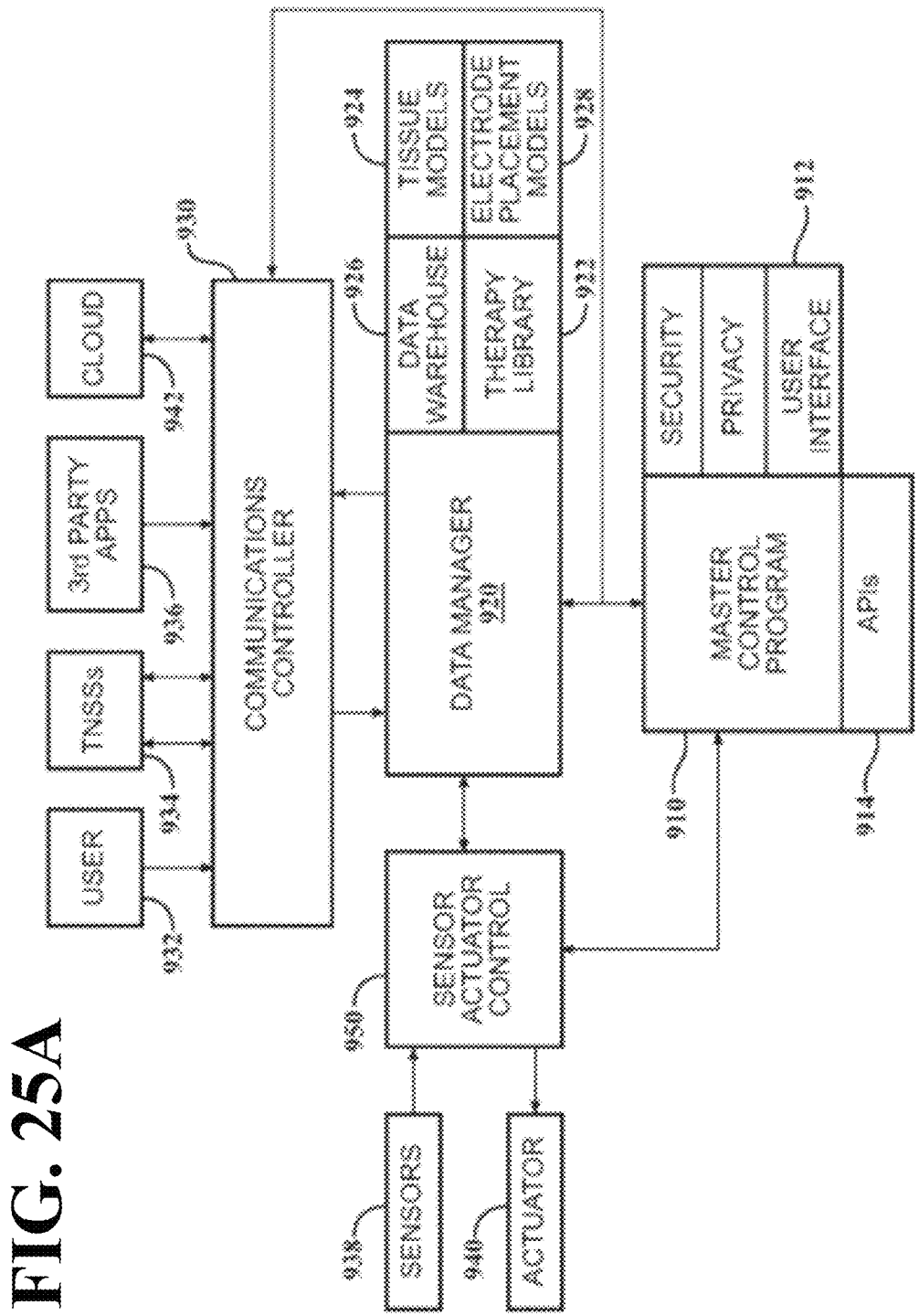
FIG. 25A is a system diagram of an example software and hardware components showing an example of a Topical Nerve Stimulator/Sensor (TNSS) interpreting a data stream from a control device in accordance with one example.

Referring to FIG. 25A, a TNSS 934 human and mammalian interface and its method of operation and supporting system are managed by a Master Control Program ("MCP") 910 represented in function format as block diagrams. It provides the logic for the nerve stimulator system in accordance to one example.

In one example, MCP 910 and other components shown in FIG. 25A are implemented by one or more processors that are executing instructions. The processor may be any type of general or specific purpose processor. Memory is included for storing information and instructions to be executed by the processor. The memory can be comprised of any combination of random access memory ("RAM"), read only memory ("ROM"), static storage such as a magnetic or optical disk, or any other type of computer readable media.

Master Control Program

The primary responsibility of MCP 910 is to coordinate the activities and communications among the various control programs, a Data Manager 920, a User 932, and the external ecosystem and to execute the appropriate response algorithms in each situation. The MCP 910 accomplishes electric field shaping and/or beam steering by providing an electrode activation pattern to TNSS device 934 to selectively stimulate a target nerve. For example, upon notification by a Communications Controller 930 of an external event or request, the MCP 910 is responsible for executing the appropriate response, and working with the Data Manager 920 to formulate the correct response and actions. It integrates data from various sources such as Sensors 938 and external inputs such as TNSS devices 934, and applies the correct security and privacy policies, such as encryption and HIPAA required protocols. It will also manage the User Interface (UI) 912 and the various Application Program Interfaces (APIs) 914 that provide access to external programs.

MCP 910 is also responsible for effectively managing power consumption by TNSS device 934 through a combination of software algorithms and hardware components that may include, among other things: computing, communications, and stimulating electronics, antenna, electrodes, sensors, and power sources in the form of conventional or printed batteries.

Communications Controller

Communications controller 930 is responsible for receiving inputs from the User 932, from a plurality of TNSS devices 934, and from 3rd party apps 936 via communications sources such as the Internet or cellular networks. The format of such inputs will vary by source and must be received, consolidated, possibly reformatted, and packaged for the Data Manager 920.

User inputs may include simple requests for activation of TNSS devices 934 to status and information concerning the User's 932 situation or needs. TNSS devices 934 will provide signaling data that may include voltage readings, TNSS 934 status data, responses to control program inquiries, and other signals. Communications Controller 930 is also responsible for sending data and control requests to the plurality of TNSS devices 934. 3rd party applications 936 can send data, requests, or instructions for the Master Control Program 910 or User 932 via the Internet or cellular networks. Communications Controller 930 is also responsible for communications via the cloud where various software applications may reside.

In one example, a user can control one or more TNSS devices using a remote fob or other type of remote device and a communications protocol such as Bluetooth. In one example, a mobile phone is also in communication and functions as a central device while the fob and TNSS device function as peripheral devices. In another example, the TNSS device functions as the central device and the fob is a peripheral device that communicates directly with the TNSS device (i.e., a mobile phone or other device is not needed).

Data Manager

The Data Manager (DM) 920 has primary responsibility for the storage and movement of data to and from the Communications Controller 930, Sensors 938, Actuators 940, and the Master Control Program 910. The DM 920 has the capability to analyze and correlate any of the data under its control. It provides logic to select and activate nerves. Examples of such operations upon the data include: statistical analysis and trend identification; machine learning algorithms; signature analysis and pattern recognition, correlations among the data within the Data Warehouse 926, the Therapy Library 922, the Tissue Models 924, and the Electrode Placement Models 928, and other operations. There are several components to the data that is under its control as disclosed below.

The Data Warehouse (DW) 926 is where incoming data is stored; examples of this data can be real-time measurements from TNSS devices 934 or from Sensors (938), data streams from the Internet, or control and instructional data from various sources. The DM 920 will analyze data, as described above, that is held in the DW 926 and cause actions, including the export of data, under MCP 910 control. Certain decision making processes implemented by the DM 920 will identify data patterns both in time, frequency, and spatial domains and store them as signatures for reference by other programs. Techniques such as EMG, or multi-electrode EMG, gather a large amount of data that is the sum of hundreds to thousands of individual motor units and the typical procedure is to perform complex decomposition analysis on the total signal to attempt to tease out individual motor units and their behavior. The DM 920 will perform big data analysis over the total signal and recognize patterns that relate to specific actions or even individual nerves or motor units. This analysis can be performed over data gathered in time from an individual, or over a population of TNSS Users.

The Therapy Library 922 contains various control regimens for the TNSS devices 934. Regimens specify the parameters and patterns of pulses to be applied by the TNSS devices 934. The width and amplitude of individual pulses may be specified to stimulate nerve axons of a particular size selectively without stimulating nerve axons of other sizes. The frequency of pulses applied may be specified to modulate some reflexes selectively without modulating other reflexes. There are preset regimens that may be loaded from the Cloud 942 or 3rd party apps 936. The regimens may be static read-only as well as adaptive with read-write capabilities so they can be modified in real-time responding to control signals or feedback signals or software updates. Referring to FIG. 3, one such example of a regimen has parameters A=40 volts, t=500 microseconds, T=1 Millisecond, n=100 pulses per group, and f=20 per second. Other examples of regimens will vary the parameters within ranges previously specified.

The Tissue Models 924 is specific to the electrical properties of particular body locations where TNSS devices 934 may be placed. As previously disclosed, electric fields for production of action potentials will be affected by the different electrical properties of the various tissues that they encounter. Tissue Models 924 are combined with regimens from the Therapy Library 922 and Electrode Placement Models 928 to produce desired actions. Tissue Models 924 may be developed by MRI, Ultrasound or other imaging or measurement of tissue of a body or particular part of a body. This may be accomplished for a particular User 932 and/or based upon a body norm. One such example of a desired action is the use of a Tissue Model 924 together with a particular Electrode Placement Model 928 to determine how to focus the electric field from electrodes on the surface of the body on a specific deep location corresponding to the pudendal nerve in order to stimulate that nerve selectively to reduce incontinence of urine. Other examples of desired actions may occur when a Tissue Model 924 in combination with regimens from the Therapy Library 22 and Electrode Placement Models 928 produce an electric field that stimulates a sacral nerve. Many other examples of desired actions follow for the stimulation of other nerves.

Electrode Placement Models 928 specify electrode configurations that the TNSS devices 934 may apply and activate in particular locations of the body. For example, a TNSS device 934 may have multiple electrodes and the Electrode Placement Model 928 specifies where these electrodes should be placed on the body and which of these electrodes should be active in order to stimulate a specific structure selectively without stimulating other structures, or to focus an electric field on a deep structure. An example of an electrode configuration is a 4 by 4 set of electrodes within a larger array of multiple electrodes, such as an 8 by 8 array. This 4 by 4 set of electrodes may be specified anywhere within the larger array such as the upper right corner of the 8 by 8 array. Other examples of electrode configurations may be circular electrodes that may even include concentric circular electrodes. The TNSS device 934 may contain a wide range of multiple electrodes of which the Electrode Placement Models 928 will specify which subset will be activated. The Electrode Placement Models 928 complement the regimens in the Therapy Library 922 and the Tissue Models 924 and are used together with these other data components to control the electric fields and their interactions with nerves, muscles, tissues and other organs. Other examples may include TNSS devices 934 having merely one or two electrodes, such as but not limited to those utilizing a closed circuit.

Sensor/Actuator Control

Independent sensors 938 and actuators 940 can be part of the TNSS system. Its functions can complement the electrical stimulation and electrical feedback that the TNSS devices 934 provide. An example of such a sensor 938 and actuator 940 include, but are not limited to, an ultrasonic actuator and an ultrasonic receiver that can provide real-time image data of nerves, muscles, bones, and other tissues. Other examples include electrical sensors that detect signals from stimulated tissues or muscles. The Sensor/Actuator Control module 950 provides the ability to control both the actuation and pickup of such signals, all under control of the MCP 910.

Application Program Interfaces

The MCP 910 is also responsible for supervising the various Application Program Interfaces (APIs) that will be made available for 3rd party developers. There may exist more than one API 914 depending upon the specific developer audience to be enabled. For example many statistical focused apps will desire access to the Data Warehouse 926 and its cumulative store of data recorded from TNSS 934 and User 932 inputs. Another group of healthcare professionals may desire access to the Therapy Library 922 and Tissue Models 924 to construct better regimens for addressing specific diseases or disabilities. In each case a different specific API 914 may be appropriate.

The MCP 910 is responsible for many software functions of the TNSS system including system maintenance, debugging and troubleshooting functions, resource and device management, data preparation, analysis, and communications to external devices or programs that exist on the smart phone or in the cloud, and other functions. However, one of its primary functions is to serve as a global request handler taking inputs from devices handled by the Communications Controller 930, external requests from the Sensor Control Actuator Module (950), and 3rd party requests 936. Examples of High Level Master Control Program (MCP) functions are disclosed below.

Figure 25B:
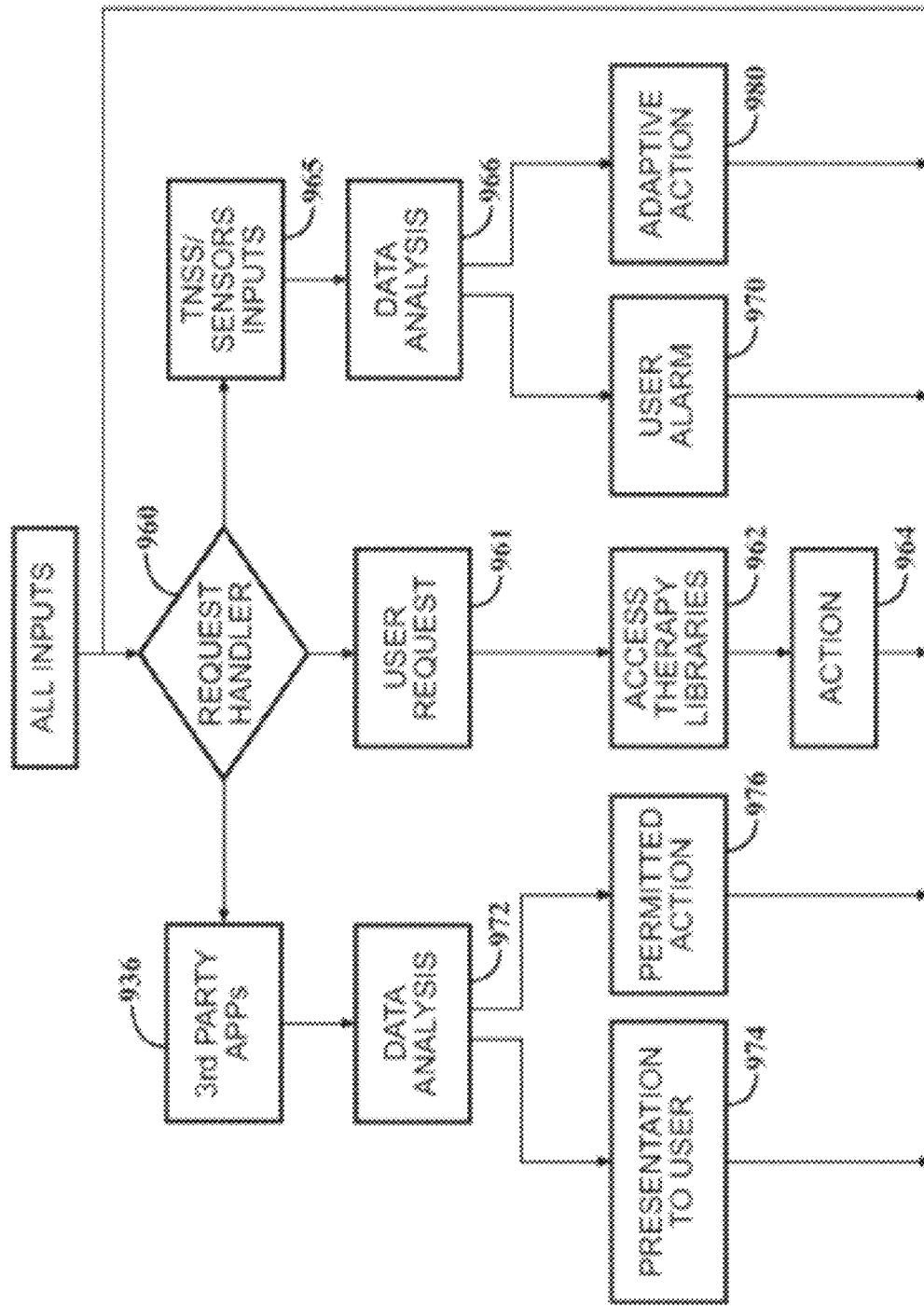
FIG. 25B is a flow chart showing an example of a function of a master control program in accordance with one example.

The manner in which the MCP handles these requests is shown in FIG. 25B. The Request Handler (RH) 960 accepts inputs from the User 932, TNSS devices 934, 3rd party apps 936, sensors 938 and other sources. It determines the type of request and dispatches the appropriate response as set forth in the following paragraphs.

User Request: The RH 960 will determine which of the plurality of User Requests 961 is present such as: activation; display status, deactivation, or data input, e.g. specific User condition. Shown in FIG. 25B is the RH's 960 response to an activation request. As shown in block 962, RH 960 will access the Therapy Library 922 and cause the appropriate regimen to be sent to the correct TNSS 934 for execution, as shown at block 964 labeled "Action."

TNSS/Sensor Inputs: The RH 960 will perform data analysis over TNSS 934 or Sensor inputs 965. As shown at block 966, it employs data analysis, which may include techniques ranging from DSP decision-making processes, image processing algorithms, statistical analysis and other algorithms to analyze the inputs. In FIG. 25B two such analysis results are shown; conditions which cause a User Alarm 970 to be generated and conditions which create an Adaptive Action 980 such as causing a control feedback loop for specific TNSS 934 functions, which can iteratively generate further TNSS 934 or Sensor inputs 965 in a closed feedback loop.

3rd Party Apps: Applications can communicate with the MCP 910, both sending and receiving communications. A typical communication would be to send informational data or commands to a TNSS 934. The RH 960 will analyze the incoming application data, as shown at block 972. FIG. 25B shows two such actions that result. One action, shown at block 974 would be the presentation of the application data, possibly reformatted, to the User 932 through the MCP User Interface 912. Another result would be to perform a User 932 permitted action, as shown at 976, such as requesting a regimen from the Therapy Library 922.

Figure 26:
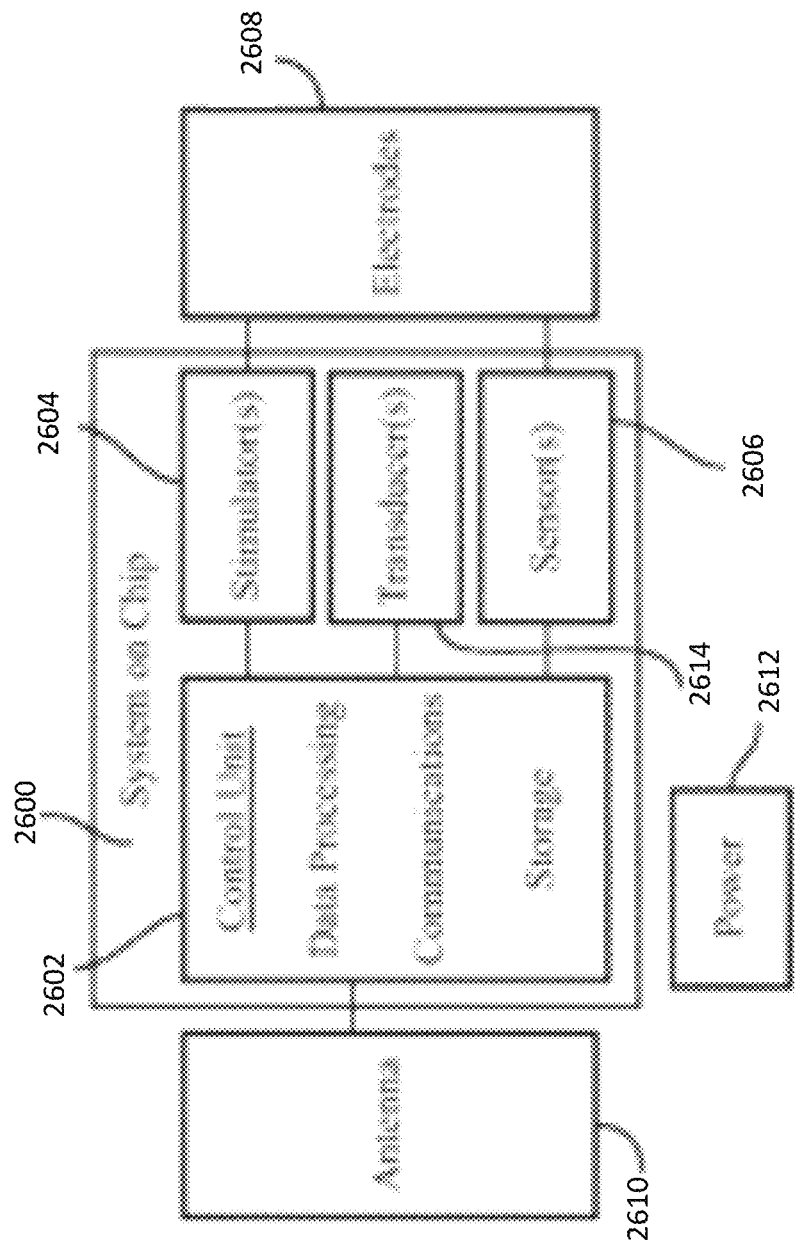
FIG. 26 is a block diagram of an example TNSS component configuration including a system on a chip (SOC) in accordance with one example.

Referring to FIG. 26, an example TNSS in accordance to one example is shown. The TNSS has one or more electronic circuits or chips 2600 that perform the functions of: communications with the controller, nerve stimulation via electrodes 2608 that produce a wide range of electric field(s) according to treatment regimen, one or more antennae 2610 that may also serve as electrodes and communication pathways, and a wide range of sensors 2606 such as, but not limited to, mechanical motion and pressure, temperature, humidity, chemical and positioning sensors. In another example, TNSS interfaces to transducers 2614 to transmit signals to the tissue or to receive signals from the tissue.

One arrangement is to integrate a wide variety of these functions into an SOC, system on chip 2600. Within this is shown a control unit 2602 for data processing, communications, transducer interface and storage and one or more stimulators 2604 and sensors 2606 that are connected to electrodes 2608. An antenna 2610 is incorporated for external communications by the control unit. Also present is an internal power supply 2612, which may be, for example, a battery. An external power supply is another variation of the chip configuration. It may be necessary to include more than one chip to accommodate a wide range of voltages for data processing and stimulation. Electronic circuits and chips will communicate with each other via conductive tracks within the device capable of transferring data and/or power.

The TNSS interprets a data stream from the control device, such as that shown in FIG. 25A, to separate out message headers and delimiters from control instructions. In one example, control instructions contain information such as voltage level and pulse pattern. The TNSS activates the stimulator 2604 to generate a stimulation signal to the electrodes 2608 placed on the tissue according to the control instructions. In another example the TNSS activates a transducer 2614 to send a signal to the tissue. In another example, control instructions cause information such as voltage level and pulse pattern to be retrieved from a library stored in the TNSS.

The TNSS receives sensory signals from the tissue and translates them to a data stream that is recognized by the control device, such as the example in FIG. 25A. Sensory signals include electrical, mechanical, acoustic, optical and chemical signals among others. Sensory signals come to the TNSS through the electrodes 2608 or from other inputs originating from mechanical, acoustic, optical, or chemical transducers. For example, an electrical signal from the tissue is introduced to the TNSS through the electrodes 2608, is converted from an analog signal to a digital signal and then inserted into a data stream that is sent through the antenna 2610 to the control device. In another example an acoustic signal is received by a transducer 2614 in the TNSS, converted from an analog signal to a digital signal and then inserted into a data stream that is sent through the antenna 2610 to the control device. In certain examples sensory signals from the tissue are directly interfaced to the control device for processing.

An open loop protocol to control current to electrodes in known neural stimulation devices does not have feedback controls. It commands a voltage to be set, but does not check the actual Voltage. Voltage control is a safety feature. A stimulation pulse is sent based on preset parameters and cannot be modified based on feedback from the patient's anatomy. When the device is removed and repositioned, the electrode placement varies. Also the humidity and temperature of the anatomy changes throughout the day. All these factors affect the actual charge delivery if the voltage is preset.

In contrast, examples of the TNSS stimulation device have features that address these shortcomings using the Nordic Semiconductor nRF52832 microcontroller to regulate charge in a TNSS. The High Voltage Supply is implemented using a LED driver chip combined with a Computer controlled Digital Potentiometer to produce a variable voltage. A 3-1 step up Transformer then provides the desired High Voltage, "VBOOST", which is sampled to assure that no failure causes an incorrect Voltage level as follows. The nRF52832 Microcontroller samples the voltage of the stimulation waveform providing feedback and impedance calculations for an adaptive protocol to modify the waveform in real time. The Current delivered to the anatomy by the stimulation waveform is integrated using a differential integrator and sampled and then summed to determine actual charge delivered to the user for a Treatment. After every pulse in a Stimulation event, this measurement is analyzed and used to modify, in real time, subsequent pulses.

This hardware adaptation allows a firmware protocol to implement the adaptive protocol. This protocol regulates the charge applied to the body by changing VBOOST. A treatment is performed by a sequence of periodic pulses, which insert charge into the body through the electrodes. Some of the parameters of the treatment are fixed and some are user adjustable. The strength, duration and frequency may be user adjustable. The user may adjust these parameters as necessary for comfort and efficacy. The strength may be lowered if there is discomfort and raised if nothing is felt. The duration will be increased if the maximum acceptable strength results in an ineffective treatment.

Figure 27:
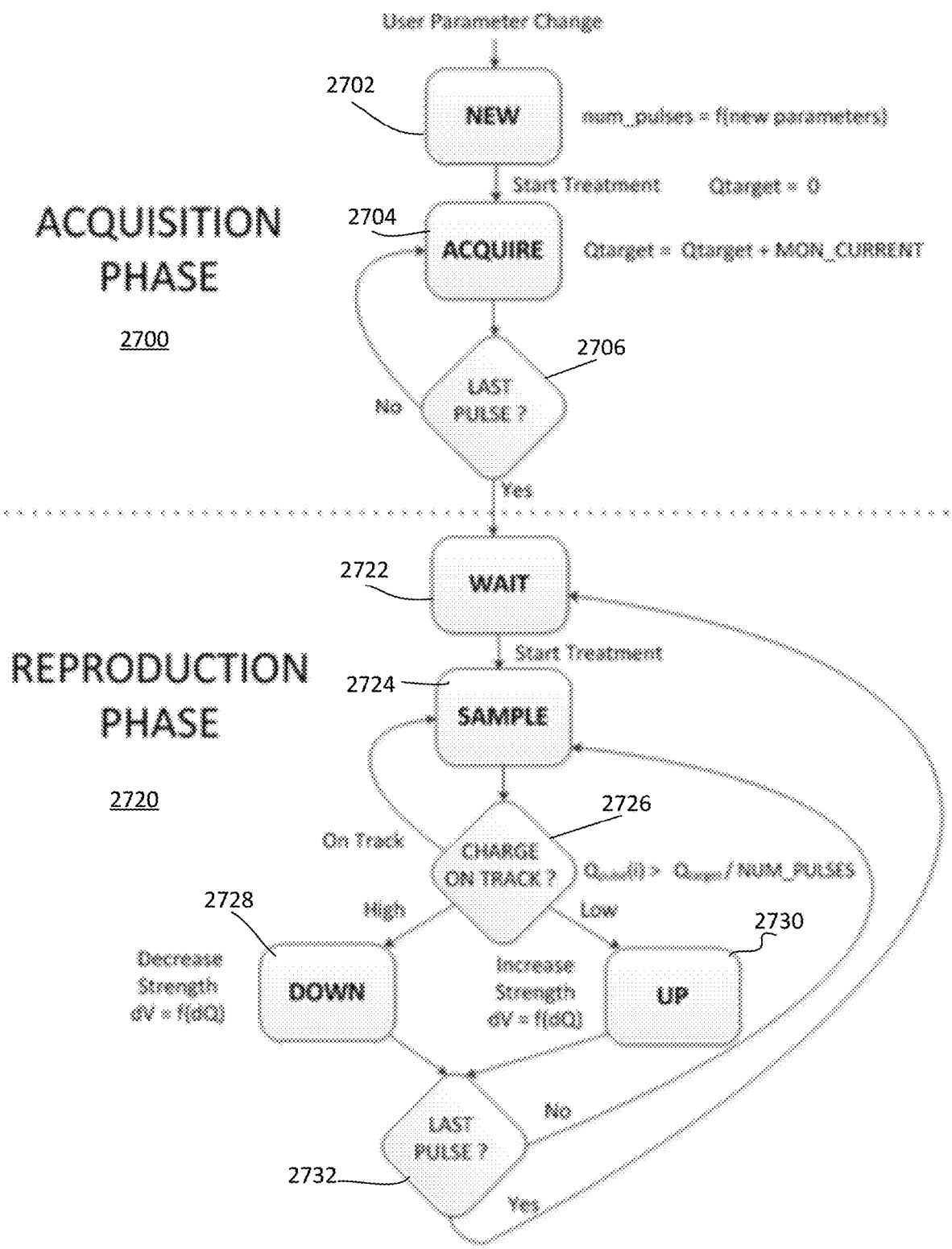
FIG. 27 is a flow diagram of the protocol for adaptive current control in accordance with one example.

A flow diagram in accordance with one example of the Adaptive Protocol disclosed above is shown in FIG. 27. The Adaptive Protocol strives to repeatedly and reliably deliver a target charge ("$Q_{target}$") during a treatment and to account for any environmental changes. Therefore, the functionality of FIG. 27 is to adjust the charge level applied to a user based on feedback, rather than use a constant level.

The mathematical expression of this protocol is as follows: $Q_{target} = Q_{target}(A*dS + B*dT)$, where A is the Strength Coefficient—determined empirically, dS is the user change in Strength, B is the Duration Coefficient—determined empirically, and dT is the user change in Duration.

Figure 28:
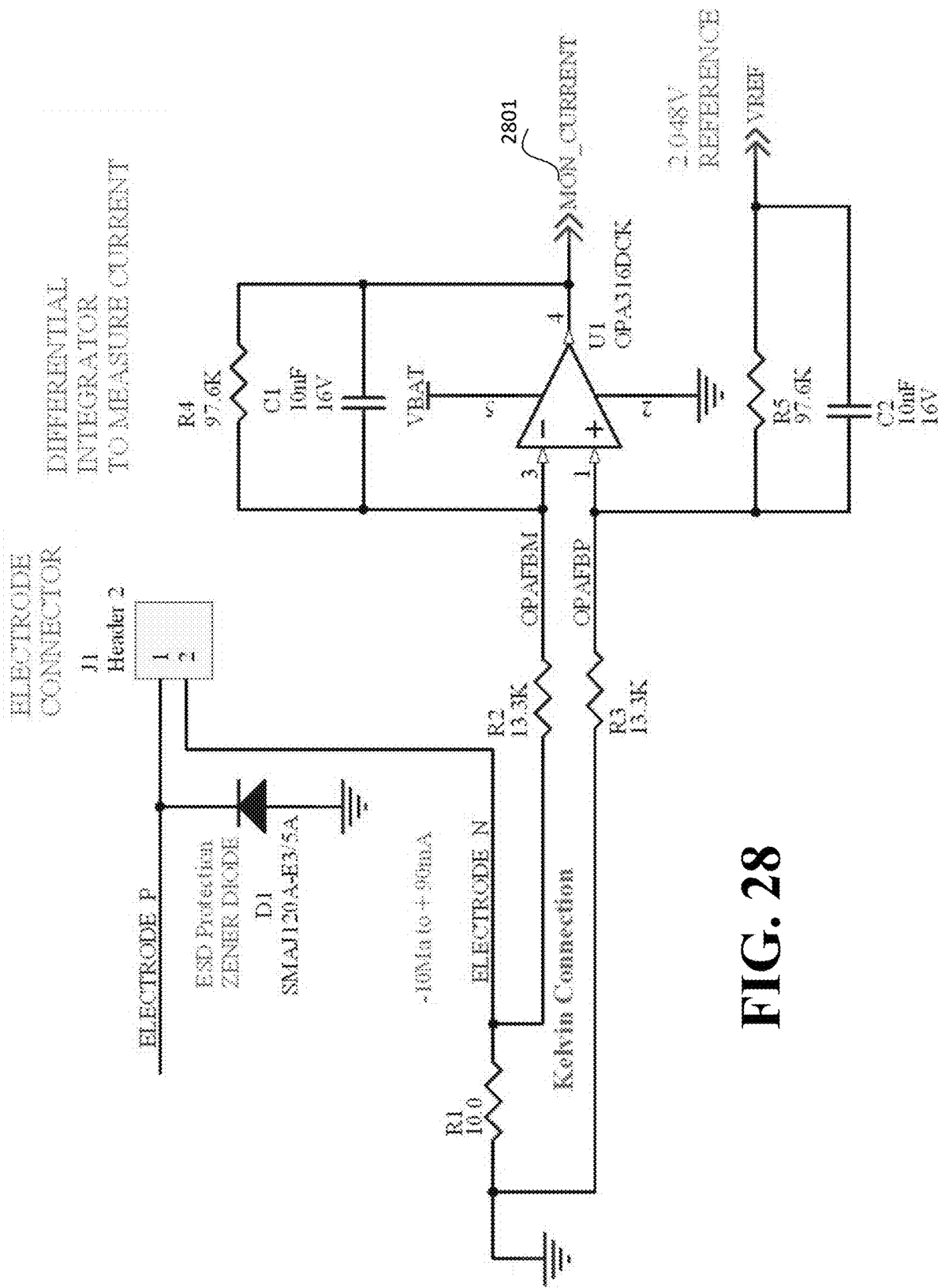
FIG. 28 is a Differential Integrator Circuit used in the Adaptive Current Protocol in accordance with one example.

The Adaptive Protocol includes two phases in one example: Acquisition 2700 and Reproduction 2720. Any change in user parameters places the Adaptive Protocol in the Acquisition phase. When the first treatment is started, a new baseline charge is computed based on the new parameters. At a new acquisition phase at 2702, all data from the previous charge application is discarded. In one example, 2702 indicates the first time for the current usage where the user places the TNSS device on a portion of the body and manually adjusts the charge level, which is a series of charge pulses, until it feels suitable, or any time the charge level is changed, either manually or automatically. The treatment then starts. The mathematical expression of this function of the application of a charge is as follows:

$$\text{The charge delivered in a treatment is } Q_{target} = \sum_{i=1}^{T*f} Q_{pulse}(i)$$

Where T is the duration; f is the frequency of "Rep Rate"; $Q_{pulse}$ (i) is the measured charge delivered by Pulse (i) in the treatment pulse train provided as a voltage MON_CURRENT that is the result of a Differential Integrator circuit shown in FIG. 28 (i.e., the average amount of charge per pulse). The Nordic microcontroller of FIG. 28 is an example of an Analog to Digital Conversion feature used to quantify voltage into a number representing the delivered charge and therefore determine the charge output. The number of pulses in the treatment is T*f.

At 2704 and 2706, every pulse is sampled. In one example, the functionality of 2704 and 2706 lasts for 10 seconds with a pulse rate of 20 Hz, which can be considered a full treatment cycle. The result of phase 2700 is the target pulse charge of $Q_{target}$.

Figure 29:
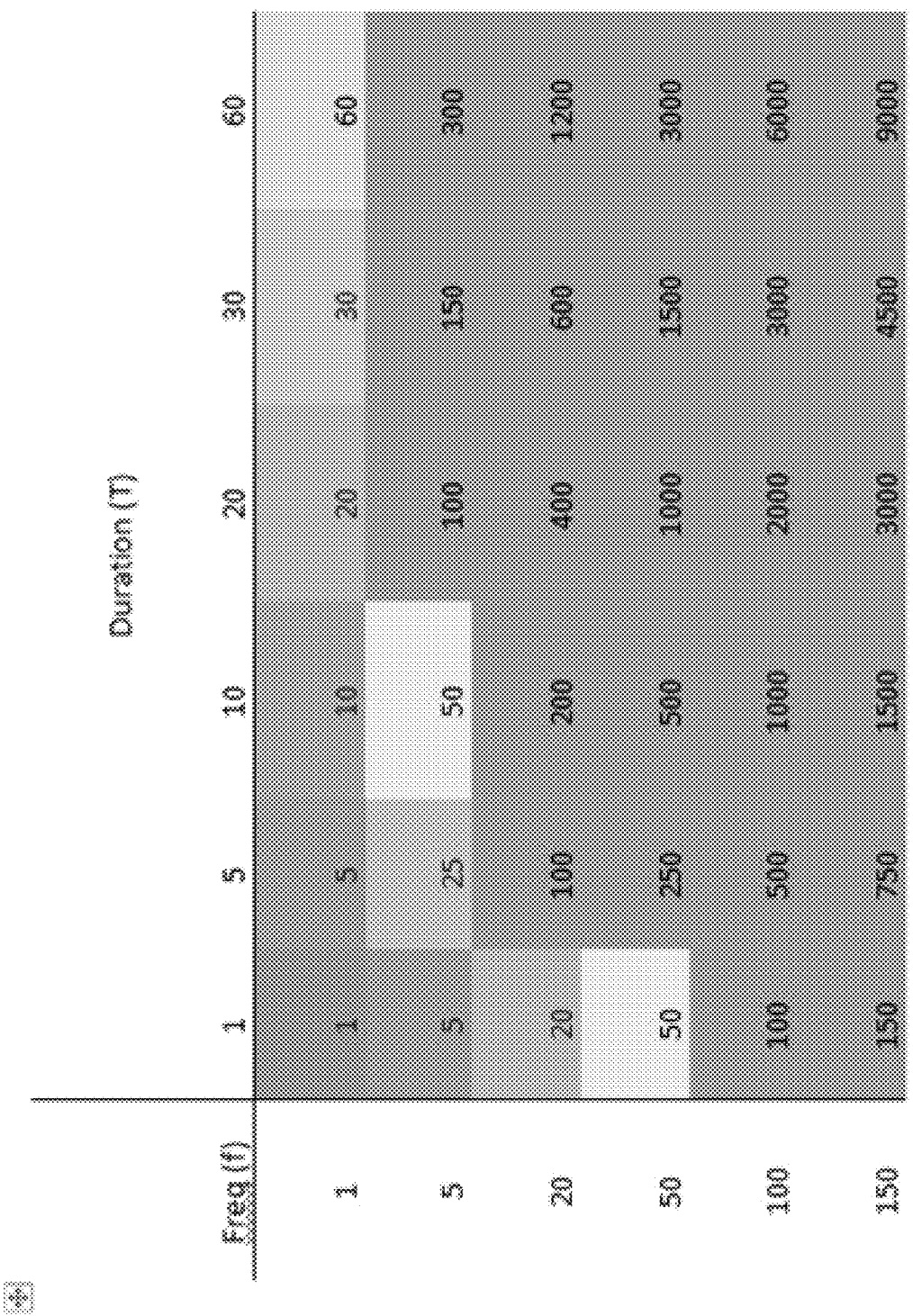
FIG. 29 is a table relating charge duration vs. frequency to provide feedback to the Adaptive Current Protocol in accordance with one example.

FIG. 29 is a table in accordance with one example showing the number of pulses per treatment measured against two parameters, frequency and duration. Frequency is shown on the Y-axis and duration on the X-axis. The Adaptive Current protocol in general performs better when using more pulses. One example uses a minimum of 100 pulses to provide for solid convergence of charge data feedback. Referring to the FIG. 29, a frequency setting of 20 Hz and duration of 10 seconds produces 200 pulses, which is desirable to allow the Adaptive Current Protocol to reproduce a previous charge.

The reproduction phase 2720 begins in one example when the user initiates another subsequent treatment after acquisition phase 2700 and the resulting acquisition of the baseline charge, $Q_{target}$. For example, a full treatment cycle, as discussed above, may take 10 seconds. After, for example, a two-hour pause as shown at wait period 2722, the user may then initiate another treatment. During this phase, the Adaptive Current Protocol attempts to deliver $Q_{target}$ for each subsequent treatment. The functionality of phase 2720 is needed because, during the wait period 2722, conditions such as the impedance of the user's body due to sweat or air humidity may have changed. The differential integrator is sampled at the end of each Pulse in the Treatment. At that point, the next treatment is started and the differential integrator is sampled for each pulse at 2724 for purposes of comparison to the acquisition phase $Q_{target}$. Sampling the pulse includes measuring the output of the pulse in coulombs. The output of the integrator of FIG. 28 in voltage, referred to as Mon_Current 2801, is a direct linear relationship to the delivered charge in micro-coulombs and provides a reading of how much charge is leaving the device and entering the user. At 2726, each single pulse is compared to the charge value determined in phase 2700 (i.e., the target charge) and the next pulse will be adjusted in the direction of the difference.

NUM_PULSES=(T*f)

After each pulse, the observed charge, $Q_{pulse}(i)$, is compared to the expected charge per pulse.

$Q_{pulse}(i) > Q_{target}$/NUM_PULSES?

The output charge or "VBOOST" is then modified at either 2728 (decreasing) or 2730 (increasing) for the subsequent pulse by:

$dV(i)=G[Q_{target}/\text{NUM\_PULSES}-Q_{pulse}(i)]$ where G is the Voltage adjustment Coefficient—determined empirically. The process continues until the last pulse at 2732.

A safety feature assures that the VBOOST will never be adjusted higher by more than 10%. If more charge is necessary, then the repetition rate or duration can be increased.

In one example, in general, the current is sampled for every pulse during acquisition phase 2700 to establish target charge for reproduction. The voltage is then adjusted via a digital potentiometer, herein referred to as "Pot", during reproduction phase 2720 to achieve the established target_charge.

The digital Pot is calibrated with the actual voltage at startup. A table is generated with sampled voltage for each wiper value. Tables are also precomputed storing the Pot wiper increment needed for 1v and 5v output delta at each pot level. This enables quick reference for voltage adjustments during the reproduction phase. The tables may need periodic recalibration due to battery level.

In one example, during acquisition phase 2700, the minimum data set=100 pulses and every pulse is sampled and the average is used as the target_charge for reproduction phase 2720. In general, less than 100 pulses may provide an insufficient data sample to use as a basis for reproduction phase 2720. In one example, the default treatment is 200 pulses (i.e., 20 Hz for 10 seconds). In one example, a user can adjust both duration and frequency manually.

In one example, during acquisition phase 2700, the maximum data set=1000 pulses. The maximum is used to avoid overflow of 32 bit integers in accumulating the sum of samples. Further, 1000 pulses in one example is a sufficiently large data set and collecting more is likely unnecessary.

After 1000 pulses for the above example, the target_charge is computed. Additional pulses beyond 1000 in the acquisition phase do not contribute to the computation of the target charge.

In one example, the first 3-4 pulses are generally higher than the rest so these are not used in acquisition phase 2700. This is also accounted for in reproduction phase 2720. Using these too high values can result in target charge being set too high and over stimulating on the subsequent treatments in reproduction phase 2720. In other examples, more advanced averaging algorithms could be applied to eliminating high and low values.

In an example, there may be a safety concern about automatically increasing the voltage. For example, if there is poor connection between the device and the user's skin, the voltage may auto-adjust at 2730 up to the max. The impedance may then be reduced, for example by the user pressing the device firmly, which may result in a sudden high current. Therefore, in one example, if the sample is 500 mv or more higher than the target, it immediately adjusts to the minimum voltage. This example then remains in reproduction phase 2720 and should adjust back to the target current/charge level. In another example, the maximum voltage increase is set for a single treatment (e.g., 10V). More than that should not be needed in normal situations to achieve the established target_charge. In another example, a max is set for VBOOST (e.g., 80V).

In various examples, it is desired to have stability during reproduction phase 2720. In one example, this is accomplished by adjusting the voltage by steps. However, a relatively large step adjustment can result in oscillation or over stimulation. Therefore, voltage adjustments may be made in smaller steps. The step size may be based on both the delta between the target and sample current as well as on the actual VBOOST voltage level. This facilitates a quick and stable/smooth convergence to the target charge and uses a more gradual adjustments at lower voltages for more sensitive users.

The following are the conditions that may be evaluated to determine the adjustment step.

delta-mon_current=abs(sample_mon_current−target_charge)

If delta_mon_current>500 mv and VBOOST>20V then step=5V for increase adjustments (For decrease adjustments a 500 mv delta triggers emergency decrease to minimum Voltage)

If delta_mon_current>200 mv then step=1V

If delta_mon_current>100 mv and delta_mon_current>5%*sample_mon_current then step=1V In other examples, new treatments are started with voltage lower than target voltage with a voltage buffer of approximately 10%. The impedance is unknown at the treatment start. These examples save the target_voltage in use at the end of a treatment. If the user has not adjusted the strength parameter manually, it starts a new treatment with saved target_voltage with the 10% buffer. This achieves target current quickly with the 10% buffer to avoid possible over stimulation in case impedance has been reduced. This also compensates for the first 3-4 pulses that are generally higher.

As disclosed, examples apply an initial charge level, and then automatically adjust based on feedback of the amount of current being applied. The charge amount can be varied up or down while being applied. Therefore, rather than setting and then applying a fixed voltage level throughout a treatment cycle, implementations of the invention measure the amount of charge that is being input to the user, and adjust accordingly throughout the treatment to maintain a target charge level that is suitable for the current environment.

Obstructive Sleep Apnea

In addition to the applications of the patch in accordance to example inventions disclosed above, in other example inventions, the patch is used to detect and then reduce/treat the number of apnea or hypopnea episodes during sleep, thereby improving the sleep architecture of individuals with obstructive sleep apnea (OSA) or obstructive sleep hypopnea. The behavior of these individuals is changed to provide better quality sleep, which in turn affects their behavior during daytime activities. In other example inventions, the patch is used for a diagnostic method and system to allow an individual to determine whether they exhibit symptoms of OSA, without having to consult a physician. Similarly, example inventions provide a method and system that physicians may offer to their patients to diagnose OSA without the complex and intrusive system of a conventional sleep study in a clinic In general, example inventions provide an integrated system in the form of the patch which may be placed on the skin of the user and be automatically activated and used with or without the help of a medical professional. The integrated system includes hardware and software to selectively stimulate nerves in the neck or lower jaw related to OSA, while also monitoring biometrics related to breathing, and also optionally measuring respiration or acoustic measurements using oximetry in some examples, and stimulating the hypoglossal nerve to relieve apnea to provide a closed-loop system.

The hypoglossal nerve (HN) is the $12^{th}$ cranial nerve (CXII) that controls the muscles of the tongue, excepting the palatoglossus muscle. Two hypoglossal nerves descend from the brain through the hypoglossal canals, with one hypoglossal nerve lying along the underside of the tongue on each of the left and right sides of the tongue.

The genioglossus is the muscle that controls the protrusion of the tongue and is innervated by the HN. It has a left and a right component. When components are stimulated, the center of the back of the tongue is depressed and the tongue protrudes forward. This opens the airway. When the muscle is relaxed, the airway may be obstructed. The two medial branches of the hypoglossal nerve innervate the two sides of the genioglossus muscle.

Insufficient activation of the upper airway muscles leads to upper airway obstruction in individuals with obstructive sleep apnea. Increasing the activity in these muscles can reduce the obstructive air pressure, relieving restrictions on breathing, and improving sleep, while also reducing the severity of oxyhemoglobin desaturations.

Known solutions to OSA include using implanted nerve stimulation to increases muscle activity related to OSA. This stimulation is applied to one or both of the hypoglossal nerves. In contrast, example inventions avoid implanted stimulation and implanted breathing monitoring in favor of transcutaneous monitoring of breathing and stimulation of the hypoglossal nerve, therefore avoiding any surgical procedures.

Figure 30:
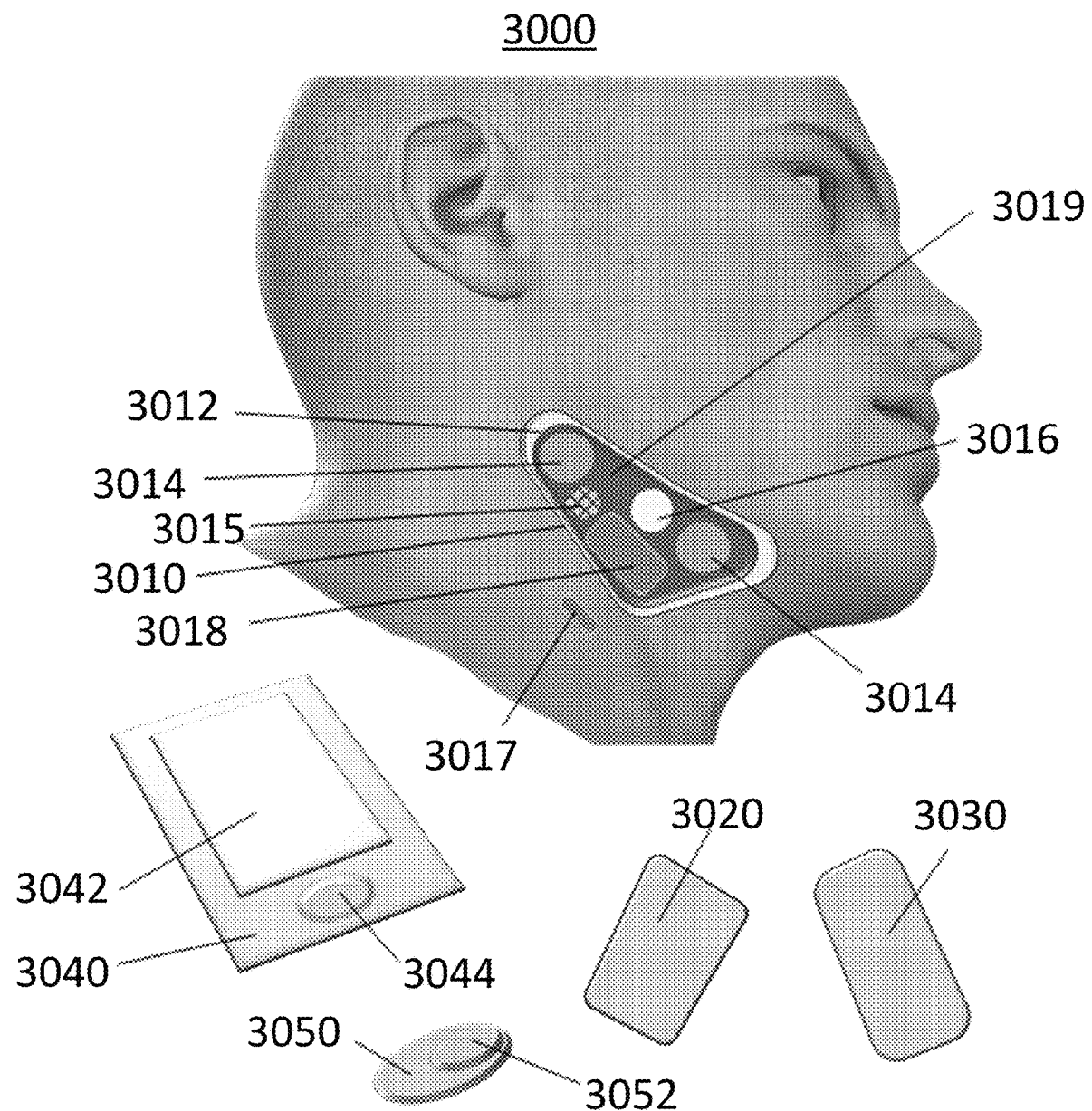
FIG. 30 is an obstructive sleep apnea suppression and detection system in accordance with one example.

FIG. 30 is an obstructive sleep apnea suppression and detection system 3000 in accordance with one example. System 3000 includes a Neck Topical Nerve Activator (TNA) device 3010 (or "patch" 3010) that includes a securing mechanism 3012 (e.g., adhesive layer), and one or more electrode pairs 3014 with each pair having a positive electrode and a negative electrode, a sensor 3015, a tag 3017, a power source 3016 and a processor/controller 3018. System 3000 further includes a respiration monitoring device 3020, a posture indication device 3030, a smart controller 3040 with a display 3042, and an acknowledgment button 3044 and a fob 3050 with one or more buttons 3052.

Figure 31A:
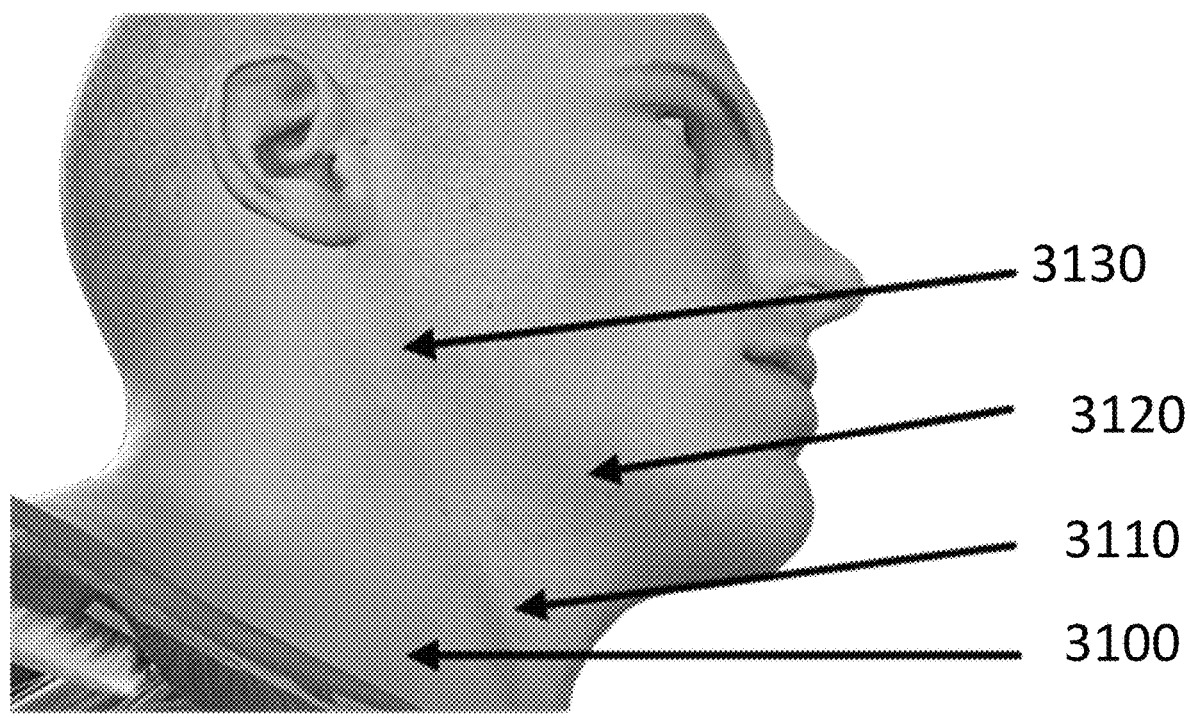
FIG. 31A illustrates a user with a neck, a jaw line, and an area behind the mandible.

FIG. 31A illustrates a user 3100 with a neck 3110, a jaw line 3120, and an area 3130 behind the mandible.

Figure 31B:
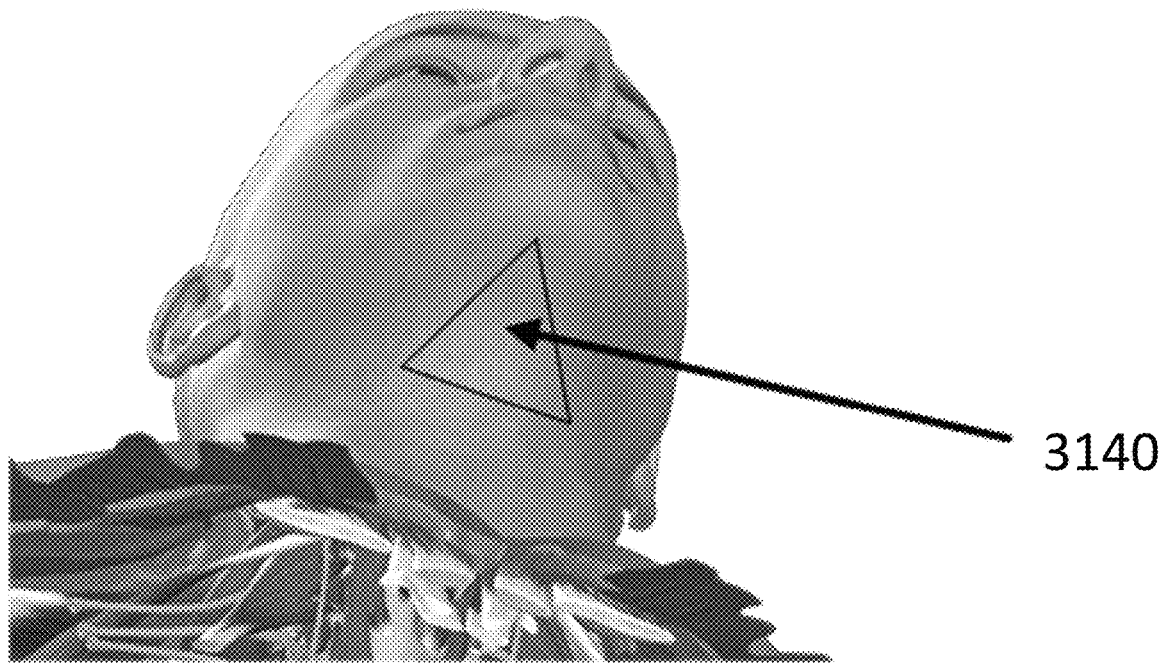
FIG. 31B illustrates the user and a submental triangle below the chin.

FIG. 31B illustrates the user 3100 and a submental triangle 3140 below the chin.

Figure 31C:
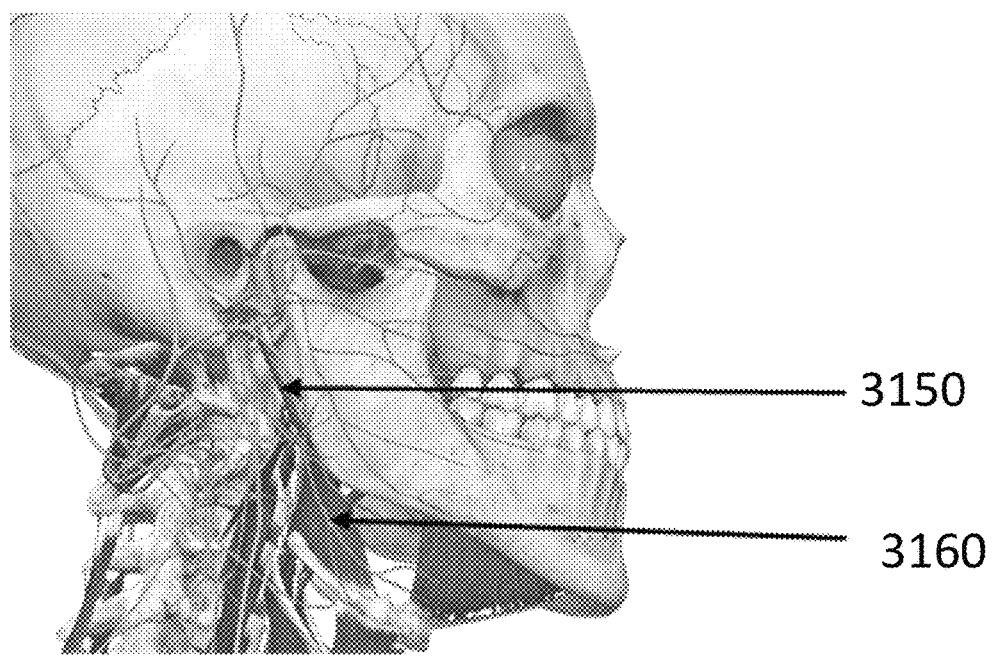
FIG. 31C illustrates the user and an internal view of the hypoglossal nerve and the sublingual nerve.

FIG. 31C illustrates the user 3100 and an internal view of the hypoglossal nerve 3150 and the sublingual nerve 3160.

Figure 31D:
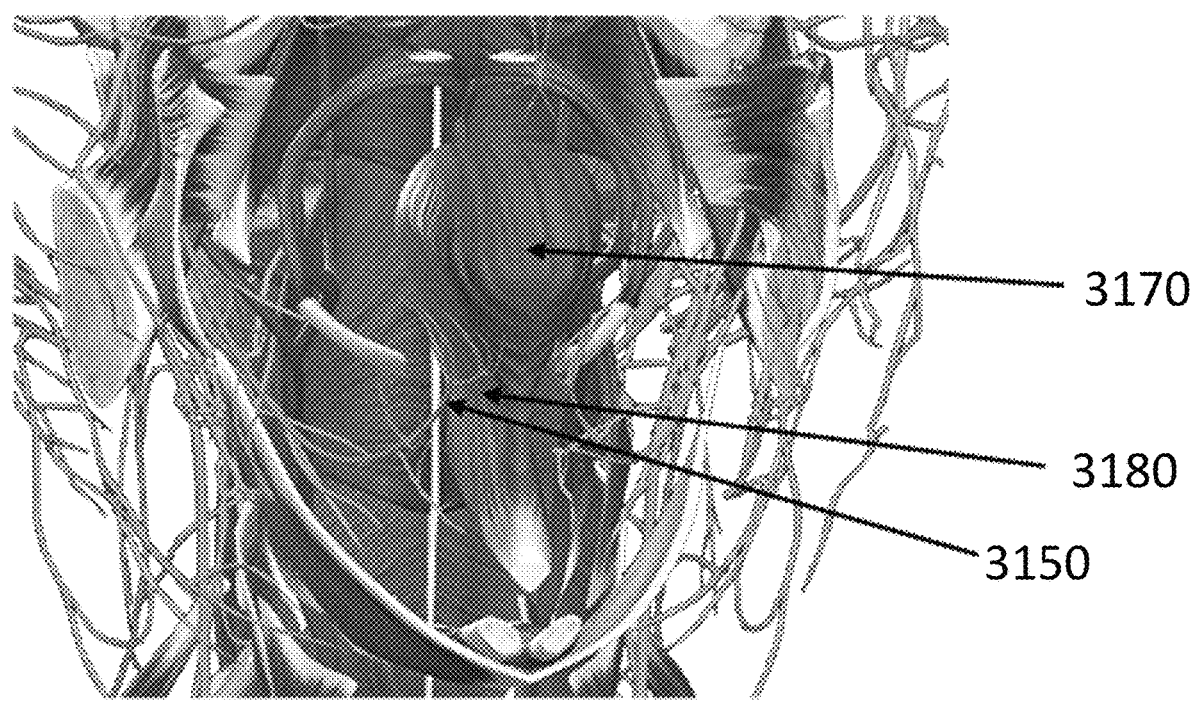
FIG. 31D illustrates the user and an internal view of the hypoglossal nerve, and the genioglossus muscle under the tongue.

FIG. 31D illustrates the user 3100 and an internal view of the hypoglossal nerve 3150, and the genioglossus muscle 3180 under the tongue 3170.

Figure 32:
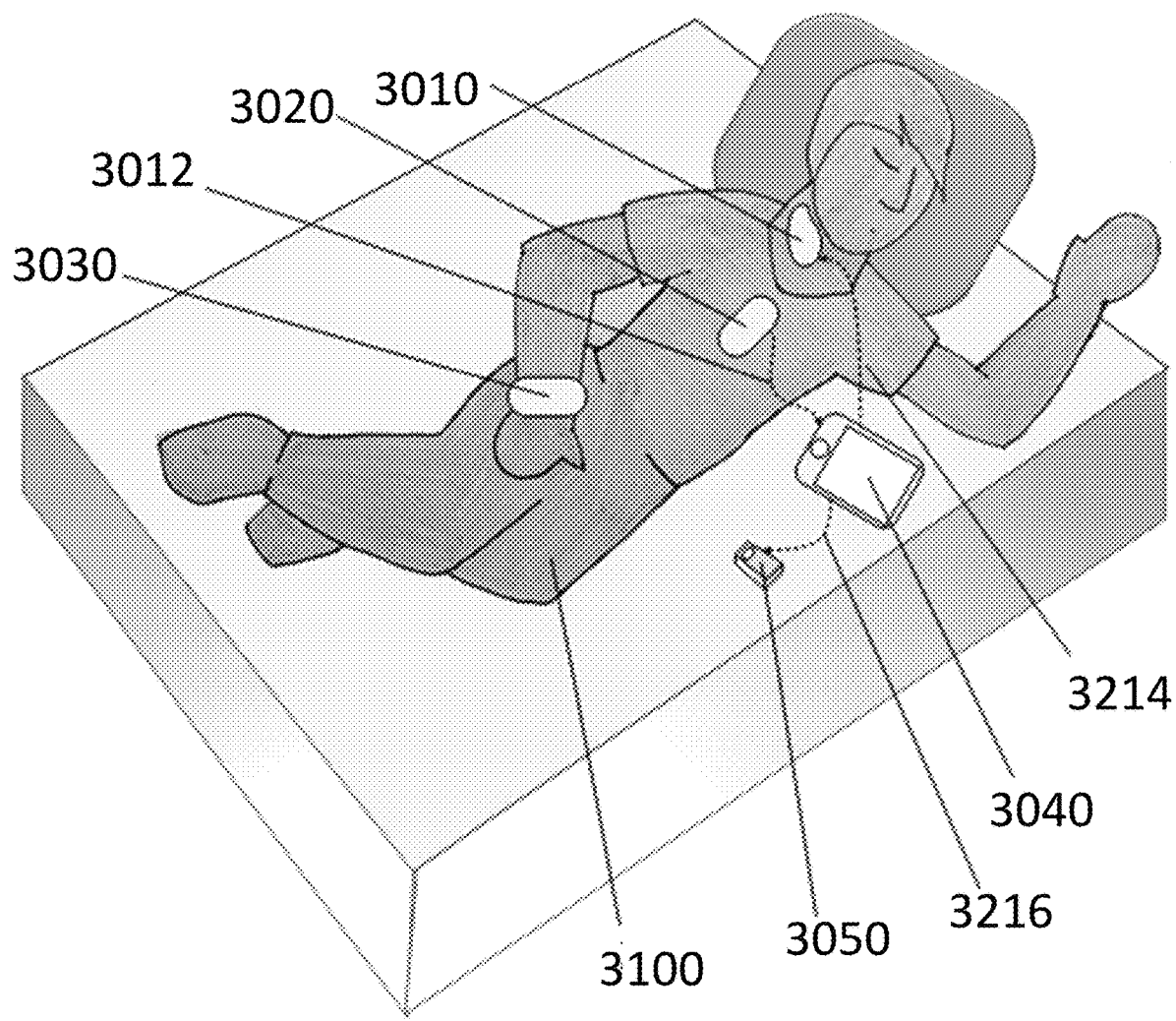
FIG. 32 illustrates an example placement of a patch and other elements of the system in accordance with one example.

FIG. 32 illustrates an example placement of patch 3010 and other elements of system 3000 in accordance with one example. As shown in FIG. 32, patch 3010 is configured to be placed on either side of the neck, or on the jaw in one of several locations, such as the submental triangle 3140, below the jawline 3120, or behind the mandible 3130 and is situated to be able to accurately monitor biometrics related to breathing. Patch 3010 is situated such that electrical stimulation may activate one or more branches of the hypoglossal nerve 3140 on one or both sides of the neck 3110 using electrical fields. Sensors may assist in placement, which can be the same sensors for detection/measurement of biometrics (e.g., ultrasound). Electrodes may be used to assist in placement. In embodiments, patch 3010 is implemented using elements shown in the patch of FIGS. 4-9 above.

Referring again to FIG. 30, patch 3010 is designed and configured in a shape to conform to the skin when affixed to the skin to be electronically effective at stimulating the hypoglossal nerve 3140 and monitoring breathing. Patch 3010 can be used for apnea detection as well as for delivering electrical stimulation. Patch 3010 is electronically most effective for stimulation when the positive and negative electrodes are placed axially along the path of the nerve in contrast to transversely across the path of the nerve, which is not as electronically effective. The shape of patch 3010 is designed to minimize discomfort for the user 3100 when affixed in the target location.

In some examples, patch 3010 uses one electrode pair 3014 to activate the hypoglossal nerve 3140 on one of the distal or lateral sides of the neck 3110. In some examples, patch 3010 uses two electrode pairs 3014 to activate both the distal and lateral branches of the hypoglossal nerve 3140 on the neck 3110.

In some examples, patch 3010 uses multiple positive electrodes and one or more negative electrodes to activate one or both of the distal and lateral branches of the hypoglossal nerve 3140, modifying the waveshapes or timings or both of the activation pulses from the multiple electrodes to direct the waveform energy at one or more specific points on the hypoglossal nerves. Various arrays of electrodes as disclosed above can be controlled to generate optimized stimulation. The stimulation can be adaptive based on feedback from sensors as disclosed above. The stimulation, in the form of electrical stimuli generated by the electrodes when patch 3010 is activated, in examples include square waves having an amplitude between 10 and 100 volts, pulse widths between 100 and 500 microseconds, and a pulse repetition rate of between 2 and 60 pulses per second.

In some examples, patch 3010 uses adhesive surfaces to attach to the skin. In some examples, the patch 3010 is affixed to the underside of the jaw line 3120 on one or both sides of the jaw, using its electrodes to activate the hypoglossal nerve 3150 on one or both sides as the nerve enters the underside of the tongue 3170 into the genioglossus muscle 3180.

In some examples, patch 3010 is affixed on the throat, in the submental triangle 3140 which overlies the submental muscle, which lies below the mylohyoid, geniohyoid, and genioglossus muscles, using its electrodes to activate the innervation of the genioglossus muscle 3180, to cause the tongue 3170 to push forward, opening the upper air way. Multiple negative and positive electrodes can be used, and beam steering, beam selection, and interferential stimulation can be used to select the targeted nerve deep inside the tissue.

In some examples, patch 3010 is affixed on the back of the jaw, behind the mandible 3130, using its electrodes to activate the hypoglossal nerve 3150 before it is occluded by the muscles of the neck, the activations proceeding down the nerve into the genioglossus muscle 3180.

In some examples, patch 3010 is affixed to one of the left and right sides of the jaw line or back of the jaw, alternating to the opposite side of the jaw line or jaw on succeeding nights, or to a similar schedule, in order to activate the genioglossus muscle on both sides of the tongue to an equal degree when averaged across a series of days, while using a patch 3010 that is small enough in dimensions to fit on one side of the body.

The individual components of the system 3000 may be connected as peer devices in a Body Area Network, passing each other signals and sharing the tasks of data recording, real-time analysis, and closed-loop monitoring of the user.

In examples, activating patch 3010 generates electrical charges on the electrodes to stimulate the genioglossus muscle, with the hypoglossal nerve, with the result being causing unconscious movement of the user's tongue, and "treating" the sleep apnea condition. In other examples, other nerves can be stimulated that cause movement of the tongue through a reflex (i.e., a rapid, involuntary response to a stimulus) and/or a reflex arc (i.e., the pathway traveled by the nerve impulses during a reflex). For example, the following reflexes cause the tongue to move in response to electrical stimulation:

Glossopharyngeal/Hypoglossal reflex: Stimulation of the glossopharyngeal and superior laryngeal nerves results in the excitation of the genioglossus muscles. This reflex results in a protrusion of the tongue.

Jaw/tongue reflexes: Opening of the jaw results in reflexive activity of the genioglossus muscle.

Masseter Reflex: Stimulation of masseter afferents excites muscles which protrude the tongue, (primarily the genioglossus) and inhibits opposing muscles.

Temporalis Reflex: Light pressure on temporalis muscle activates hypoglossal motoneurons that innervate the tongue muscles.

Pharyngeal Reflex: Sensory mechanoreceptors located within the pharyngeal mucosa play an important role in the reflex which maintains upper airway patency. For example, pharyngeal negative pressure sensors activate dilatory muscles of the upper airway and help stabilize the airway.

In some examples, patch 3010 includes one or more sensors which measure internal features or biometrics of the user in the neck area, these measurements used to help the user to orient and place patch 3010 most accurately in the target location. The sensor data is communicated to one or more of smart controller 3040, fob 3050 and patch 3010, and an indication such as an LED or vibration is sent to the user to assist them in placing the device.

For example, the orientation vertically or horizontally of the patch 3010 itself can be determined by a 9-axis accelerometer on the patch. The smart phone app can tell the user in real-time to rotate the patch to the proper orientation before sticking it to the skin. The shape of patch 3010 can be designed in a shape to assist the user in orienting it properly. Further, a marking (e.g., an arrow meant to be vertical) could be printed on the patch or on a removable paper liner (so that the arrow is removed when the patch is actually applied).

Further, patch 3010 can be designed to accommodate multiple orientations. For example, the electrodes could be an array or series or matrix of sub-electrodes, and the patch could select which to use for effective stimulation based on the position and orientation of the patch. Similarly, patch 3010 can include two microphones which could have their roles reversed if the patch were placed "upside down" on the skin.

Further, the position of patch 3010 on the neck/throat/submental region could be deduced after the patch is affixed to the skin by sensing through the skin with the on-board sensors, then notifying the user through the app that the patch is good or that it needs to be re-positioned. For example, the sound of the jugular vein could be detected; or the sound of air in the pharynx positioned between the 2 microphones.

Further, patch 3010 includes electronic sensor 3015, in a fixed placement on patch 3010 relative to electrodes 3014. Sensors 3015 are used to detect the strength of the activation pulse at the target nerve through the use of tag 3017 previously placed on or near the target nerve. Tag 3017 responds to the activation signal from electrodes 3014 to a degree proportional to the strength of the activation signal coupled into the target nerve, and sends this response to patch 3010. The strength of this response is then used by the user to re-orient or move patch 3010 on the neck for optimum performance of the activation on the target nerve.

Respiration monitoring device 3020 detects occurrences of interrupted breathing due to an apnea episode or hypopnea episode, and notifies one or more of patch 3010, or smart controller 3040, or fob 3050 of such an episode. In some examples, respiration monitoring device 3020 measures the airflow during inspiration or expiration or both. In some examples, respiration monitoring device 3020 measures other biometric attributes of the user 3100 to determine the beginning of an apnea episode. Examples of these measurements may be blood oxygenation level, oximetry; or cessation of motion in the airway or lungs; or change in the audio signal from movement of air into and out of the lungs.

OSA has traditionally been diagnosed through a sleep study, or polysomnography, usually performed in a clinic setting with multiple electrodes monitoring multiple body parameters, including attaching multiple wired sensors and equipment such as thoracic belts, nasal flow meters to the body which interfere with natural sleep and thus the accuracy of true sleep measurements. However, requests for home screening tests are rising because of comfort and cost issues. The "STOPBANG" scale has been used to provide guidance to those individuals assumed to be at high risk for moderate to severe OSA, with the acronym defined as Snoring; Tiredness in daytime; Observation by third party of stopped breathing; high blood Pressure; Body Mass Index (BMI) greater than 35; Age over 50; Neck circumference greater than 16 inches; and male Gender. A STOPBANG score of 3 or more indicates a home test or sleep study should be performed, especially since up to 80% of people with OSA do not know they have apnea.

In some examples, OSA suppression and detection System 3000 includes patch 3010 and respiration monitoring device (RMD) 3020. RMD 3020 includes one or more accelerometers, a CO2 sensor, an oximeter, and an audio sensing device. The accelerometer detects rhythmic movements of respiration, or the lack of such movement. The CO2 sensor detects the carbon dioxide content airflow due to inspiration or exhalation. The oximeter monitors the saturation of peripheral oxygen (SpO2). The audio sensing device detects the sounds of snoring, body motion in bed, and background noise. Measuring airflow may include use of Doppler by laser, or ultrasonically, which could measure through the trachea rather than nasally.

RMD 3020 can be positioned at various locations on the body, depending upon which sensor and which body parameters are measured. For example, an RMD 3020 that includes an accelerometer can be positioned on the chest to detect rhythmic breathing patterns, or on the neck in the submental region, or on the lower neck at the suprasternal notch; whereas an RMD 3020 including a $CO_2$ sensor or an audio sensor can be positioned near the outside of the nasal passageway.

In some examples, RMD 3020 is a separate unit from patch 3010, which can be positioned at various anatomical locations around the body away from patch 3010. In some examples, RMD 3020 is integrated within patch 3010, with all elements coupled to a common substrate, and can monitor specific body signals at the same location as patch 3010. In some examples, RMD 3020 is a separate patch-like device with all elements coupled to a common substrate that is a different substrate than with patch 3010.

In some examples, RMD 3020 may send data related to respiration to smart controller 3040 during the user's sleep period while the stimulation function of patch 3010 is not activated, this data being collected to determine if the user exhibits signs of obstructive sleep apnea. In some examples RMD 3020 is a separate unit, attached to one or more of the user's chest, or abdomen, or nasal opening, and detects breathing status with one or more sensors, such as accelerometers, and communicates data to smart controller 3040. In some examples, RMD 3020 is a part of an integrated OSA suppression system 3000, co-located within patch 3010 and coupled to the same substrate as the other components.

Posture indication device 3030, worn by the user, detects changes in the user's body position as the position relates to sleeping or not sleeping, such as standing, or sitting, or prone, using one or more sensors, such as accelerometers, and notifies one or more of patch 3010, or smart controller 3040, or fob 3050 of such position change, thereby indicating the start or end of a sleep period. The specification of a sleep period may also be determined by other signals such as time of day, location of the user, amount of activity, posture, and other signals.

In some examples, user 3100 indicates explicitly their position as prone versus non-prone on smart controller 3040 through the use of display 3042 or acknowledgment button 3044, or with fob 3050, or other means. When smart controller is informed of the user's prone position, such as at bedtime, smart controller 3040 puts patch 3010 and respiration monitoring device 3020 into a state of monitoring apnea episodes. When smart controller 3040 is informed of the user's non-prone position or awake position, such as during daylight activities, smart controller 3040 puts patch and respiration monitoring device into a state of standby, no longer monitoring apnea episodes.

In some examples, when user 3100 indicates explicitly their position to smart controller 3040, posture indication device 3030 is not used, or the decision of posture indication device 3030 is overridden by the user's explicit input, such as when intending to sleep in a sitting position in a chair.

In some examples, smart controller 3040 determines the prone position of user 3100 without the use of the posture indication device 3030, such as through the use of a GPS, an accelerometer and other sensors attached to the user or separate from the user such as in the bed, analyzing data from these features internal to smart controller 3040. For example, the location of smart controller 3040 or fob 3050, or both, at the bedside or in the bed for longer than a pre-set time limit may be used as an indicator that the user is in the bed and in a prone position.

In some examples, user 3100 is prompted by and indicates to smart controller 3040 the locations in which the user sleeps, such as a bed in a bedroom, such that the data on locations collected in this manner by smart controller 3040 allows smart controller 3040 to determine when the user is in those new locations at a later time, such as when visiting another home or traveling.

In examples, the monitoring performed by RMD 3020, or any other elements, including patch 3010 itself, may detect the "trailing edge" of an apnea event, or the "leading edge" of an apnea event. The latter is preferred in order to trigger a stimulation to cut short or eliminate that apnea event.

In FIG. 32, OSA suppression system 3000 includes patch 3010 and respiration monitoring device (RMD) 3020. RMD 3020 may be a separate unit or integrated within patch 3010. It may also include smart controller 3040 or fob 3050. OSA system 3000 may or may not include posture indication device 3030. User 3100 may indicate to patch 3010 or smart controller 3040 or fob 3050 directly when the user is beginning a sleep period and again when the user is ending a sleep period. During the sleep period, when RMD 3020 senses an OSA episode, RMD 3020 then signals 3012 to smart controller 3040 or fob 3050 that the apnea should be suppressed using patch 3010. Smart controller 3040 then signals 3214 patch to activate the nerve via electrodes. Smart controller 3040 can also optionally signal 3216 to fob 3050 to record such an activation event that the apnea is suppressed for a period of time. In other examples, patch 3010, with integrated RMD 3020, can detect and automatically activate the nerve without needing any other components.

In some examples, smart controller 3040, or fob 3050, or both, is in control of a second person, such as a sleep partner, or a person sleeping in or near the user, or a caregiver, or a medical service provider such as in a nursing home. When respiration monitoring device 3020 detects an apnea episode, a notification is sent to smart controller 3040 or fob 3050, whereupon the second person may activate the user's patch 3010 to address the apnea episode.

In some examples, the second person may activate the stimulator based upon visual and auditory clues arising from the sleeping individual. The second person can also observe the effects of stimulation upon the user, and record reactions, either electronically in smart controller 3040 or in fob 3050, or manually such as in a sleep diary.

In some examples, multiple other persons may be notified of an apnea episode by respiration monitoring device 3020, such as in a skilled nursing facility with multiple medical personnel or a personal physician or a research clinician.

In some examples, the second person may monitor and respond to the signals from multiple users' OSA suppression and detection systems, or from a database of historical recordings of the user's sleep patterns, or a database of a large population of anonymized user sleep recordings that have been analyzed with pattern recognition or artificial intelligence (AI) techniques including machine learning and deep learning techniques.

In some examples, OSA suppression and detection systems 3000 use AI techniques such as correlation analysis to correlate real-time data recordings of the user with larger population databases to produce comparative or predictive analyses. In some examples, machine-learning algorithms are employed to build up the user's sleep history and provide specific predictors of sleep apnea severity and associated conditions.

In some examples OSA suppression system 3000 may use electrocardiogram (ECG), or encephalogram (EEG), or other means to detect the user is in the state of rapid eye movement (REM) sleep, or in non-REM sleep, and the system may apply apnea treatments in a manner appropriate to each type of sleep.

In some examples, respiration monitoring device 3020 may signal directly to patch 3010 to automatically suppress the apnea episode, bypassing smart controller 3040. Patch 3010, respiration monitoring device 3020, posture indication device 3030, smart controller 3040, and fob 3050 may be combined in a variety of ways to implement an OSA suppression system 3000. In some examples, the user 3100 uses fob 3050 to send data and controls to smart controller 3040.

In some examples, user 3100 uses fob 3050 to send data and controls to patch 3010. In some examples, user 3100 uses smart controller 3040 directly, and a fob 3050 is not used. In some examples, fob 3050 communicates data and controls with smart controller 3040 or to patch 3010, or both, through wireless means. In some examples, smart controller 3040 is implemented by a smartphone with functionality and apps as described above.

In some examples, user 3100 does not wear patch 3010, or respiration monitoring device 3020, or both, when in the non-prone or waking state. In some examples, analysis of respiration monitoring device 3020 measurements and posture indication device 3030 measurements is performed by one or both of patch 3010 and smart controller 3040.

In some examples, the communication of data and control among smart controller 3040, patch 3010, respiration monitoring device 3020, and posture indicator device 3030 may be by wireless means through the use of Bluetooth Low Energy (BLE), Wi-Fi, or other means.

In some examples, respiration monitoring device 3020 and posture indicator device 3030 may be combined into one unit with a common processor and common power source, data and control between respiration monitoring device 3020 and posture indicator device 3030 being in this case through wired or wireless means. This combined unit may communicate data and control with smart controller 3040 and patch 3010 through wireless means.

In some examples, respiration monitoring device 3020 and posture indicator device 3030 and smart controller 3040 may be combined into one unit with a common processor and common power source, data and control between respiration monitoring device 3020 and posture indicator device 3030 and smart controller 3040 being in this case through wired or wireless means. This combined unit may communicate data and control with patch 3010 through wireless means.

In some examples, respiration monitoring device 3020 and posture indicator device 3030, smart controller 3040, and patch 3010 may be combined into one unit with a common processor and common power source, data and control between respiration monitoring device and the Posture Indicator Device and the Smart Controller and patch 3010 being in this case through wired means.

The patch power source 3016, respiration monitoring device 3020 and posture indicator device 3030, smart controller 3040 and fob 3050 may be powered by battery or rechargeable means.

In some examples, patch 3010 sends an activation signal to the relevant nerve and repeats this signal according to a timer preset by the user 3100, the interval between electrode activations being selected to effectively suppress apnea episodes according to the user's preference.

In some examples, analysis of measurements from one or both of the smart controller 3040 and respiration monitoring device 3020 may be performed by processing in a remote server, in the cloud, or on a computer separate from smart controller 3040 but local to the user, such as a personal computer.

In some examples, the OSA suppression system 3000 measures the user's sleep schedule over a period of days or weeks or longer, noting the clock time when the user begins the sleep period and the clock time when the user wakes during or at the end of the sleep period. The system analyzes this data and determines the most effective clock times to activate OSA suppression system 3000.

In some examples, OSA suppression system 3000 collects time-based records of a user's sleep. These records are used to build a database of anonymized sleep period information from large populations of OSA suppression system 3000 users, or with recordings of sleep periods from other detection systems.

In some examples, the time-based records of sleep periods are supplemented with data entered manually by one or more observers of the user's sleep. The data recorded in the time-based database is sent to the cloud through a local network, such as a home mesh network, or directly over the Internet.

Sleep Studies

Sleep studies that employ polysomnography are typically used to diagnose sleep disorders. Polysomnography monitors brain waves (EEG), blood oxygen levels, heart rate, breathing, and eye and leg movements. These tests are generally conducted in sleep clinics and require overnight observation by trained sleep technicians as well as physicians. During the sleep study, if apnea is observed, the patient is awakened and a continuous positive airway pressure (CPAP) device is applied to the patient to continue to observe and record the same biometric signals while under the CPAP treatment.

Figure 33:
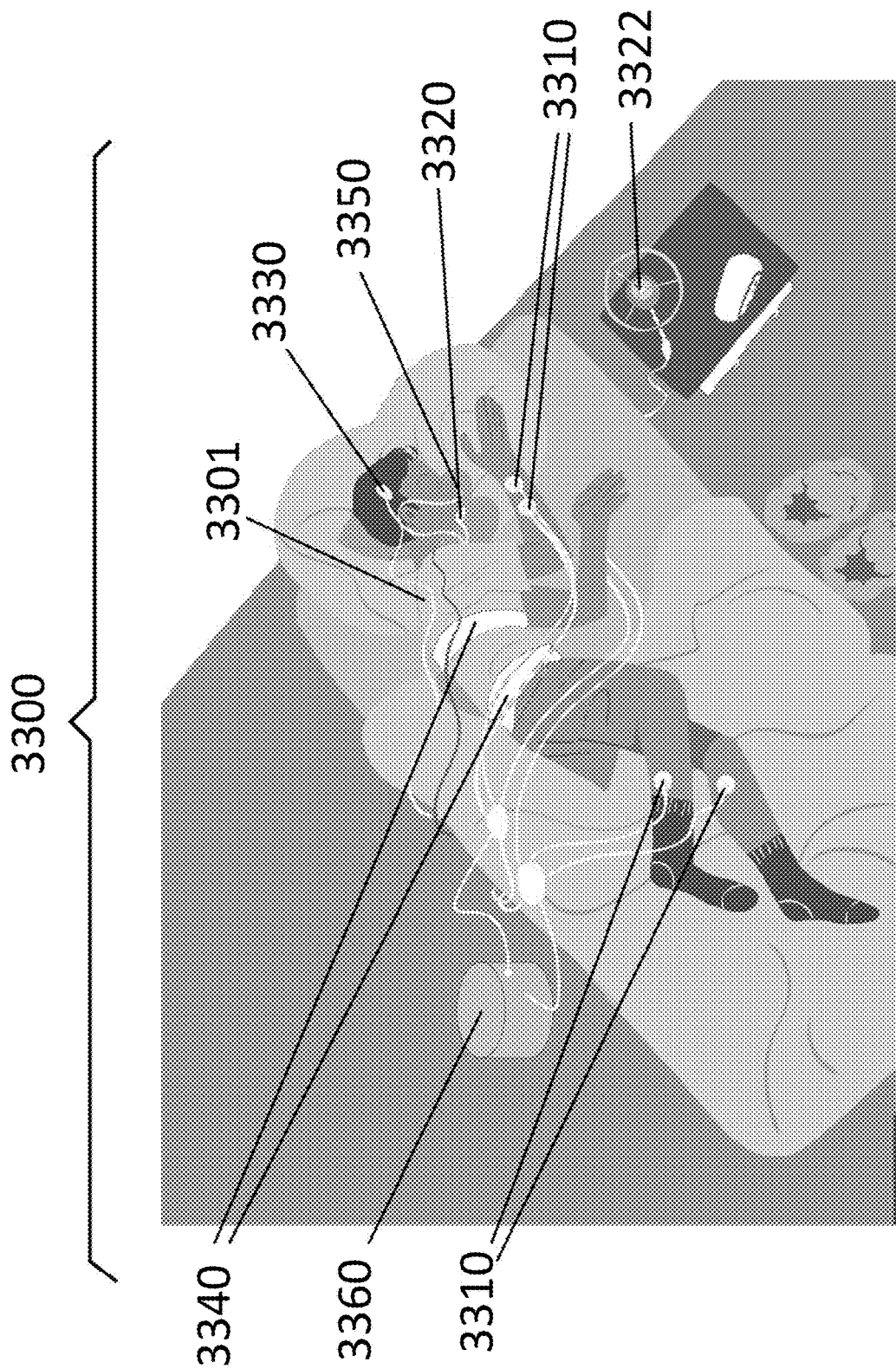
FIG. 33 illustrates a conventional polysomnography (PSG) system.

FIG. 33 illustrates a conventional polysomnography (PSG) system 3300. System 3300 includes a number of sensors and wires attached to user 3301 while sleeping, including a set of leg movement sensors 3310 with wires, a snoring sensor microphone 3320, an ambient noise microphone 3322, an EEG electrode 3330, one or more breathing detection belts 3340, and an airway sensor 3350. As shown in FIG. 33, the wires connecting the sensors to PSG Controller 3360 may interfere with the user's sleep, or the measurements may be adversely affected by user movement, or the measurements may be stopped due to disconnection of one or more sensor due to User movement.

Figure 34:
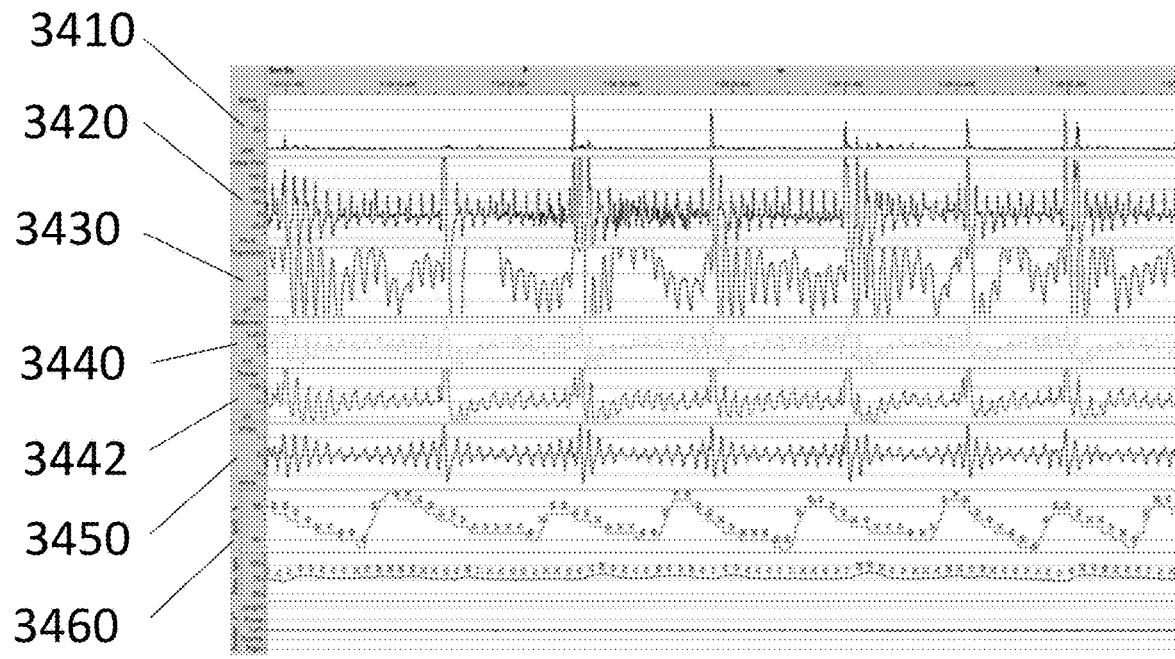
FIG. 34 illustrates an example of signals captured during a sleep period.

FIG. 34 illustrates an example of signals captured during a sleep period. Snoring is detected along snoring signal 3410; Breathing is detected along nasal flow signal 3420, and thermistor signal 3430; User movement is detected along abdomen signal 3440, and thorax signal 3442; respiratory airflow volume is detected along XFlow signal 3450, and SpO2 oxygen saturation signal 3460.

Figure 35:
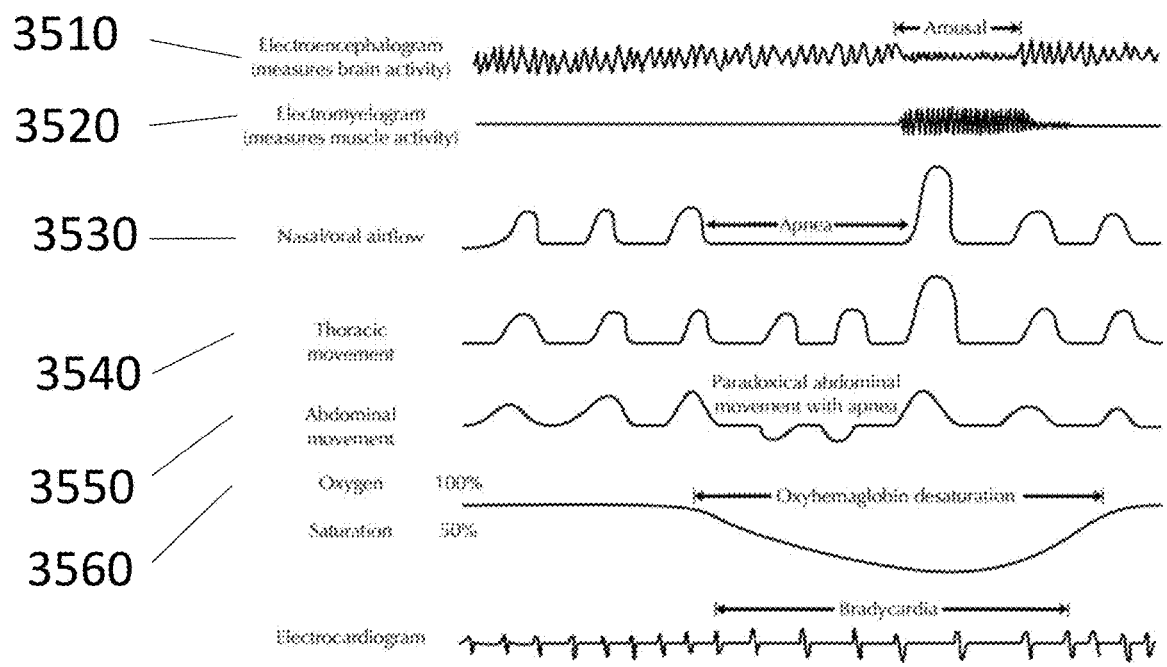
FIG. 35 illustrates measurements showing biometric data during a sleep study.

FIG. 35 illustrates measurements showing biometric data during a sleep study. The graph shows how only the nasal/oral airflow signal 3530 indicates a sleep apnea event without trailing the sleep apnea event, such as is shown by the oxygen saturation signal 3560 and the EMG signal 3520 which are trailing signals. The other signals include: the EEG 3510, the thoracic movement signal 3540, and the abdominal movement signal 3550—do not distinctively indicate a sleep apnea event.

Figure 36:
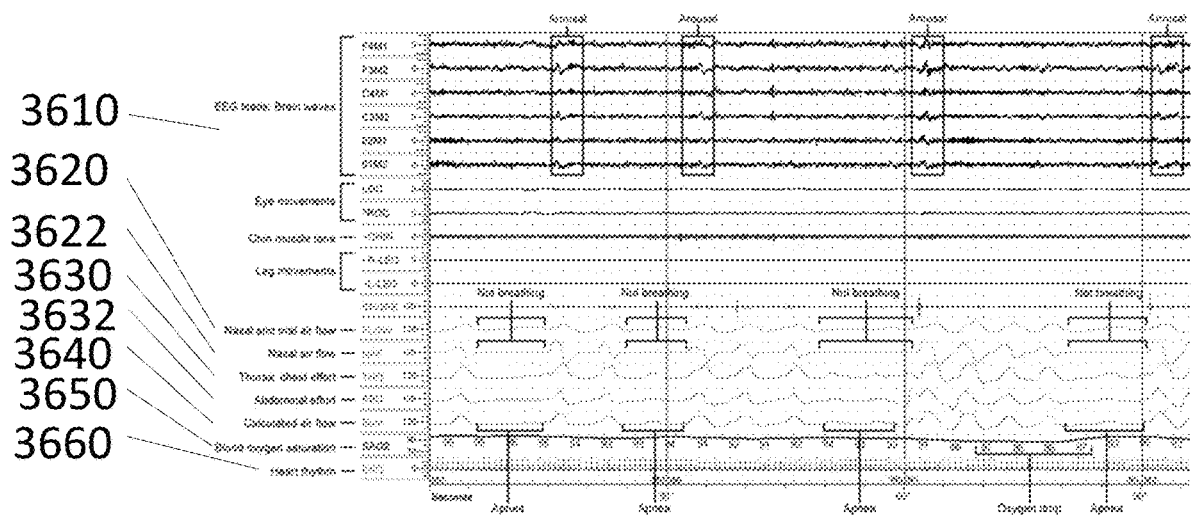
FIG. 36 illustrates measurements showing biometric data during a sleep study.

FIG. 36 illustrates measurements showing biometric data during a sleep study. The graph shows how airflow, measured by the nasal and oral air flow signal 3620, the nasal air flow signal 3622, the thorax chest effort 3630, the abdominal effort 3632, and the calculated air flow 3640 all indicate a sleep apnea event without trailing the sleep apnea event as is shown by the EEG signal 3610. The other signals: the blood oxygen saturation signal 3650, and the heart rhythm signal 3660—do not distinctively indicate a sleep apnea event.

Figure 37:
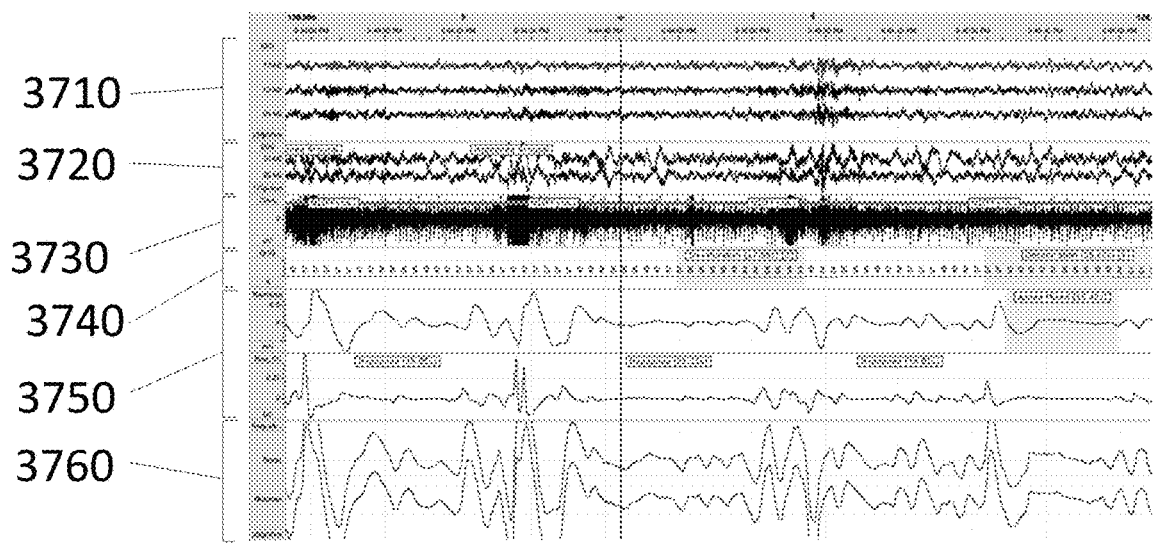
FIG. 37 illustrates measurements showing biometric data during a sleep study.

FIG. 37 illustrates measurements showing biometric data during a sleep study. Apnea events are strongly indicated coincident by breathing airflow measurements 3750, and somewhat indicated coincident by breathing effort measurements 3760; but either are not clearly indicated or only indicated after the onset of a sleep apnea event by EEG measurements 3710, Electroculogram (EOG) measurements 3720, Electromyelogram measurements 3730, and pulse oximetry measurements 3740.

Figure 38:
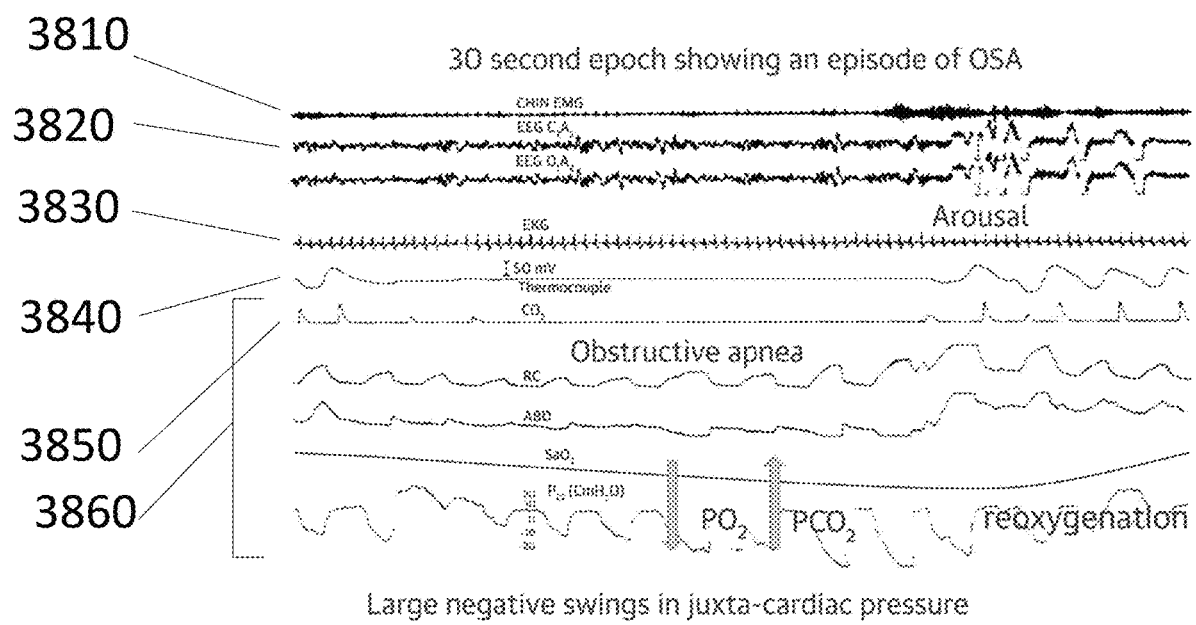
FIG. 38 illustrates measurements showing biometric data during a sleep study.

FIG. 38 illustrates measurements showing biometric data during a sleep study. Apnea events are only indicated after the event by EMG measurements 3810, EEG measurements 3820, EKG measurements 3830, and blood chemistry measurements 3860. The thermocouple measurements 3840, from which air flow is calculated, and CO2 levels 3850 correlate with coincident timing to sleep apnea events.

A novel discovery/conclusion in embodiments that is deduced from the graphs shown in FIGS. 34-38 is that measurement of breathing air flow is sufficient to indicate a sleep apnea event at a time coincident with the event and not trailing in time after the event has begun.

In embodiments, system 3000 measures user 3100 and analyzes the measured data and detects sleep apnea events in a manner which allows patch 3010 to stimulate user 3100 and limit the duration of the sleep apnea event. The physiological impact of OSA on user 3100 is reduced by shortening or eliminating sleep apnea events.

Figure 39:
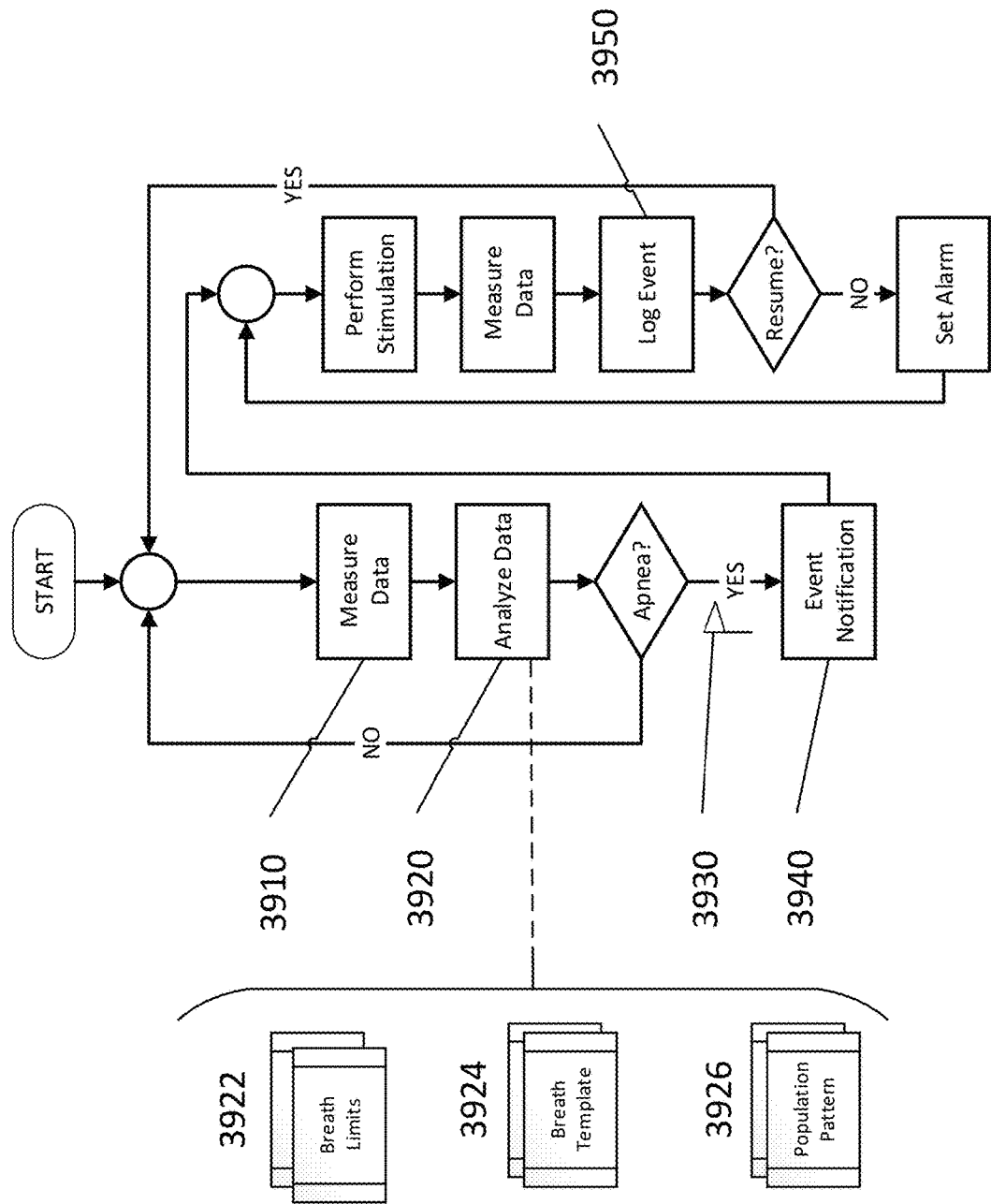
FIG. 39 illustrates functionality of the system when repeatedly measuring one or more physiological metrics on a user and then passing this measurement data to a smart controller.

FIG. 39 illustrates functionality of system 3000 when repeatedly measuring one or more physiological metrics on user 3100, and then passing this measurement data 3910 to smart controller 3040. Smart controller 3040 manipulates measurement data 3910 using OSA analysis module 3920, which mathematically assesses the pattern of breathing (or "breathing parameters") and determines if an expected breath has not been performed by the user. Smart controller 3040 continues to collect measurement data 3910 while executing OSA analysis module 3920.

In some examples, OSA analysis module 3920 compares the times of breaths and missed breaths against one or more breath limits 3922. If breathing is not detected before the limit or limits have been reached, then OSA analysis module 3920 sets an apnea event flag 3930.

In some examples, OSA analysis module 3920 compares the formats of breaths against a breath template 3924 that stores "normal" non OSA breathing patterns of the user. If the format of breathing falls outside of the bounds of breath template 3924, then OSA analysis module 3920 sets an apnea event flag 3930.

Using breath template 3924, example analysis can detect an OSA event on the occurrence of a first breath which is not a normal breath. For example, the upper airway begins to close during the end of a breath, preceding the obstruction of air flow which will prevent the next breath from occurring. When this closure begins, usually by lapse of tone in the genioglossus, the measurement values of the present breath begin to diverge from the normal measured values. The divergence may be measured as a "whistle" (i.e., change in frequency content), or reduction in amplitude (i.e., change in energy content) during the exhalation phase of this last breath.

OSA system 3000 detects this divergence and concludes that an OSA event is about to begin (i.e., that the next breath will be blocked). OSA system 3000 can then stimulate the user immediately, to re-open the airway by movement of the genioglossus. The OSA event is therefore avoided. The Apnea Hypopnea Index (AHI) number for the user will therefore not count an OSA event at this time and the AHI will be lowered. The anatomical effect of OSA will be reduced. As OSA 3000 system detects multiple imminent OSA events and prevents them, the AHI and anatomical effect is significantly reduced. AHI is a key parameter calculated to show the severity of obstructive sleep apnea in a person Example inventions reduce AHI. Specifically, the breathing tempo for many users is 12-20 breaths per minute; the time gap from one breath to the next may be 3-5 seconds. Concluding that an OSA event is occurring only after the first missed breath may mean that 3 seconds or more may have already passed. Therefore, example inventions, as disclosed, can detect an apnea event generally before a first breath is missed.

However, by detecting an imminent OSA event during the last normal breath and/or at the first missing breath, OSA system 3000 can reduce the stopped breathing interval to less than 10 seconds, thereby disqualifying it as an "apnea event", and therefore not counting toward the AHI. Reducing the duration of an event will also reduce the effect on SpO2, thereby disqualifying the event as a "hypopnea" event, and therefore not counting toward the AHI.

In some examples, OSA analysis module 3920 compares the times of breaths and missed breaths against data from a population pattern 3926 of other users of patch 3010. Population pattern 3926 may be assembled from previous use data from user 3100; or population pattern 3926 may be assembled from previous use data across a group of users, in some examples also including in the derivation of population pattern 3926 an analysis of user metrics separate from breathing such as age, weight, body mass index, and the like. If breathing falls outside the boundaries of population pattern 3926, then OSA analysis module 3920 sets apnea event flag 3930.

In some examples, OSA analysis module 3920 includes a combination of breath limits 3922, breath template 3924 and population pattern 3926 to perform the analysis of measurement data 3910.

System 3000 monitors apnea event flag 3930. When apnea event flag 3930 is set, then OSA event notification module 3940 sends one or more control signals or notifications to patch 3010. Patch 3010 reacts by initiating a nerve stimulation on user 3100 such that user 3100 resumes inhalation and exhalation.

In some examples, when system 3000 detects that breathing has not resumed after a nerve stimulation, system 3000 sends additional signals or notifications to patch 3010, to initiate a second or subsequent stimulation event.

In some examples, system 3000 uses a data logging module 3950 to log the preceding apnea event with at least a time stamp and an indication of whether the apnea event was curtailed or not. The information in the log of events may be used by smart controller 3040 to modify the choice of mathematical analyses from among the set of analytic processes in system 3000, to improve performance.

OSA analysis module 3920 includes software or firmware processes which may be executed by one or more of patch 3010, smart controller 3040, a computer separate from smart controller 3040, or in the cloud.

In some examples, some or all of breath limits 3922, breath template 3924 and population pattern 3926 are derived using machine learning. Training data sets can also be assembled from large numbers of user recordings of their nightly sleeping signals and patterns.

In some examples, some or all of breath limits 3922, breath template 3924 and population pattern 3926 are derived using artificial intelligence algorithms.

Breath limits 3922, breath template 3924 and population pattern 3926 or any other analytics can take as inputs data from other biometric devices such as smartwatches, smart patches or medical devices (either implanted or topical). The data can be acquired either directly in a point-to-point manner using wireless or wired means, or over BAN (Body Area Networks). Further, data from other devices can be acquired via the cloud or through the device's own data repositories.

Further, embodiments can implement adaptive control, as disclosed above, of the detection-stimulation closed loop, where the control is adapted continuously based on breath limits 3922, breath template 3924 and/or population pattern 3926. This control can be based upon real-time analytics and/or a "Behavior Library" which originates from the control unit or the cloud, and is similar to the libraries and models shown in FIG. 25A. The libraries can either be resident on patch 3010, or dynamically downloaded from the controller or cloud. The libraries include a Treatment Library, a Tissue Library and a Placement (location on the body) Library. The "Behavior Library" is the result of the AI/ML algorithms over large training sets or from other data analysis approaches. The Behavior Library is used in the predictive identification of oncoming apnea events, both obstructive as well as hypopnea events.

Using OSA system 3000, when an apnea event is observed by the system, stimulation can immediately be provided by the system and monitored through RMD 3020. Use of OSA system 3000 avoids awakening the user to administer CPAP to observe the effects of treatment. Thus, a sleep study with recording of basic OSA signals such as with the RMD 3020 can be done at home without the artifacts possibly introduced by a sleep clinic.

Further, the convenient and comfortable use of OSA system 3000 allows the system to collect data over a longer period of time without undue interference with sleep or other inconvenience when compared to conventional PSG systems.

As disclosed, examples allow OSA to be detected using only breathing parameters rather than additional non-breathing parameters used by more traditional testing. The detection of OSA using only breathing parameters can be done at the leading edge of an OSA event, thus leading to automatic treatment through stimulation. Analytics allows an individual's breathing parameters to be measured and identified and compared to a signature to provide a tailored treatment (i.e., by varying stimulation time and amount). Further, examples monitor OSA to determine the effectiveness of a stimulation treatment and this feedback can be used to modify the stimulation parameters.

Placement of the Patch for OSA Treatment

Figure 40:
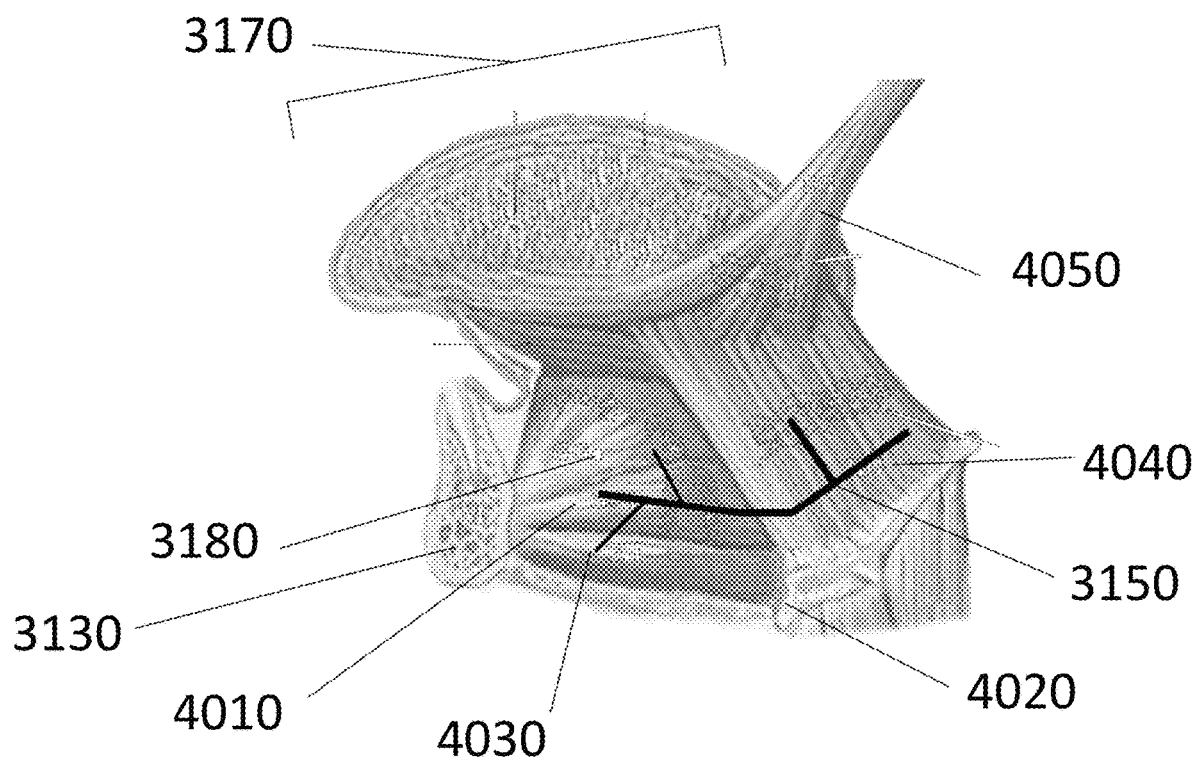
FIG. 40 illustrates anatomical features that are related to the placement of patch 3010 in accordance to example inventions.

FIG. 40 illustrates anatomical features that are related to the placement of patch 3010 in accordance to example inventions. The tongue 3170 is shown protruding beyond mandible 3130. The genioglossus muscle 3180 is anchored to the anterior mandible and produces tongue protrusion when activated by pulling forward. The geniohyoid muscle 4010 opens the mouth when activated, if the hyoid bone 4020 remains stationary. The styloglossus muscle 4050 retracts tongue 3170 toward the airway when activated, which is not an effect useful for treating OSA. The mylohyoid muscle 4030 pulls on the hyoid bone when activated, pulling the mandible down.

Figure 41A:
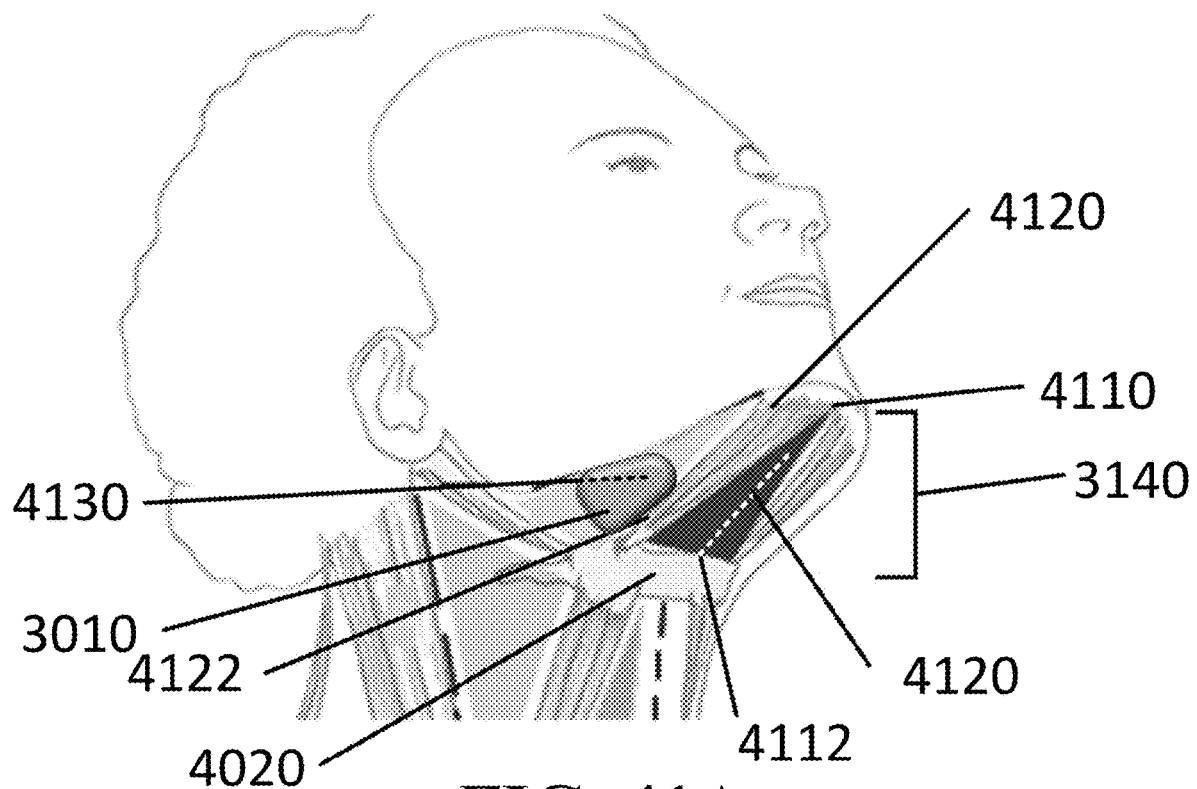
FIG. 41A illustrates a placement of one of a set of neck related patches 3010 in accordance to example inventions.

FIG. 41A illustrates a placement of one of a set of neck related patches 3010 in accordance to example inventions. As shown, each patch 3010 is placed on or near submental triangle 3140 to affect specific nerves and muscles. Patch 3010 is placed axially along the hypoglossal nerve that innervates genioglossus muscle 3180, either bilaterally with two or more pairs of electrodes, or as a single pair of electrodes. Placement is at the anterior end of hypoglossal nerve 3150, to avoid activation of styloglossus muscle 4050.

In one example, patch 3010 placement is on the submental triangle 4130 at the front or back of the median 4110 and 4112, or both, to activate genioglossus muscle 3180.

In another example, patch 3010 placement is to the left or right of median 4120 and 4122, or both, to activate mylohyoid muscle 4030.

In another example, patch 3010 placement is to the left or right margins of submental triangle 4130, or both, to activate genioglossus muscle 3180 through the smaller digastric muscles 4020, which do not affect the shape of tongue 3170.

Figure 41B:
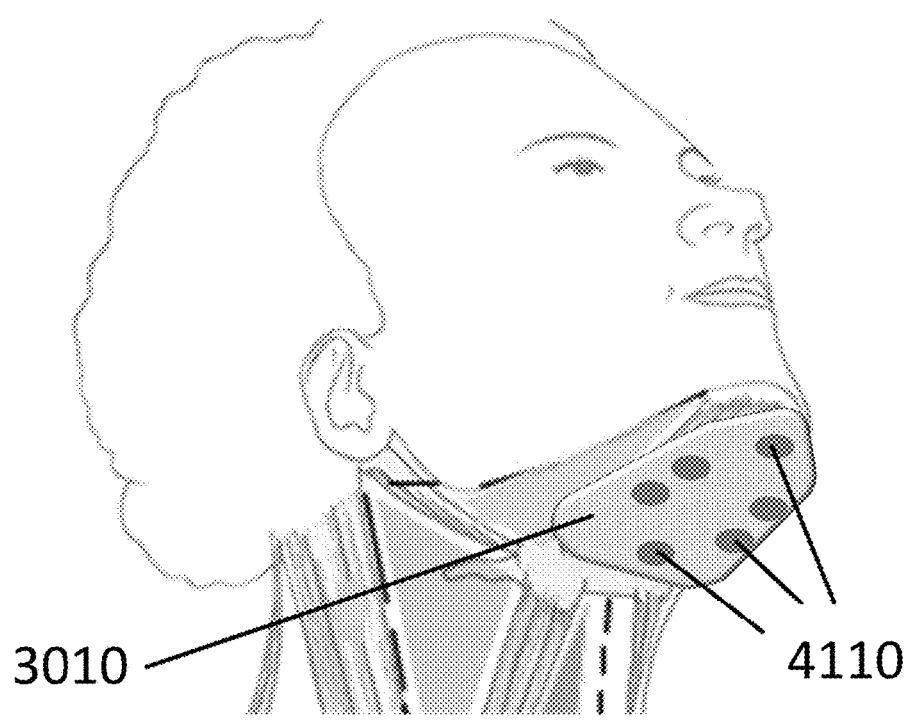
FIG. 41B illustrates a single patch, with multiple electrodes, singly or in pairs, to activate one or more nerves in accordance to example inventions.

FIG. 41B illustrates a single patch 3010, with multiple electrodes 4110, singly or in pairs, to activate one or more nerves in accordance to example inventions.

Figure 42A:
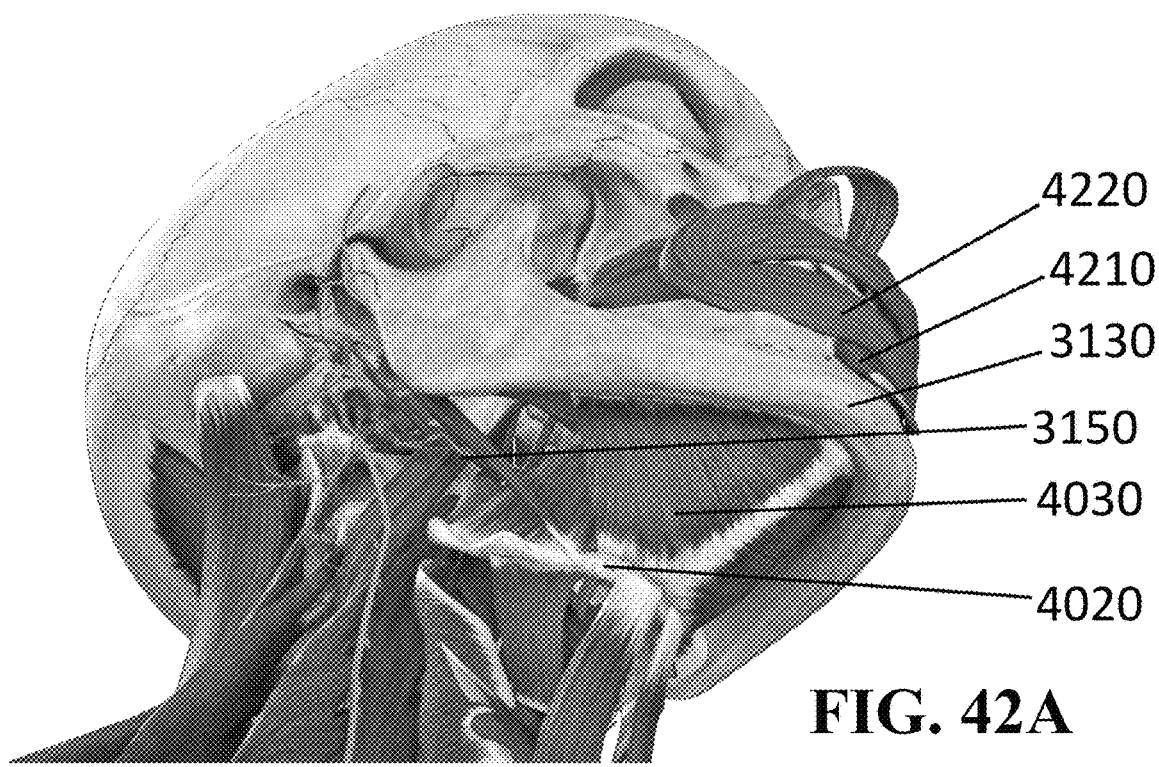
FIGS. 42A and 42B illustrate the anatomical features related to the placement of the patch at the mandible in accordance to example inventions.
Figure 42B:
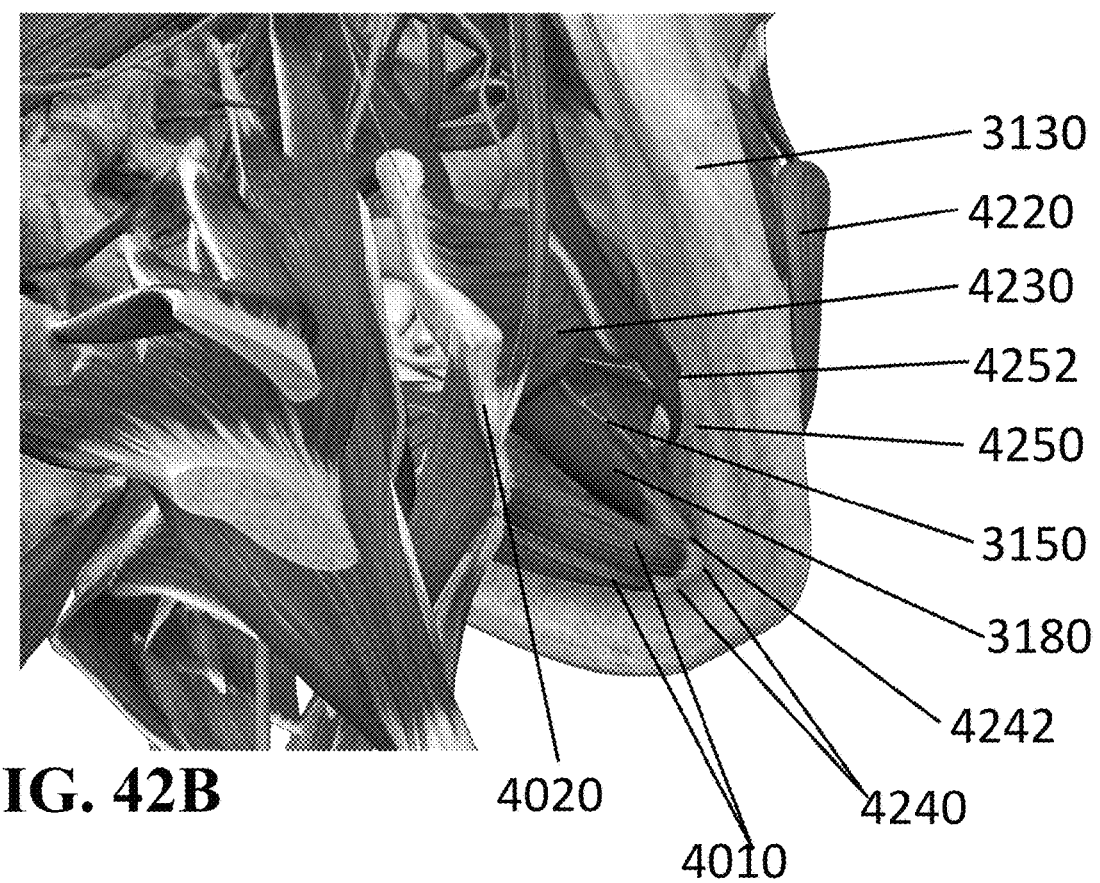

FIGS. 42A and 42B illustrate the anatomical features related to the placement of patch 3010 at mandible 3130 in accordance to example inventions. As disclosed, genioglossus muscle 3180 contracts when activated by hypoglossal nerve 3150. Genioglossus muscle 3180 and geniohyoid muscle 4010 are anchored to the mandible at the mental spine 4250. Geniohyoid muscle 4010 is attached at the two inferior spines 4240. Genioglossus muscle 3180 is attached at the two superior spines 4242.

Figure 43A:
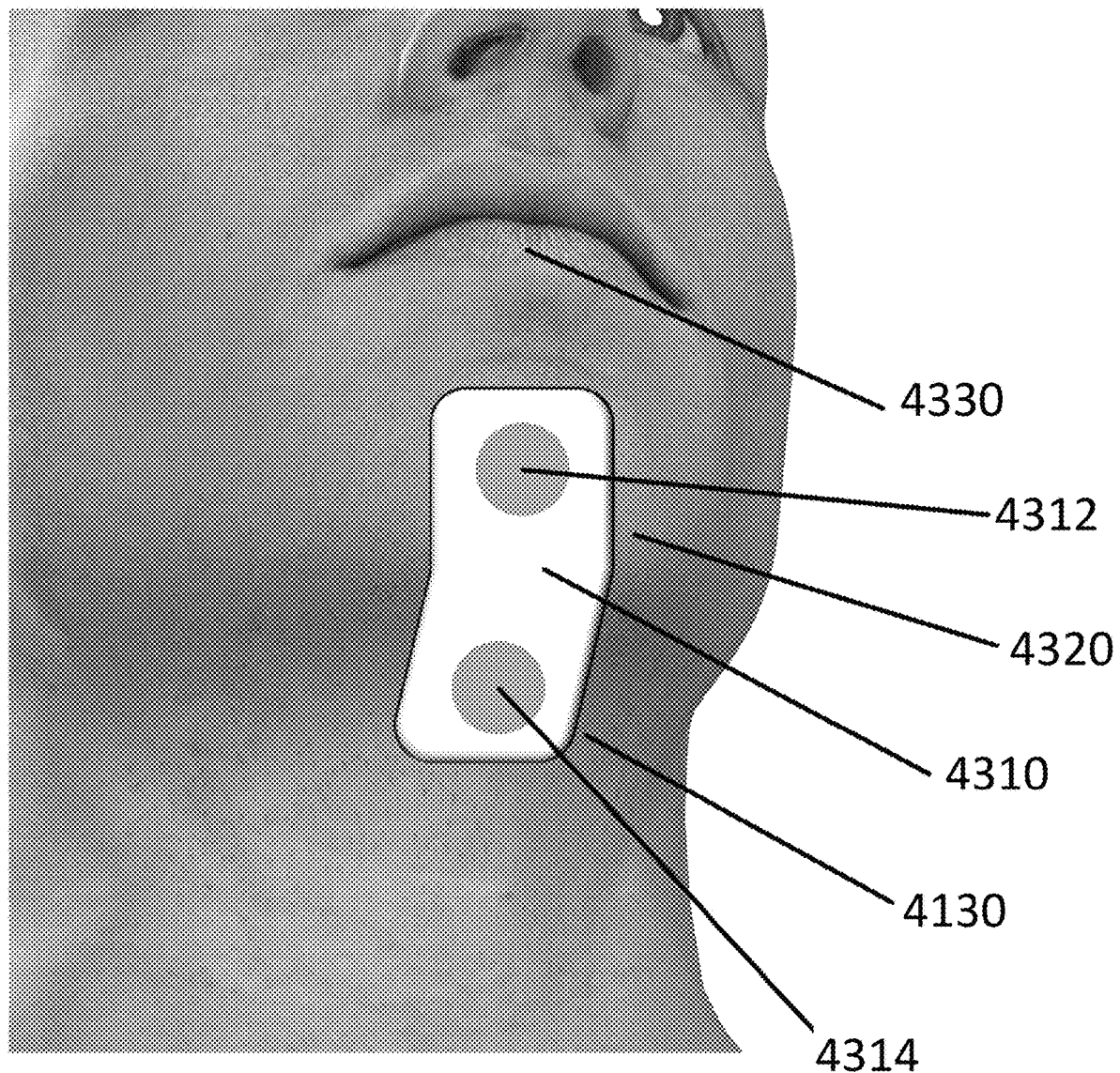
FIGS. 43A and 43B illustrate the orientation related to the placement of a chin based patch at the chin in accordance to example inventions.
Figure 43B:
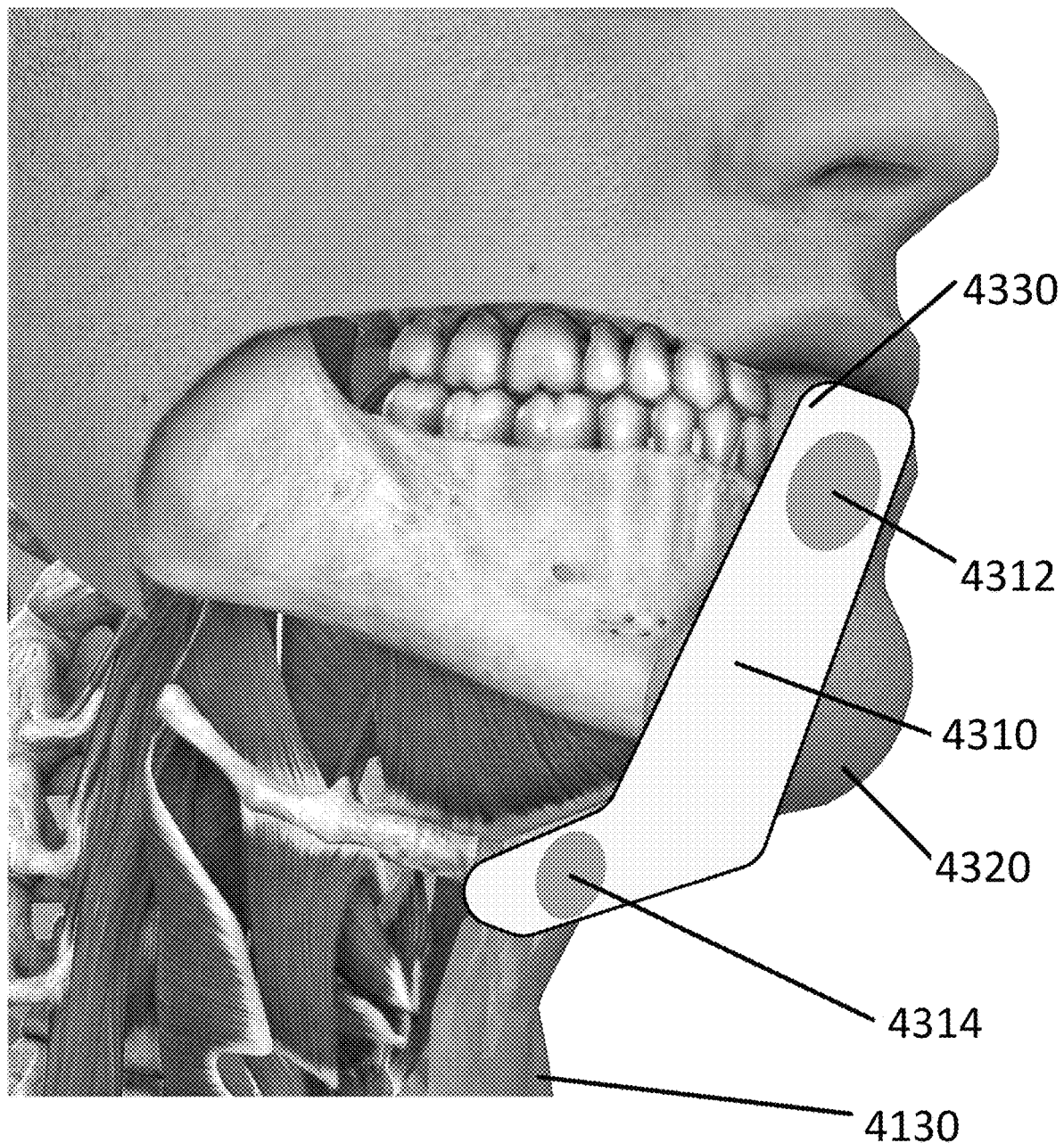

FIGS. 43A and 43B illustrate the orientation related to the placement of a chin based patch at the chin 4320 in accordance to example inventions. In the example of FIGS. 43A and B, patch 3010 has been designed as a "chin patch" device 4310 to extend from the neck 3110, under mandible 3130, above hyoid 4020; up across chin 4320, ending at the lower lip 4330, to affect specific nerves and muscles.

Chin patch 4310 uses a primary electrode 4312 and a secondary electrode 4314 to create an electrical field which is oriented to cross axially along geniohyoid muscle 4010, and to intersect the anterior end of genioglossus muscle 3180, to avoid activation of styloglossus muscle 4050.

In one example, one or both of primary electrode 4312 and secondary electrode 4314 are divided into multiple sub-electrodes, these sub-electrodes being energized using voltages, timings and waveform shapes to refine the direction of the electric field.

Figure 43C:
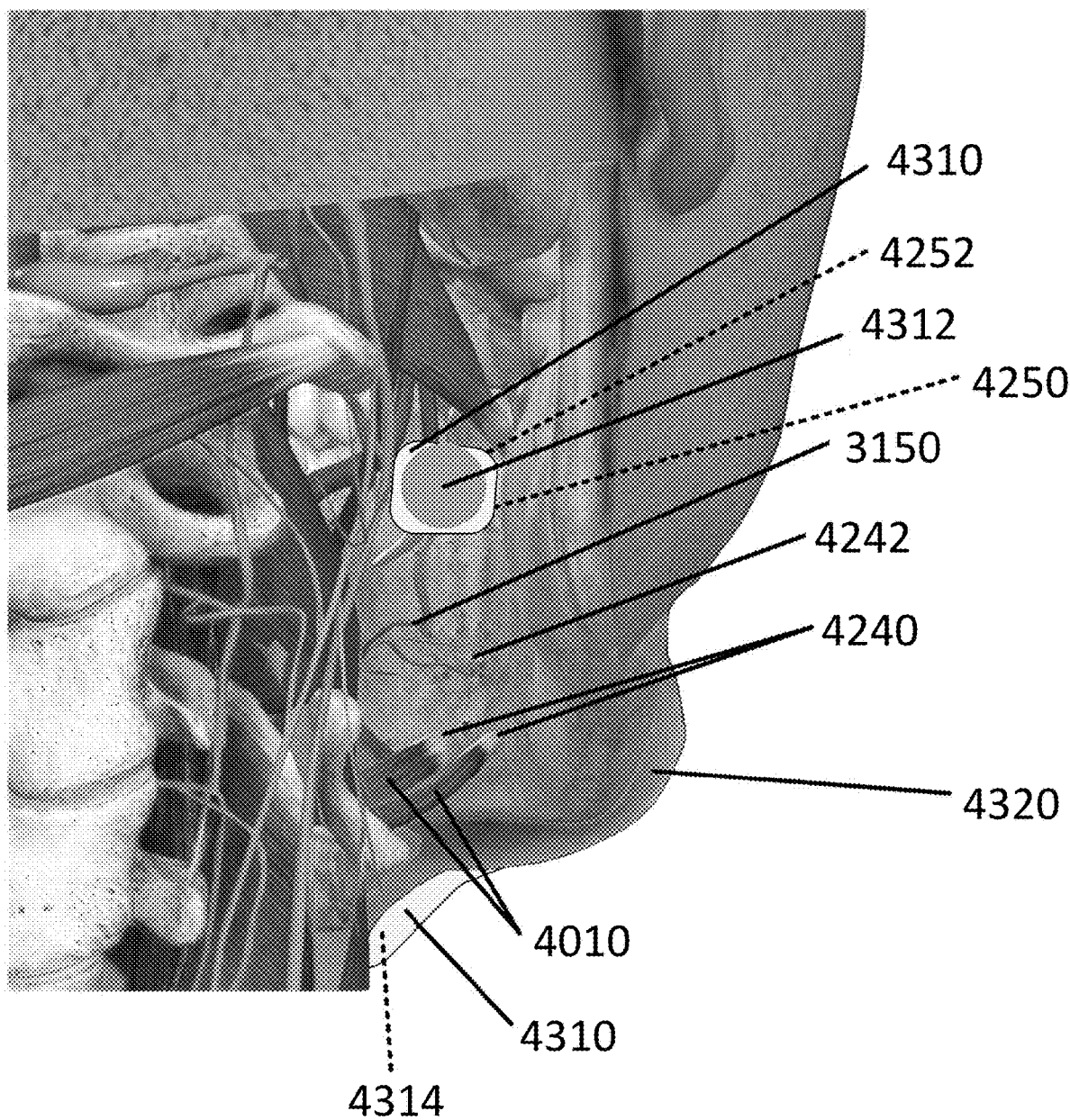
FIGS. 43C and 43D illustrate the orientation related to the placement of a mandible based patch at the mandible in accordance to example inventions.
Figure 43D:
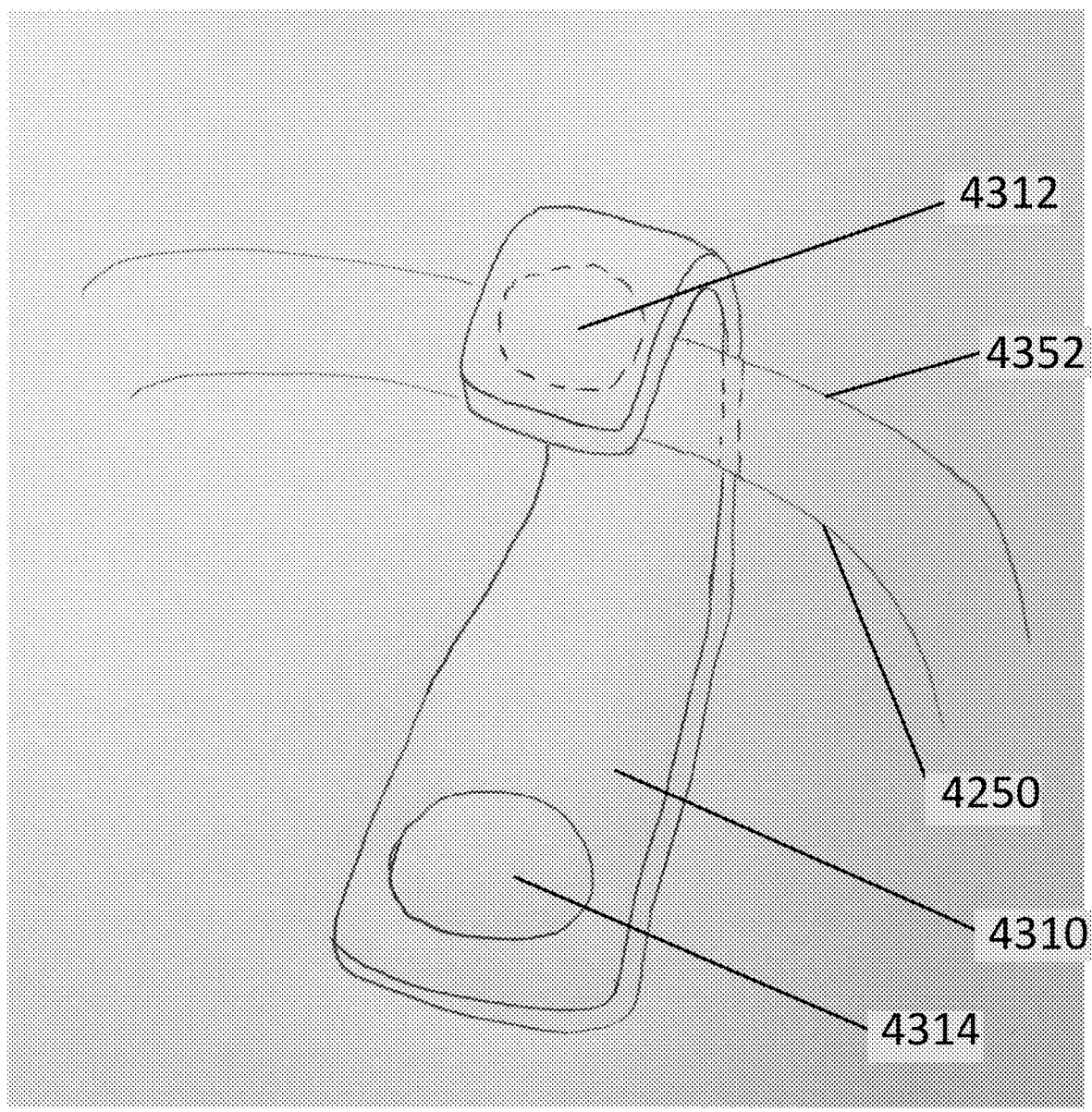

FIGS. 43C and 43D illustrate the orientation related to the placement of a mandible based patch at mandible 3130 in accordance to example inventions. Patch 3010 has been designed as a mandibular patch device 4310 to extend from neck 3110, under mandible 3130, above hyoid 4020, up across chin 4320; over lower lip 4330, ending at inner gum line 4250 of the mandible after crossing over lower teeth 4352 to affect specific nerves and muscles.

FIG. 43C illustrates a view looking forward through the tissues of the right side of the face in accordance to example inventions. FIG. 43C illustrates genioglossus muscle 3180, genioglossal nerve 3150, and other nearby structures, with primary electrode 4312 between the lower gum line 4250 and the lower teeth 4252. In FIG. 43C, the secondary electrode 4314 is partially hidden behind the curve of the jaw.

FIG. 43D illustrates the view looking outward from inside the mouth, through the tissues of the lower jaw, limited at the top by the lower teeth 4352 in accordance to example inventions. FIG. 43D illustrates primary electrode 4312 inside the lower jaw at the inner gum line, behind the main body of the patch 4310, and shows secondary electrode 4314 on the posterior surface of patch 4310, facing the skin at the neck 3110.

Patch 4310 uses primary electrode 4312 and secondary electrode 4314 to create an electrical field which is oriented to cross axially along geniohyoid muscle 4010, and to intersect the anterior end of genioglossus muscle 3180, to avoid activation of styloglossus muscle 4050.

An example, one or both of primary electrode 4312 and secondary electrode 4314 are divided into multiple sub-electrodes, these sub-electrodes being energized using voltages, timings and waveform shapes to refine the direction of the electric field.

The use of sub-electrodes couples energy efficiently into the target tissues, such as genioglossus muscle 3180 and geniohyoid muscle 4010, while passing effectively through or around other tissues, such as mandible 3130 and lower teeth 4352, these tissues being obstructive to electrical energy due to their higher electrical impedances than the impedances of the target nerves and muscles.

As an example, mandibular patch 4310 has an interior stiffening element extending through the curved portion over lower teeth 4352, this stiffener holding mandibular patch 4310 securely to lower teeth 4352 while worn by user 3110 by using a clasping force directed to one or both of the anterior and posterior sides lower teeth 4250.

In another example, mandibular patch 4310 has an adhesive surface extending through the curved portion over lower teeth 4250, this adhesive holding mandibular patch 4310 securely to lower teeth 4250 while worn by user 3110 by using an adhesive selected to resist the moisture and movement in this area of user's 3110 mouth while also being temporary, such that user 3110 can remove mandibular patch 4310 after use.

OSA Treatment

Patch 3010 stimulates the one or more nerves using a series of electrical pulses in a pattern with specific frequency, waveform, intensity and duration. The pulses are applied at an intensity below that level which stimulates a painful sensation and below that level which wakes user 3100. As such, the intensity of the applied pulses is adjusted for each user and may be adjusted and applied by each user each time patch 3010 (or any other patches disclosed herein) is applied, since effective intensity may be different according to skin condition, dampness, dryness, weight change, specific location of placement and other factors. In this manner, the electrical pattern of stimulation pulses is adjusted for each application.

As an example, the applied frequency of the stimulation pulses is in the range of 2 Hz to 50 Hz, and the applied current applied is in the range 0.1-10 mA.

As another example, processor 3018 adjusts the intensity of applied pulses, or the duration of application, or both, using data from the monitoring device or devices, such as RMD 3020, included in OSA detection and stimulation system 3000 of FIG. 30.

As another example, smart controller 3040 adjusts the intensity of applied pulses, or the duration of application, or both, using data exchanged with patch 3010 and its processor 3018. The exchanged data includes data from the monitoring device or devices included in OSA detection and stimulation system 3000 of FIG. 30.

As another example, one or both of with patch 3010 and smart controller 3040 adjusts the intensity or the duration of the applied pulses, or both, and user 3100 adjusts the intensity and the duration of the applied pulses, or both, with all adjustments limited to preset ranges.

As disclosed, embodiments detect and then treat OSA using electrical stimulation that is generated and applied via patch 3010. In general, for a neck oriented treatment, patch is placed on or near submental triangle 3140 and axially along the hypoglossal nerve. In other examples, the patch is placed on a user's chin or on a user's mandible. The electrical stimulation applies pulses having an intensity that is automatically adjusted for each user and each application by the user due to changing conditions.

Several examples are specifically illustrated and/or described herein. However, it will be appreciated that modifications and variations of the disclosed examples are covered by the above teachings and within the purview of the appended claims without departing from the spirit and intended scope of the invention.

What is claimed is:

1. A method of treatment for obstructive sleep apnea (OSA) of a user, the method comprising:
affixing a patch externally on a dermis of the user, the patch comprising a flexible substrate, an adhesive on a first side adapted to adhere to the dermis of the user, a processor directly coupled to the substrate, and electrodes directly coupled to the substrate;
detecting an occurrence of OSA; and
activating the patch in response to the detecting, the activating comprising generating an electrical stimuli via the electrodes to activate a genioglossus muscle of the user, the electrical stimuli comprising square waves having an amplitude between 10 and 100 volts, pulse widths between 100 and 500 microseconds, and a pulse repetition rate of between 2 and 60 pulses per second.

2. The method of claim 1, a placement of the patch on the user causing the activating to avoid activation of a styloglossus muscle of the user.

3. The method of claim 2, the placement comprises affixing the patch to a neck of the user on or near a submental triangle of the user.

4. The method of claim 2, the placement comprises affixing the patch to extend from a neck of the user, across a chin of the user, and ending on a lower lip of the user.

5. The method of claim 2, the placement comprises affixing the patch to extend from a neck of the user, across a chin of the user, over a lower lip of the user, crossing over lower teeth of the user, and ending at an inner gum line of the user.

6. The method of claim 2, the placement causing the electrical stimuli to cross axially along a geniohyoid muscle of the user.

7. The method of claim 1, the electrical stimuli causing a tongue of the user to move.

8. The method of claim 1, the electrical stimuli comprising a series of pulses with a pattern comprising an intensity and a duration, further comprising adjusting the intensity or the duration of the pattern after each affixing of the patch to the dermis of the user.

9. The method of claim 8, wherein an applied frequency of the pulses is 2 Hz-50 Hz.

10. The method of claim 1, the detecting the occurrence of OSA comprising:
measuring a pattern of breathing by a user; and
analyzing the pattern using stored breath limits to determine one or more missed breaths by the user.

11. The method of claim 10, the detecting the occurrence of OSA based only on the analyzing and using only breathing parameters of the user.

12. The method of claim 1, the patch comprising one or more sensors, further comprising
placing a tag on or near a target nerve;
receiving an activation signal from the electrodes to a degree proportional to a strength of an activation pulse at the target nerve received by the sensors in response to the electrical stimuli; and
using the activation signal to re-orient a placement of the patch.

13. A obstructive sleep apnea (OSA) treatment system comprising:
a patch adapted to be externally applied on a dermis of a user, the patch comprising a flexible substrate, an adhesive on a first side adapted to adhere to the dermis of the user, a processor directly coupled to the substrate, and electrodes directly coupled to the substrate;
the processor, in response to detecting an occurrence of obstructive sleep apnea (OSA), adapted to activate the patch, the activating comprising generating an electrical stimuli via the electrodes to activate a genioglossus muscle of the user, the electrical stimuli comprising square waves having an amplitude between 10 and 100 volts, pulse widths between 100 and 500 microseconds, and a pulse repetition rate of between 2 and 60 pulses per second.

14. The system of claim 13, the patch adapted to have a placement on the user that causes the activating to avoid activation of a styloglossus muscle of the user.

15. The system of claim 14, the placement comprises affixing the patch to a neck of the user on or near a submental triangle of the user.

16. The system of claim 14, the placement comprises affixing the patch to extend from a neck of the user, across a chin of the user, and ending on a lower lip of the user.

17. The system of claim 14, the placement comprises affixing the patch to extend from a neck of the user, across a chin of the user, over a lower lip of the user, crossing over lower teeth of the user, and ending at an inner gum line of the user.

18. The system of claim 14, the placement causing the electrical stimuli to cross axially along a geniohyoid muscle of the user.

19. The system of claim 13, the electrical stimuli adapted to cause a tongue of the user to move.

20. The system of claim 13, the electrical stimuli comprising a series of pulses with a pattern comprising an intensity and a duration, the processor further adapted to adjust the intensity or the duration of the pattern after each affixing of the patch to the dermis of the user.

21. The system of claim 13, the patch comprising one or more sensors, the processor further adapted to, in response to placing a tag on or near a target nerve:
receive an activation signal from the electrodes to a degree proportional to a strength of an activation pulse at the target nerve received by the sensors in response to the electrical stimuli; and
use the activation signal to re-orient a placement of the patch.

22. The system of claim 13, the detecting the occurrence of OSA comprising:
measuring a pattern of breathing by a user; and
analyzing the pattern using stored breath limits to determine one or more missed breaths by the user;
wherein the detecting the occurrence of OSA is based only on the analyzing and using only breathing parameters of the user.

* * * * *